(12) United States Patent
Hughes et al.

(10) Patent No.: US 8,481,069 B2
(45) Date of Patent: *Jul. 9, 2013

(54) TYROSINE KINASE MICROSPHERES

(75) Inventors: Patrick M. Hughes, Aliso Viejo, CA (US); Christian Sarrazin, Pergomas (FR); Elisabeth Rossi, Nice (FR); Michele Boix, Cantaron (FR)

(73) Assignee: Allergan, Inc., Irvine, CA (US)

( * ) Notice: Subject to any disclaimer, the term of this patent is extended or adjusted under 35 U.S.C. 154(b) by 1603 days.

This patent is subject to a terminal disclaimer.

(21) Appl. No.: 11/119,463

(22) Filed: Apr. 29, 2005

(65) Prior Publication Data

US 2005/0244477 A1 Nov. 3, 2005

Related U.S. Application Data

(63) Continuation-in-part of application No. 10/837,361, filed on Apr. 30, 2004, now Pat. No. 7,771,742.

(51) Int. Cl.
*A61F 2/14* (2006.01)

(52) U.S. Cl.
USPC .......................................................... 424/428

(58) Field of Classification Search
None
See application file for complete search history.

(56) References Cited

U.S. PATENT DOCUMENTS

| | | | |
|---|---|---|---|
| 4,327,725 A | 5/1982 | Cortese et al. | 128/260 |
| 4,521,210 A | 6/1985 | Wong | 604/8 |
| 4,853,224 A | 8/1989 | Wong | 424/427 |
| 4,997,652 A | 3/1991 | Wong | 424/428 |
| 5,164,188 A | 11/1992 | Wong | 424/428 |
| 5,443,505 A | 8/1995 | Wong et al. | 623/4 |
| 5,501,856 A | 3/1996 | Ohtori et al. | 424/428 |
| 5,766,242 A | 6/1998 | Wong et al. | 623/4 |
| 5,792,783 A | 8/1998 | Tang et al. | |
| 5,824,072 A | 10/1998 | Wong | 623/4 |
| 5,834,504 A | 11/1998 | Tang et al. | |
| 5,869,079 A | 2/1999 | Wong et al. | 424/426 |
| 5,883,113 A | 3/1999 | Tang et al. | |
| 5,883,116 A | 3/1999 | Tang et al. | |
| 5,886,020 A | 3/1999 | Tang et al. | |

(Continued)

FOREIGN PATENT DOCUMENTS

| | | |
|---|---|---|
| WO | 96-10397 | 4/1996 |
| WO | 96-38174 | 12/1996 |

(Continued)

OTHER PUBLICATIONS

Busse et al., "Tyrosine kinase inhibitors: rationale, mechanisms of action, and implications for drug resistance", Semin Oncol 28(suppl 16) 47-55 (2001).

(Continued)

*Primary Examiner* — Carlos Azpuru
(74) *Attorney, Agent, or Firm* — Laura L. Wine; Joel B. German; Debra D. Condino

(57) ABSTRACT

Biocompatible intraocular microspheres include a tyrosine kinase inhibitor and a biodegradable polymer that is effective to facilitate release of the tyrosine kinase inhibitor into the vitreous of an eye for an extended period of time. The therapeutic agents of the microspheres can be associated with a biodegradable polymer matrix, such as a matrix that is substantially free of a polyvinyl alcohol. The microspheres can be placed into an eye to treat or reduce the occurrence of one or more ocular conditions.

7 Claims, 15 Drawing Sheets

U.S. PATENT DOCUMENTS

| | | | |
|---|---|---|---|
| 5,919,813 A | 7/1999 | de Juan, Jr. | 514/432 |
| 6,074,661 A | 6/2000 | Olejnik et al. | 424/427 |
| 6,306,426 B1 | 10/2001 | Olejnik et al. | |
| 6,331,313 B1 | 12/2001 | Wong et al. | |
| 6,369,116 B1 | 4/2002 | Wong et al. | 514/913 |
| 6,541,504 B1 | 4/2003 | Andrews et al. | |
| 6,559,173 B1 | 5/2003 | Andrews et al. | |
| 6,699,493 B2 | 3/2004 | Wong | 424/428 |
| 6,699,863 B1 | 3/2004 | Andrews et al. | |
| 6,713,081 B2 | 3/2004 | Robinson et al. | 424/427 |
| 6,747,025 B1 | 6/2004 | Andrews et al. | |
| 6,765,012 B2 | 7/2004 | Andrews et al. | |
| 7,005,444 B2 | 2/2006 | Andrews et al. | |
| 7,015,220 B2 | 3/2006 | Andrews et al. | |
| 7,060,844 B2 | 6/2006 | Andrews et al. | |
| 7,771,742 B2 * | 8/2010 | Hughes et al. | 424/428 |
| 2003/0119812 A1 | 6/2003 | Brazzell et al. | |
| 2003/0199478 A1 | 10/2003 | Andrews et al. | 514/80 |
| 2003/0225152 A1 | 12/2003 | Andrews et al. | 514/419 |
| 2004/0054374 A1 | 3/2004 | Weber et al. | 606/107 |
| 2005/0003007 A1 | 1/2005 | Boix et al. | 424/486 |
| 2005/0009910 A1 | 1/2005 | Hughes et al. | 514/559 |
| 2007/0066541 A1 | 3/2007 | Hughes et al. | |
| 2008/0241252 A1 | 10/2008 | Lyons et al. | |
| 2009/0099181 A1 | 4/2009 | Wurster et al. | |
| 2009/0286773 A1 | 11/2009 | Spada et al. | |

FOREIGN PATENT DOCUMENTS

| | | |
|---|---|---|
| WO | 97-34920 | 9/1997 |
| WO | WO 02/85248 A2 | 4/2002 |
| WO | 03-027102 | 4/2003 |
| WO | 03-084951 | 10/2003 |
| WO | 2004-112748 | 12/2004 |
| WO | 2005-107708 | 11/2005 |
| WO | 2005-107706 | 11/2006 |

OTHER PUBLICATIONS

Fabbro et al., "Protein tyrosine kinase inhibitors: new treatment modalities?", Current Opinion in Pharmacology, 2:374-381 (2002).

Goel et al., "Tyrosine Kinase Inhibitors: A Clinical Perspective", Current Oncology Reports, 4:9-19 (2002).

Haluska et al., "Receptor tyrosine kinase inhibitors", Current Opinion in Investigational Drugs, 2(2):280-286 (2001).

Heller, Biodegradable Polymers in Controlled Drug Delivery, In: CRC Critical Reviews in Therapeutic Drug Carrier Systems, vol. 1, CRC Press, Boca Raton, FL 1987, pp. 39-90.

Hubbard et al., "Protein tyrosine kinase structure and function", Annu. Rev. Biochem., 69:373-98 (2000).

USP 23; NF 18 (1995) pp. 1790-1798.

Plowman et al, "Receptor Tyrosine Kinases as Targets for Drug Intervention",1994, DN&P 7(6): 334-339.

Bolen, "Nonreceptor tyrosine protein kinases", 1993, Oncogen 8: 2025-2031.

Antcliff R., et al Marshall J., The Pathogenesis of Edema In Diabetic Maculopathy, Semin Ophthalmol 1999; 14:223-232.

Hillery et al, Drug Delivery and Targetting for Pharmacists and Pharmaceutical Scientists, 2001, published by Taylor & Francis, pp. 64-67, 84-96, 99-101.

Hcaplus 2006: 14038, "Preparation of (3Z)-3-(2,3-dihydro-1H-inden-1-ylidene)-1,3-dihydro-2H-indol-2-ones as tyrosine kinase inhibitors", Andrews et al.

Merkli A et al: "Use of Insoluble Biodegradable Polymers in Ophthalmic Systems for the Sustained Release of Drugs" European Journal of Pharmaceutics and Biopharmaceutics, Elsevier Science Publishers B.V., Amsterdam, NL, vol. 41, No. 5, Oct. 1, 1995, 271-281.

Laird et al: "Small molecule tyrosine kinase inhibitors: clinical development of anticancer agents" Expert Opinion on Investigational Drugs, Ashley Publications Ltd., London, GB, vol. 12, No. 1, Jan. 2003, pp. 51-64.

* cited by examiner

3-{[4-(2-Diethylamino-ethoxy)-phenylamino]-methylene}-6-fluoro-1,3-dihydro-indol-2-one

[3-(6-Fluoro-2-oxo-1,2-dihydro-indol-3-ylidene)-1,3-dihydro-isobenzofuran-1-yl]-acetic acid

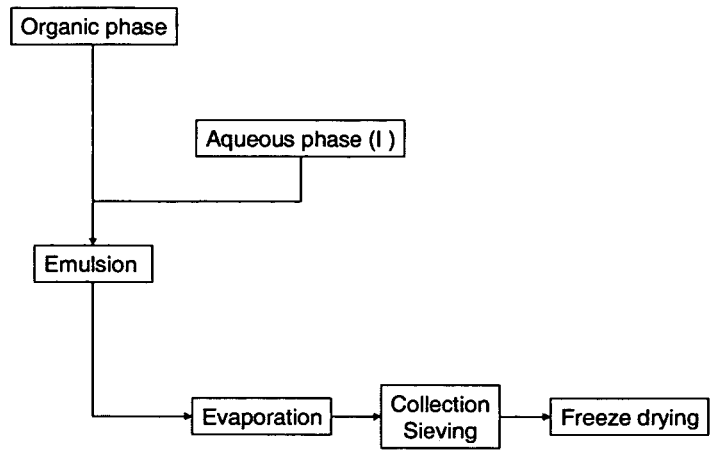
Figure 22  Classic emulsion/evaporation process for making active agent microspheres
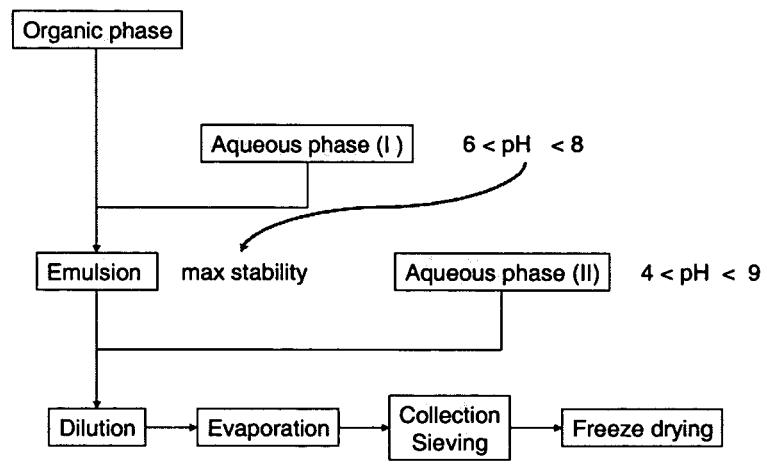
Figure 23

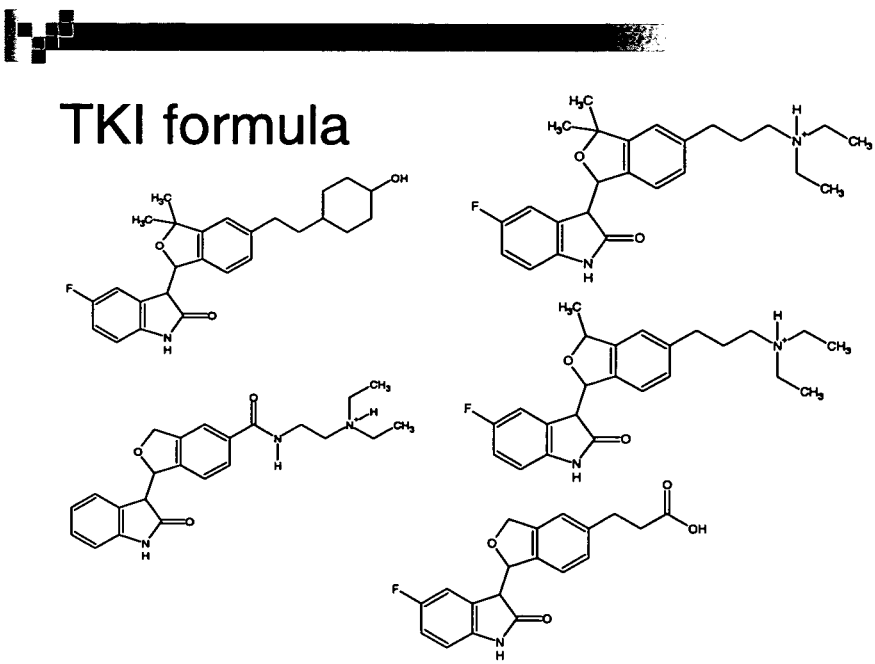
Figure 24
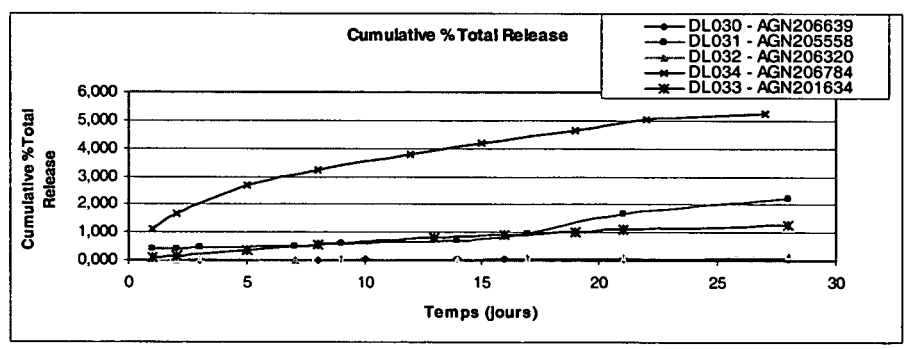
Figure 25 *In vitro* release profiles for the Five TKI Microspheres

TYROSINE KINASE MICROSPHERES

CROSS REFERENCE

This application is a continuation in part of application Ser. No. 10/837,361 filed Apr. 30, 2004, the entire content of which is incorporated herein by reference.

BACKGROUND

The present invention generally relates to devices and methods to treat an eye of a patient, and more specifically to intraocular implants that provide extended release of a therapeutic agent to an eye in which the implant is placed, and to methods of making and using such implants, for example, to treat or reduce one or more symptoms of an ocular condition.

Delivery of drugs to the retina, vitreous and uveal tract is typically achieved by high systemic dosing, intra-ocular injections or other heroic measures. Penetration of systemically administered drugs into the retina is severely restricted by the blood-retinal barriers (BRB) for most compounds. Although intraocular injection, such as intravitreal injections, resolves some constraints posed by the BRB and significantly reduces the risk of systemic toxicity, intraocular injection techniques may result in retinal detachment, physical damage to the lens, exogenous endophthalmitis, and also may result in high pulsed concentrations of drug at the lens and other intraocular tissues.

Compounds are eliminated from the vitreous by diffusion to the retro-zonular space with clearance via the aqueous humor or by trans-retinal elimination. Most compounds utilize the former pathway while lipophilic compounds and those with trans-retinal transport mechanisms will utilize the latter. Unfortunately, compounds that are eliminated across the retina have extremely short half-lives. Hence, for these compounds it is difficult to maintain therapeutic concentrations by direct intraocular injection, and therefore, frequent injection is often required.

Additionally, the rapid elimination of retinally cleared compounds makes formulation of controlled delivery systems challenging. For example, tyrosine kinase inhibitors (TKIs) may possess extremely short intraocular half-lives, and thus, may pose a challenge to the formulation of controlled delivery systems. The inventors are unaware of any small molecule TKIs given by intraocular administration, let alone, intraocular implants containing TKIs.

U.S. Pat. No. 6,713,081 discloses ocular implant devices made from polyvinyl alcohol and used for the delivery of a therapeutic agent to an eye in a controlled and sustained manner. The implants may be placed subconjunctivally or intravitreally in an eye.

Biocompatible implants for placement in the eye have also been disclosed in a number of patents, such as U.S. Pat. Nos. 4,521,210; 4,853,224; 4,997,652; 5,164,188; 5,443,505; 5,501,856; 5,766,242; 5,824,072; 5,869,079; 6,074,661; 6,331,313; 6,369,116; and 6,699,493.

It would be advantageous to provide eye implantable drug delivery systems, such as intraocular implants, and methods of using such systems, that are capable of releasing a therapeutic agent at a sustained or controlled rate for extended periods of time and in amounts with few or no negative side effects.

SUMMARY

The present invention provides new drug delivery systems, and methods of making and using such systems, for extended or sustained drug release into an eye, for example, to achieve one or more desired therapeutic effects. The drug delivery systems are in the form of implants or implant elements that may be placed in an eye. The present systems and methods advantageously provide for extended release times of one or more therapeutic agents. Thus, the patient in whose eye the implant has been placed receives a therapeutic amount of an agent for a long or extended time period without requiring additional administrations of the agent. For example, the patient has a substantially consistent level of therapeutically active agent available for consistent treatment of the eye over a relatively long period of time, for example, on the order of at least about one week, such as between about one and about six months or even for more than one year after receiving an implant. Such extended release times facilitate obtaining successful treatment results. The implants allow for prolonged delivery of a therapeutic agent while reducing invasive procedures and reducing high transient concentrations associated with pulsed dosing.

DEFINITIONS

The following terms as defined as follows, unless the context of the word indicates a different meaning.

As used herein, an "intraocular implant" refers to a device or element that is structured, sized, or otherwise configured to be placed in an eye. Intraocular implants are generally biocompatible with physiological conditions of an eye and do not cause adverse side effects. Intraocular implants may be placed in an eye without disrupting vision of the eye. The term "implant" includes "microimplant" or synonymously, "microsphere".

"Microimplants" or "microspheres" refers to implants having a sufficiently small cross-sectional area that they can be delivered according to methods that result in self-sealing of the eye at the puncture site associated with the delivery. In particular, such microimplants have dimensions such that they are deliverable through 20 gauge, 21 gauge or 22 gauge or smaller sized cannulas. Thin wall versions of 21 gauge needles can be manufactured having inner diameters of up to 0.028 inches, thus cylindrical microimplants deliverable through such cannulas will have outer diameters of less than 0.028 inches. Microimplants can also have non-circular cross-sectional geometries for delivery through cannulas having corresponding cross-sectional geometries. Where the micro-implant has non-circular cross-section, the cross-sectional area may be up to 0.00025 square inches or more, depending on the particular cross-sectional geometry. Implants, including microimplants, may be understood to comprise relatively smaller units of one or more active ingredients. For example, an implant may comprise a population of particles of an active ingredient. As used herein, particles may have any shape and are smaller in size than an implant that is administered to a patient to treat an ocular condition. In contrast to liquid ophthalmic compositions, the present implants are substantially solid, at least initially, before administration to a patient in need of ocular therapy. Microimplants within the scope of the present invention include those set forth in U.S. patent application Ser. No. 11/070,158, filed Mar. 1, 2005.

As used herein, a "therapeutic component" refers to a portion of an intraocular implant comprising one or more therapeutic agents or substances used to treat a medical condition of the eye. The therapeutic component may be a discrete region of an intraocular implant, or it may be homogenously distributed throughout the implant. The therapeutic agents of the therapeutic component are typically ophthalmically acceptable, and are provided in a form that does not cause adverse reactions when the implant is placed in an eye.

As used herein, a "drug release sustaining component" refers to a portion of the intraocular implant that is effective to provide a sustained release of the therapeutic agents of the implant. A drug release sustaining component may be a biodegradable polymer matrix, or it may be a coating covering a core region of the implant that comprises a therapeutic component.

As used herein, "associated with" means mixed with, dispersed within, coupled to, covering, or surrounding.

As used herein, an "ocular region" or "ocular site" refers generally to any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eyeball in an ocular region include the anterior chamber, the posterior chamber, the vitreous cavity, the choroid, the suprachoroidal space, the conjunctiva, the subconjunctival space, the episcleral space, the intracorneal space, the epicorneal space, the sclera, the pars plana, surgically-induced avascular regions, the macula, and the retina.

As used herein, an "ocular condition" is a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

An "anterior ocular condition" is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the retina but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A "posterior ocular condition" is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site.

Thus, a posterior ocular condition can include a disease, ailment or condition, such as for example, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic ophthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

The term "biodegradable polymer" refers to a polymer or polymers which degrade in vivo, and wherein erosion of the polymer or polymers over time occurs concurrent with or subsequent to release of the therapeutic agent. Specifically, hydrogels such as methylcellulose which act to release drug through polymer swelling are specifically excluded from the term "biodegradable polymer". The terms "biodegradable" and "bioerodible" are equivalent and are used interchangeably herein. A biodegradable polymer may be a homopolymer, a copolymer, or a polymer comprising more than two different polymeric units.

The term "treat", "treating", or "treatment" as used herein, refers to reduction or resolution or prevention of an ocular condition, ocular injury or damage, or to promote healing of injured or damaged ocular tissue.

The term "therapeutically effective amount" as used herein, refers to the level or amount of agent needed to treat an ocular condition, or reduce or prevent ocular injury or damage without causing significant negative or adverse side effects to the eye or a region of the eye.

Intraocular implants in accordance with the disclosure herein comprise a therapeutic component and a drug release sustaining component associated with the therapeutic component. The implants may be solid, semisolid, or viscoelastic. In accordance with the present invention, the therapeutic component comprises, consists essentially of, or consists of, a tyrosine kinase inhibitor (TKI), for example, an agent or compound that inhibits or reduces the activity of tyrosine kinase. The TKI may also be understood to be a small molecule TKI. The drug release sustaining component is associated with the therapeutic component to sustain release of an amount of the TKI into an eye in which the implant is placed. TKIs may be released from the implant by diffusion, erosion, dissolution or osmosis. The drug release sustaining component may comprise one or more biodegradable polymers or one or more non-biodegradable polymers. Examples of biodegradable polymers of the present implants may include poly-lactide-co-glycolide (PLGA and PLA), polyesters, poly (ortho ester), poly(phosphazine), poly(phosphate ester), polycaprolactone, natural polymers such as gelatin or collagen, or polymeric blends. The amount of the TKI is released into the eye for a period of time greater than about one week after the implant is placed in the eye and is effective in reducing or treating an ocular condition.

In one embodiment, the intraocular implants comprise a TKI and a biodegradable polymer matrix. The TKI is associated with a biodegradable polymer matrix that degrades at a rate effective to sustain release of an amount of the TKI from the implant effective to treat an ocular condition. The intraocular implant is biodegradable or bioerodible and provides a sustained release of the TKI in an eye for extended periods of time, such as for more than one week, for example for about one month or more and up to about six months or more. The implants may be configured to provide release of the therapeutic agent in substantially one direction, or the implants may provide release of the therapeutic agent from all surfaces of the implant.

The biodegradable polymer matrix of the foregoing implants may be a mixture of biodegradable polymers or the matrix may comprise a single type of biodegradable polymer. For example, the matrix may comprise a polymer selected from the group consisting of polylactides, poly(lactide-co-glycolides), polycaprolactones, and combinations thereof.

In another embodiment, intraocular implants comprise a therapeutic component that comprises a TKI, and a polymeric outer layer covering the therapeutic component. The polymeric outer layer includes one or more orifices or openings or holes that are effective to allow a liquid to pass into the implant, and to allow the TKI to pass out of the implant. The therapeutic component is provided in a core or interior portion of the implant, and the polymeric outer layer covers or coats the core. The polymeric outer layer may include one or more non-biodegradable portions. The implant can provide an extended release of the TKI for more than about two months, and for more than about one year, and even for more than about five or about ten years. One example of such a polymeric outer layer covering is disclosed in U.S. Pat. No. 6,331,313.

Advantageously, the present implants provide a sustained or controlled delivery of therapeutic agents at a maintained level despite the rapid elimination of the TKIs from the eye. For example, the present implants are capable of delivering therapeutic amounts of a TKI for a period of at least about 30 days to about a year despite the short intraocular half-lives associated with TKIs. Plasma TKI levels obtained after implantation are extremely low, thereby reducing issues or risks of systemic toxicity. The controlled delivery of the TKIs from the present implants permits the TKIs to be administered into an eye with reduced toxicity or deterioration of the blood-aqueous and blood-retinal barriers, which may be associated with intraocular injection of liquid formulations containing TKIs.

A method of making the present implants involves combining or mixing the TKI with a biodegradable polymer or polymers. The mixture may then be extruded or compressed to form a single composition. The single composition may then be processed to form individual implants suitable for placement in an eye of a patient.

Another method of making the present implants involves providing a polymeric coating around a core portion containing a TKI, wherein the polymeric coating has one or more holes.

The implants may be placed in an ocular region to treat a variety of ocular conditions, such as treating, preventing, or reducing at least one symptom associated with non-exudative age related macular degeneration, exudative age related macular degeneration, choroidal neovascularization, acute macular neuroretinopathy, cystoid macular edema, diabetic macular edema, Behcet's disease, diabetic retinopathy, retinal arterial occlusive disease, central retinal vein occlusion, uveitic retinal disease, retinal detachment, trauma, conditions caused by laser treatment, conditions caused by photodynamic therapy, photocoagulation, radiation retinopathy, epiretinal membranes, proliferative diabetic retinopathy, branch retinal vein occlusion, anterior ischemic optic neuropathy, non-retinopathy diabetic retinal dysfunction, retinitis pigmentosa, ocular tumors, ocular neoplasms, and the like.

Kits in accordance with the present invention may comprise one or more of the present implants, and instructions for using the implants. For example, the instructions may explain how to administer the implants to a patient, and types of conditions that may be treated with the implants.

Our invention also includes a biodegradable intravitreal implant comprising: a plurality of biodegradable polymer microspheres encapsulating a tyrosine kinase inhibitor (TKI), the microspheres releasing the TKI at a rate effective to sustain release of the TKI from the microspheres for at least about one week after the implant is placed in the vitreous of an eye. The polymer can be a polylactide, poly(lactide-co-glycolide), polycaprolactone, or a derivative thereof, or a mixture thereof. By encapsulating it is meant that the active agent is associated with, dispersed within, mixed with and/or embedded in the polymer.

The microspheres of this biodegradable intravitreal implant can release the TKI at a rate effective to sustain release of an amount of the TKI from the implant for more than one month from the time the implant is placed in the vitreous of the eye. The TKI can be present in the implant (i.e. the plurality of microspheres) in an amount of from about 40% by weight to about 60% by weight of the implant, and the biodegradable polymer matrix can comprise a poly(lactide-co-glycolide) in an amount from about 40% by weight to about 60% by weight of the implant.

Our invention also encompasses a process for making biodegradable active agent microspheres by:
(a) preparing an organic phase, which comprises, an active agent, a biodegradable polymer, and a solvent for the active agent and the polymer;
(b) preparing a first aqueous phase;
(c) combining the organic and the aqueous phase to form an emulsion;
(d) preparing a second aqueous phase;
(e) adding the second aqueous phase to the emulsion to form a solution;
(f) stirring the solution, and;
(g) evaporating the solvent, thereby making biodegradable active agent microspheres. The organic phase can be a viscous fluid. This method can also have the step of crystallizing active agent in the organic phase and/or the further step of crystallizing active agent in the emulsion.

Preferably, the pH of the first aqueous phase is between about pH 6 and about pH 8 and the pH of the second aqueous phase is between about pH 4 and about pH 9.

A detailed process for making biodegradable active agent microspheres can have the steps of:
(a) preparing a viscous organic phase, which comprises, a TKI, a biodegradable PLGA (or PLA) polymer, and a solvent for the active agent and the PLGA (or PLA) polymer;
(b) crystallizing active agent in the viscous organic phase;
(c) preparing a first aqueous phase with a pH between about pH 6 and about pH 8;
(d) combining the organic and the aqueous phase to form an emulsion;
(e) crystallizing active agent in the emulsion;
(f) preparing a second aqueous phase with a pH between about pH 4 and about pH 9;
(g) adding the second aqueous phase to the emulsion to form a solution;
(h) stirring the solution, and;
(i) evaporating the solvent, thereby making biodegradable active agent microspheres. The active agent can be a TKI.

Finally, our invention also encompasses a method for treating an ocular condition of an eye of a patient by placing biodegradable intraocular microspheres into the vitreous of an eye of the patient, the microspheres comprising a TKI and a biodegradable polymer, wherein the microspheres degrades at a rate effective to sustain release of an amount of the TKI from the microspheres effective to treat the ocular condition. The ocular condition can be, for example, a retinal ocular, glaucoma or a proliferative vitreoretinopathy.

Each and every feature described herein, and each and every combination of two or more of such features, is included within the scope of the present invention provided that the features included in such a combination are not mutually inconsistent. In addition, any feature or combination of features may be specifically excluded from any embodiment of the present invention.

Additional aspects and advantages of the present invention are set forth in the following description and claims, particularly when considered in conjunction with the accompanying drawings.

DRAWINGS

FIG. 22 is a summary flow chart of a known process for making active agent microspheres.

FIG. 23 is a summary flow chart of a new process for making active agent microspheres.

FIG. 24 shows the chemical structures of five TKIs used as the active agents in biodegradable microspheres.

FIG. 25 is a graph of the cumulative in vitro % total TKI release profiles of five different TKI PLGA microimplant formulations in phosphate buffered saline release medium, pH 7.4, over a 28 day period.

DESCRIPTION

Figure 1:
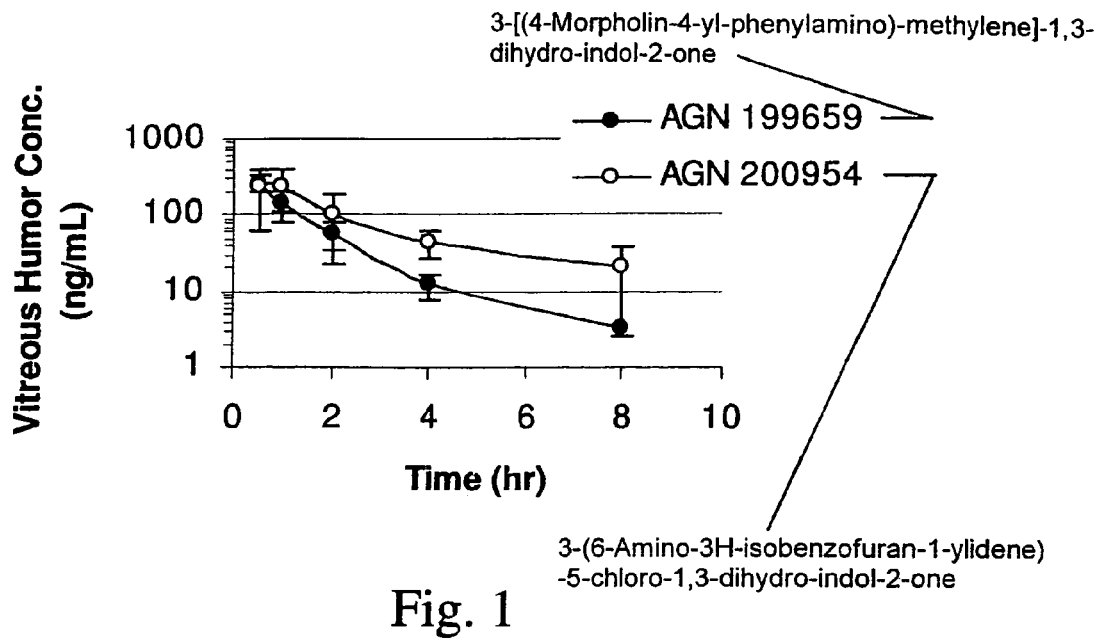
FIG. 1 is a graph showing the vitreous humor concentration of two TKIs as a function of time.

As described herein, controlled and sustained administration of a therapeutic agent through the use of one or more intraocular implants may improve treatment of undesirable ocular conditions. The implants comprise a pharmaceutically acceptable polymeric composition and are formulated to release one or more pharmaceutically active agents, such as tyrosine kinase inhibitors (TKIs), over an extended period of time. The implants are effective to provide a therapeutically effective dosage of the agent or agents directly to a region of the eye to treat, prevent, and/or reduce one or more symptoms of one or more undesirable ocular conditions. Thus, with a single administration, therapeutic agents will be made available at the site where they are needed and will be maintained for an extended period of time, rather than subjecting the patient to repeated injections or, in the case of self-administered drops, ineffective treatment with only limited bursts of exposure to the active agent or agents.

An intraocular implant in accordance with the disclosure herein comprises a therapeutic component and a drug release sustaining component associated with the therapeutic component. In accordance with the present invention, the therapeutic component comprises, consists essentially of, or consists of, a TKI. The drug release sustaining component is associated with the therapeutic component to sustain release of an effective amount of the therapeutic component into an eye in which the implant is placed. The amount of the therapeutic component is released into the eye for a period of time greater than about one week after the implant is placed in the eye, and is effective in treating and/or reducing at least one symptom of one or more ocular conditions, such as conditions wherein migration or proliferation of retinal pigment epithelium or glial cells causes or contributes to the cause of the condition. Some examples of ocular conditions that may be treated with the implants of the present invention include, without limitation, non-exudative age related macular degeneration, exudative age related macular degeneration, choroidal neovascularization, acute macular neuroretinopathy, cystoid macular edema, diabetic macular edema, Behcet's disease, diabetic retinopathy, retinopathy of prematurity, retinal arterial occlusive disease, central retinal vein occlusion, uveitic retinal disease, retinal detachment, trauma, conditions caused by laser treatment, conditions caused by photodynamic therapy, photocoagulation, radiation retinopathy, epiretinal membranes, proliferative diabetic retinopathy, branch retinal vein occlusion, anterior ischemic optic neuropathy, non-retinopathy diabetic retinal dysfunction, retinitis pigmentosa, ocular tumors, ocular neoplasms, and the like.

Intraocular implants have been developed which can release drug loads over various' time periods. These implants, which when inserted into an eye, such as the vitreous of an eye, provide therapeutic levels of a TKI, for extended periods of time (e.g., for about 1 week or more). The disclosed implants are effective in treating ocular conditions, such as non-exudative age related macular degeneration, exudative age related macular degeneration, choroidal neovascularization, acute macular neuroretinopathy, cystoid macular edema, diabetic macular edema, Behcet's disease, diabetic retinopathy, retinal arterial occlusive disease, central retinal vein occlusion, uveitic retinal disease, retinal detachment, trauma, conditions caused by laser treatment, conditions caused by photodynamic therapy, photocoagulation, radiation retinopathy, epiretinal membranes, proliferative diabetic retinopathy, branch retinal vein occlusion, anterior ischemic optic neuropathy, non-retinopathy diabetic retinal dysfunction, retinitis pigmentosa, ocular tumors, ocular neoplasms, and the like.

In one embodiment of the present invention, an intraocular implant comprises a biodegradable polymer matrix. The biodegradable polymer matrix is one type of a drug release sustaining component. The biodegradable polymer matrix is effective in forming a biodegradable intraocular implant. The biodegradable intraocular implant comprises a TKI associated with the biodegradable polymer matrix. The matrix degrades at a rate effective to sustain release of an amount of the TKI for a time greater than about one week from the time in which the implant is placed in ocular region or ocular site, such as the vitreous of an eye.

Microimplants prepared according to the present invention can be sufficiently small, or miniaturized, in size and shape such that they can be inserted into the eye without the necessity of an incision or puncture wound made in the eye that would normally require suturing or other surgical procedure to repair, as is typically the case when implanting larger implants. With the present microimplants, and according to insertion techniques further described below, the eye can "self-seal" after insertion of the microimplant, thereby eliminating the need for suturing or surgery, and the pain and trauma associated therewith, and also avoiding the costs, time and other inconveniences of performing such procedures in a surgical setting. As used herein, "self-sealing" methods of delivering microimplants into the eye refers to methods of introducing one or more microimplants through a cannula and into desired locations of a patient's eye without the need for a suture, or other like closure means, at the cannula puncture site. Such "self-sealing" methods do not require that the puncture site completely seal immediately upon withdrawal of the cannula, but rather that any initial leakage is minimal and dissipates in short order such that a surgeon or another person skilled in the art, in his or her good clinical judgment, would not be compelled to suture or otherwise provide other like closure means to the puncture site.

Both larger implants and smaller microimplants produced according to the present invention will have highly uniform characteristics and thus retain the ability to deliver precise and accurate dosage of the active ingredient, thereby providing for a highly controlled rate of release of the active ingredient into the eye over a specified time. The active ingredient released from the present implants may selectively target certain regions of the eye. For example, for implants placed in the posterior segment of an eye of a patient, the active ingredient may be released from the implant so that the active ingredient provides a therapeutic benefit to the retina, or a portion of the retina of the eye in which the implant is placed.

The present implants can be produced by combining particles of an active ingredient or ingredients and particles of a bioerodible polymer or polymers. According to particular processes, microimplants can be produced through a manufacturing process that includes sorting particles made of an active ingredient or ingredients and particles made of a bioerodible polymer or polymers according to size, blending these particles into a homogenous mixture of active ingredient(s) and bioerodible polymer(s), extruding (using a single or dual extrusion method) this mixture into filaments, precisely cutting these filaments into microimplants, and inspecting these microimplants for desired characteristics. This manufacturing process can be used to produce batches or populations of microimplants having the desired uniform characteristics, such as weight, dimensions (e.g., length, diameter, area, volume), regional distribution of active ingredients, release kinetics, and the like. For instance, these batches can be subjected to a specified acceptance criteria, including, e.g., a specified mass criteria, such as within a certain weight percentage of the desired target weight per microimplant, or e.g., a specified acceptable mass standard deviation for the microimplants of each batch. A specific drug/polymer ratio can also be obtained so that each individual implant of a batch or population of implants can contain the same amount of active ingredient. Thus, a batch of implants, such as a batch of implants in a package, may be provided with a specific label strength or dose of active ingredient for each individual implant of that batch.

Generally, implants and microimplants produced according to the invention can be formulated with a mixture of an active ingredient or ingredients and a bioerodible polymer or polymers, which can together control the release kinetics of the active ingredient into the eye. The particular formulations may vary according to the preferred drug release profile, the particular active ingredient or ingredients being used, the site of implantation, the condition being treated, and the medical history of the patient, for example. The present implants are formulated with particles of the active ingredient entrapped within the bioerodible polymer matrix. Release of the active ingredient or ingredients is achieved by erosion of the polymer followed by exposure of previously entrapped or dispersed active ingredient particles to the eye, and subsequent dissolution and release of agent. The parameters which determine the release kinetics include, but are not limited to, the size of the drug particles, the water solubility of the drug, the ratio of drug to polymer, the particular methods of manufacture, the shape of the implant, the surface area exposed, and the erosion rate of the polymer.

The TKI of the implant is typically an agent that inhibits or reduces the activity of a tyrosine kinase. The TKI may inhibit tyrosine kinase activity by directly acting on a tyrosine kinase molecule, or it may cooperate with one or more other factors or agents to achieve the desired inhibition. Examples of TKIs useful in the present implants are described in U.S. patent application Ser. No. 10/256,879 (U.S. Pub. No. 20030199478) and 10/259,703 (U.S. Pub. No. 20030225152).

In short, a TKI of the present implants include organic molecules capable of modulating, regulating and/or inhibiting tyrosine kinase signal transduction. Some compounds useful in the present implants are represented by the following formula

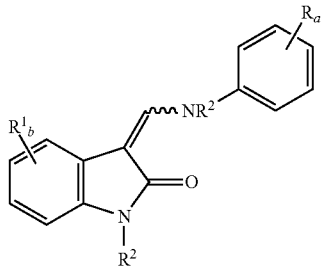

wherein $R^1$ is selected from the group consisting of halogen, $NO_2$, CN, $C_1$ to $C_4$ alkyl and aryl, e.g. phenyl; $R^2$ is selected from the group consisting of hydrogen, $C_1$ to $C_8$ alkyl, $COCH_3$, $CH_2CH_2OH$, $CH_2CH_2CH_2OH$ and phenyl; R is selected from the group consisting of D, halogen, $C_1$ to $C_8$ alkyl, $CF_3$, $OCF_3$, $OCF_2H$, $CH_2CN$, CN, $SR^2$, $(CR^7R^8)_cC(O)OR^2$, $C(O)N(R^2)_2$, $(CR^7R^8)_cOR^2$, $HNC(O)R^2$, HN—C(O)$OR^2$, $(CR^7R^8)_cN(R^2)_2$, $SO_2(CR^7R^8)_cN(R^2)_2$, $OP(O)(OR^2)_2$, $OC(O)OR^2$, $OCH_2O$, HN—CH=CH, —N(COR$^2$)CH$_2$CH$_2$, HC=N—NH, N=CH—S, $O(CR^7R^8)_d$—$R^6$ and $(CR^7R^8)_c$—$R^6$, —$NR^2(CR^7R^8)_dR^6$ wherein $R^6$ is selected from the group consisting of halogen, 3-fluoropyrrolidinyl, 3-fluoropiperidinyl, 2-pyridinyl, 3-pyridinyl, 4-pyridinyl, 3-pyrrolinyl, pyrrolidinyl, methyl isonipecotate, N-(2-methoxyethyl)-N-methylamyl, 1,2,3,6-tetrahydropyridinyl, morpholinyl, hexamethyleneiminyl, piperazinyl-2-one, piperazinyl, N-(2-methoxyethyl)ethylaminyl, thiomorpholinyl, heptamethyleneiminyl, 1-piperazinylcarboxaldehyde, 2,3,6,7-tetrahydro-(1H)-1,4-diazepinyl-5 (4H)-one, N-methylhomopiperazinyl, (3-dimethylamino)pyrrolidinyl, N-(2-methoxyethyl)-N-propylaminyl, isoindolinyl, nipecotamidinyl, isonipecotamidinyl, 1-acetylpiperazinyl, 3-acetamidopyrrolidinyl, trans-decahydroisoquinolinyl, cis-decahydroisoquinolinyl, N-acetylhomopiperazinyl, 3-(diethylamino)pyrrolidinyl, 1,4-dioxa-8-azaspiro[4.5]decaninyl, 1-(2-methoxyethyl)-piperazinyl, 2-pyrrolidin-3-ylpyridinyl, 4-pyrrolidin-3-ylpyridinyl, 3-(methylsulfonyl)pyrrolidinyl, 3-picolylmethylaminyl, 2-(2-methylaminoethyl)pyridinyl, 1-(2-pyrimidyl)-piperazinyl, 1-(2-pyrazinyl)-piperazinyl, 2-methylaminomethyl-1,3-dioxolane, 2-(N-methyl-2-aminoethyl)-1,3-dioxolane, 3-(N-acetyl-N-methylamino)pyrrolidinyl, 2-methoxyethylaminyl, tetrahydrofurfurylaminyl, 4-aminotetrahydropyran, 2-amino-1-methoxybutane, 2-methoxyisopropylaminyl, 1-(3-aminopropyl)imidazole, histamyl, N,N-diisopropylethylenediaminyl, 1-benzyl-3-aminopyrrolidyl 2-(aminomethyl)-5-methylpyrazinyl, 2,2-dimethyl-1,3-dioxolane-4-methanaminyl, (R)-3-amino-1-N—BOC-pyrrolidinyl, 4-amino-1,2,2,6,6-pentamethylpiperidinyl, 4-aminomethyltetrahydropyran, ethanolamine and alkyl-substituted derivatives thereof and wherein when c is 1 said $CH_2$ may be

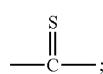

and $CH_2CH_2CH_2$; provided said alkyl or phenyl radicals may be substituted with one or two halo, hydroxy or lower alkyl amino radicals wherein $R^7$ and $R^8$ may be selected from the group consisting of H, F and $C_1$-$C_4$ alkyl or $CR^7R^8$ may represent a carbocyclic ring of from 3 to 6 carbons, preferably $R^7$ and $R^8$ are H or $CH_3$;

b is 0 or an integer of from 1 to 3;
a is 0 or an integer of from 1 to 5, preferably 1 to 3;
c is 0 or an integer of from 1 to 4,
d is an integer of from 2 to 5;
the wavy line represents a E or Z bond and pharmaceutically acceptable salts thereof.

In certain implants, the TKI is a compound having the foregoing formula, wherein $R^1$ is selected from the group consisting of H, i.e. b is 0; $CH_3$, F, Cl and phenyl.

Preferably, R is selected from the group consisting of $CH_3$, $CH_2CH_3$, $OCH_3$, OH, t-butyl, F, CN, $C(O)NH_2$, HNC(O)$CH_3$, $CH_2C(O)OH$, $SO_2NH_2$, C(O)OH, $OCF_2H$, isopropyl, $C_2H_5OH$, $C(O)OCH_3$, $CH_2OH$, NH—CH=CH, HC=N—N—H, N=CH—S, $O(CR^7R^8)_dR^6$, $(CR^7R^8)_cR^6$ and —$NR^2(CR^7R^8)_dR^6$, wherein $R^6$ is selected from the group consisting of 3-fluoropyrrolidinyl, 3-fluoropiperidinyl, 2-pyridinyl, 3-pyridinyl, 4-pyridinyl, 3-pyrrolinyl, pyrrolidinyl, methyl isonipecotate, N-(2-methoxyethyl)-N-methylamyl, 1,2,3,6-tetrahydropyridinyl, morpholinyl, hexamethyleneiminyl, piperazinyl-2-one, piperazinyl, N-(2-methoxyethyl)ethylaminyl, thiomorpholinyl, heptamethyleneiminyl, 1-piperazinylcarboxaldehyde, 2,3,6,7-tetrahydro-(1H)-1,4-diazepinyl-5 (4H)-one, N-methylhomopiperazinyl, (3-dimethylamino)pyrrolidinyl, N-(2-methoxyethyl)-N-propylaminyl, isoindolinyl, nipecotamidinyl, isonipecotamidinyl, 1-acetylpiperazinyl, 3-acetamidopyrrolidinyl, trans-decahydroisoquinolinyl, cis-decahydroisoquinolinyl, N-acetylhomopiperazinyl, 3-(diethylamino)pyrrolidinyl, 1,4-dioxa-8-azaspiro[4.5]decaninyl, 1-(2-methoxyethyl)-piperazinyl, 2-pyrrolidin-3-ylpyridinyl, 4-pyrrolidin-3-ylpyridinyl, 3-(methylsulfonyl)pyrrolidinyl, 3-picolylmethylaminyl, 2-(2-methylaminoethyl)pyridinyl, 1-(2-pyrimidyl)-piperazinyl, 1-(2-pyrazinyl)-piperazinyl, 2-methylaminomethyl-1,3-dioxolane, 2-(N-methyl-2-aminoethyl)-1,3-dioxolane, 3-(N-acetyl-N-methylamino)pyrrolidinyl, 2-methoxyethylaminyl, tetrahydrofurfurylaminyl, 4-aminotetrahydropyran, 2-amino-1-methoxybutane, 2-methoxyisopropylaminyl, 1-(3-aminopropyl)imidazole, histamyl, N,N-diisopropylethylenediaminyl, 1-benzyl-3-aminopyrrolidyl 2-(aminomethyl)-5-methylpyrazinyl, 2,2-dimethyl-1,3-dioxolane-4-methanaminyl, (R)-3-amino-1-N—BOC-pyrrolidinyl, 4-amino-1,2,2,6,6-pentamethylpiperidinyl, 4-aminomethyltetrahydropyranyl, ethanolamine and alkyl-substituted derivatives thereof, e.g. $R^6$ is morpholinyl or $CH_2N(CH_3)_2$.

More preferably, R is selected from the group consisting of m-ethyl, p-methoxy, p-hydroxy, m-hydroxy, p-cyano, m-C(O)NH$_2$, p-HNC(O)CH$_3$, p-CH$_2$C(O)OH, p-SO$_2$NH$_2$, p-CH$_2$OH, m-methoxy, p-CH$_2$CH$_2$OH, HNCH=CH, HC=N—NH, p-morpholinyl, N=CH—S, p-OCHF$_2$, p-COOH, p-CH$_3$, p-OCH$_3$, m-F, m-CH$_2$N(C$_2$H$_3$)$_2$, $(CR^7R^8)_cR^6$, $O(CR^7R^8)_dR^6$ and $NR^2(CR^7R^8)_dR^6$.

It is noted that R may represent a condensed ring that is attached to the above phenyl ring at two positions. For example, $CH_2CH_2CH_2$ may be attached at the 3 and 4 (or m and p) positions of the phenyl ring.

Still more preferably, R is selected from the group consisting of fluoro, methyl, $(CR^7R^8)_cR^6$, $O(CR^7R^8)_dR^6$ and $NR^2(CR^7R^8)_dR^6$ wherein $R^6$ is selected from dimethylamino, diethylamino, 3-fluoropyrrolidinyl, 3-fluoropiperidinyl, 3-pyridinyl, 4-pyridinyl, pyrrolidinyl, morpholinyl, piperazinyl, heptamethyleneiminyl, tetrahydrofurfurylaminyl, 4-aminotetrahydropyranyl, N,N-diisopropylethylenediaminyl and 4-aminomethyltetrahydropyran.

In particular, the compounds of the present implants may be selected from the compounds of the tables below.

TABLE 1

Unsubstituted 4-Methyl & 5-Chloro 3-[(Substituted Phenylamino)-methylene]-1,3-dihydro-indol-2-ones.

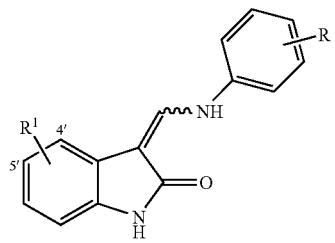

| Example # | $R^1$ | R Substitution 2 | 3 | 4 | 5 | 6 |
|---|---|---|---|---|---|---|
| 1 | H | H | H | H | H | H |
| 2 | H | H | Br | H | H | H |
| 3 | H | H | H | Br | H | H |
| 4 | H | Br | H | H | H | H |
| 5 | H | H | H | Et | H | H |
| 6 | H | H | Et | H | H | H |
| 7 | H | H | H | OMe | H | H |
| 8 | H | H | H | $CO_2Et$ | H | H |
| 9 | H | Et | H | H | H | H |
| 10 | H | H | F | Me | H | H |
| 11 | H | Me | F | H | H | H |
| 12 | H | H | H | OH | H | H |
| 13 | H | H | Cl | OH | H | H |
| 14 | H | Me | H | F | H | H |
| 15 | H | H | OH | H | H | H |
| 16 | H | H | OMe | H | OMe | H |
| 17 | H | H | H | tBu | H | H |
| 18 | H | H | H | Me | H | H |
| 19 | H | H | Me | H | Me | H |
| 20 | H | H | Me | Me | H | H |
| 21 | H | H | F | OMe | H | H |
| 22 | H | H | $CF_3$ | H | H | H |
| 23 | H | H | —$CH_2CH_2CH_2$— | | H | H |
| 24 | H | F | H | Cl | H | H |
| 25 | H | H | H | $CF_3$ | H | H |
| 26 | H | F | H | Me | $OCO_2Et$ | H |
| 27 | H | F | H | Me | $OCO_2CH_2C(CH_3)_3$ | H |
| 28 | H | F | H | Cl | OH | H |
| 29 | H | H | H | CN | H | H |
| 30 | H | H | H | $CH_2CN$ | H | H |
| 31 | H | H | —CH=CH—NH— | | H | H |
| 32 | H | H | —NH—N=CH— | | H | H |
| 33 | H | H | H | $CONH_2$ | H | H |
| 34 | H | H | H | $NHCOCH_3$ | H | H |
| 35 | H | H | $CH_2CO_2H$ | H | H | H |
| 36 | H | H | H | Cl | H | H |
| 37 | H | H | $CO_2H$ | Cl | H | H |
| 38 | H | H | H | $SO_2NH_2$ | H | H |
| 39 | H | H | H | $SO_2NHCOCH_3$ | H | H |
| 40 | H | H | H | N-morpholino | H | H |
| 41 | H | H | H | OPh | H | H |
| 42 | H | H | OMe | OMe | H | H |
| 43 | H | H | —S—CH=N— | | H | H |
| 44 | H | H | OH | $CO_2H$ | H | H |
| 45 | H | H | $CF_3$ | Cl | H | H |
| 46 | H | H | $CF_3$ | H | $CF_3$ | H |
| 47 | H | H | $CF_3$ | F | H | H |
| 48 | H | H | OH | Me | H | H |
| 49 | H | H | OH | OMe | H | H |
| 50 | H | H | H | $OCHF_2$ | H | H |
| 51 | H | H | H | $OCF_3$ | H | H |
| 52 | H | H | H | iPr | H | H |
| 53 | H | F | H | Me | H | H |
| 54 | H | H | Me | Cl | H | H |
| 55 | H | H | $CF_3$ | OMe | H | H |
| 56 | H | H | $CF_3$ | Me | H | H |
| 57 | 5'-Cl | H | OMe | H | H | H |

TABLE 1-continued

| | | | | | | |
|---|---|---|---|---|---|---|
| 58 | 4'-Me | H | H | H | H | H |
| 59 | 4'-Me | H | H | OMe | H | H |
| 60 | 4'-Me | H | OH | H | H | H |
| 61 | 4'-Me | H | OMe | H | OMe | H |
| 62 | 4'-Me | H | H | Me | H | H |
| 63 | 4'-Me | H | Me | H | Me | H |
| 64 | 5'-Cl | H | H | OCHF$_2$ | H | H |
| 65 | 5'-Cl | H | OH | OMe | H | H |
| 66 | 5'-Cl | H | H | OCF$_3$ | H | H |
| 67 | 5'-Cl | H | Me | OH | H | H |
| 68 | 5'-Cl | H | —OCH$_2$O— | | H | H |
| 69 | 5'-Cl | H | Me | Me | H | H |
| 70 | 5'-Cl | H | H | iPr | H | H |
| 71 | 5'-Cl | H | OH | Me | H | H |
| 72 | 5'-Cl | H | H | (CH$_2$)$_2$OH | H | H |
| 73 | 5'-Cl | H | H | OMe | H | H |
| 74 | 5'-Cl | H | H | H | H | H |
| 75 | 5'-Cl | H | OMe | H | OMe | H |
| 76 | 5'-Cl | H | OH | H | H | H |
| 77 | 5'-Cl | H | H | OH | H | H |
| 78 | 5'-Cl | H | Me | H | Me | H |
| 79 | 5'-Cl | H | H | Me | H | H |
| 80 | H | H | —OCH$_2$O— | | H | H |
| 81 | H | H | CO$_2$H | OH | H | H |
| 82 | H | H | H | OEt | H | H |
| 83 | H | H | —N(COMe)—CH$_2$—CH$_2$— | | H | H |
| 84 | H | H | H | OPO(OH)$_2$ | H | H |
| 85 | H | H | CO$_2$H | CO$_2$H | H | H |
| 86 | H | H | H | CO$_2$H | H | H |
| 87 | H | H | H | (CH$_2$)$_2$OH | H | H |
| 88 | H | H | H | CH$_2$OH | H | H |
| 89 | H | H | OMe | CO$_2$CH$_3$ | H | H |
| 90 | 4'-Me | H | —NH—N=CH— | | H | H |
| 91 | 4'-Me | H | F | OMe | H | H |
| 92 | 4'-Me | H | —S—CH=N— | | H | H |
| 93 | 4'-Me | H | OMe | CO$_2$CH$_3$ | H | H |
| 94 | H | H | OMe | H | H | H |
| 95 | 4'-Me | H | Me | Me | H | H |
| 96 | 4'-Me | H | H | OH | H | H |
| 97 | 4'-Me | H | —CH=CH—NH— | | H | H |
| 98 | 4'-Me | H | H | t-Bu | H | H |
| 99 | 4'-Me | H | H | CH$_2$OH | H | H |
| 100 | 5'-Cl | H | H | t-Bu | H | H |
| 101 | 5'-Cl | H | —S—CH=N— | | H | H |
| 102 | 5'-Cl | H | OMe | OMe | H | H |
| 103 | 5'-Cl | H | —NH—N=CH— | | H | H |
| 104 | 5'-Cl | OMe | H | Cl | OMe | H |
| 105 | 5'-Cl | H | F | OMe | H | H |
| 106 | 5'-Cl | H | H | N-morpholino | H | H |
| 107 | 5'-Cl | H | H | OEt | H | H |
| 108 | 5'-Cl | H | CO$_2$H | OH | H | H |
| 109 | 5'-Cl | H | CH$_2$NEt$_2$ | OH | H | H |
| 110 | 5'-Cl | H | —CH=CH—NH— | | H | H |
| 111 | 5'-Cl | H | H | CH$_2$OH | H | H |
| 112 | 5'-Cl | H | Me | iPr | H | H |
| 113 | 4'-Me | H | H | CH$_2$CH$_2$OH | H | H |
| 114 | 5'-Cl | H | H | NHCOMe | H | H |
| 115 | 5'-Cl | H | H | CH$_2$CO$_2$H | H | H |
| 116 | 5'-Cl | H | H | SO$_2$NH$_2$ | H | H |
| 117 | 4'-Me | H | OH | OMe | H | H |
| 118 | 4'-Me | H | CO$_2$H | OH | H | H |
| 119 | 4'-Me | H | H | OCHF$_2$ | H | H |
| 120 | 4'-Me | H | H | OCF$_3$ | H | H |
| 121 | 4'-Me | H | CF$_3$ | OMe | H | H |
| 122 | 4'-Me | H | H | OEt | H | H |
| 123 | 4'-Me | H | H | iPr | H | H |
| 124 | 4'-Me | H | —O—CH$_2$—O— | | H | H |
| 125 | 4'-Me | H | OH | Me | H | H |
| 126 | 4'-Me | H | OMe | OMe | H | H |
| 127 | 4'-Me | Et | H | H | H | H |
| 128 | 4'-Me | H | H | CN | H | H |
| 129 | 4'-Me | H | H | CONH$_2$ | H | H |
| 130 | 4'-Me | H | H | NHCOCH$_3$ | H | H |
| 131 | 4'-Me | H | H | CH$_2$CO$_2$H | H | H |
| 132 | 4'-Me | H | Me | OH | H | H |
| 133 | H | H | Me | OH | H | H |
| 134 | H | H | OH | NHCO$_2$Et | H | H |
| 135 | 4'-Me | F | H | OMe | H | H |
| 136 | H | H | H | SMe | H | H |
| 137 | 4'-Me | H | H | SMe | H | H |

TABLE 1-continued

| | | | | | | |
|---|---|---|---|---|---|---|
| 138 | 5'-Cl | H | H | SMe | H | H |
| 139 | H | H | H | —CH₂CH₂CH₂CO₂H | H | H |
| 140 | 4'-Me | H | H | —CH₂CH₂CH₂CO₂H | H | H |
| 141 | H | H | —CH₂CH₂CO₂H | H | H | H |
| 142 | 4'-Me | H | —CH₂CH₂CO₂H | H | H | H |
| 143 | 5'-Cl | H | —CH₂CH₂CO₂H | H | H | H |
| 144 | H | H | H | —CH₂CH₂CO₂H | H | H |
| 145 | 4'-Me | H | H | —CH₂CH₂CO₂H | H | H |
| 146 | 5'-Cl | H | H | —CH₂CH₂CO₂H | H | H |

Unsubstituted, 4-methyl, 5-Chloro & 5-Fluoro 3-[(Substituted Phenylamino)-methylene]-1,3-dihydro-indol-2-ones.

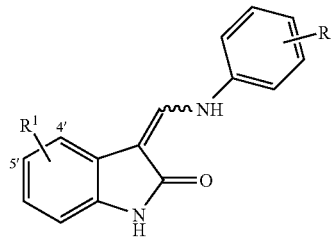

| Example # | R¹ | R Substitution | | | | |
|---|---|---|---|---|---|---|
| | | 2 | 3 | 4 | 5 | 6 |
| 147 | 4'-Me | H | Et | H | H | H |
| 148 | 5'-Cl | H | Et | H | H | H |
| 149 | 5'-Cl | H | H | Et | H | H |
| 150 | 5'-Cl | H | H | —CH₂CH₂CH₂CO₂H | H | H |
| 151 | 4'-Me | H | H | Et | H | H |
| 152 | 5'-Cl | H | H | —CN | H | H |
| 155 | 4'-Me | H | OH | CO₂H | H | H |
| 156 | H | H | H | N(Me)₂ | H | H |
| 157 | H | H | H | ⟨N-piperazinyl-NMe⟩ | H | H |
| 158 | H | H | H | ⟨N-piperidinyl⟩ | | H |
| 159 | H | H | H | ⟨2,6-dimethylmorpholinyl⟩ | H | H |
| 160 | H | H | CH₂N(Et)₂ | OH | H | H |
| 161 | 4'-Me | H | CH₂N(Et)₂ | OH | H | H |
| 162 | 5'-F | H | —CH=CH—NH— | | H | H |
| 163 | 5'-F | H | —NH—N=CH— | | H | H |
| 164 | 5'-F | H | OH | OMe | H | H |
| 165 | 5'-F | H | H | CH₂CH₂CO₂H | H | H |
| 166 | 5'-F | H | H | SO₂NH₂ | H | H |
| 167 | 5'-F | H | H | ⟨N-morpholinyl⟩ | H | H |
| 168 | 5'-F | H | H | ⟨N-piperazinyl-NMe⟩ | H | H |
| 169 | 5'-F | H | H | H | H | H |
| 170 | 5'-F | H | H | CONH₂ | H | H |
| 171 | 5'-F | H | H | SMe | H | H |

TABLE 1-continued

| | | | | | | |
|---|---|---|---|---|---|---|
| 172 | 5'-F | H | F | OMe | H | H |
| 173 | 5'-F | H | —S—CH=N— | | H | H |
| 174 | 5'-F | H | H | CH$_2$CO$_2$H | H | H |
| 175 | 5'-F | H | CH$_2$CH$_2$CO$_2$H | H | H | H |
| 176 | 5'-F | H | Et | H | H | H |
| 177 | 5'-F | H | OH | H | H | H |
| 178 | 5'-F | H | H | CH$_2$OH | H | H |
| 179 | H | H | H | 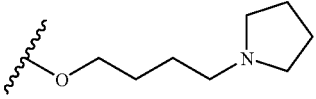 [SMILES: *OCCCCN1CCCC1] | H | H |
| 180 | H | H | H | NH$_2$ | H | H |
| 181 | 4'-Me | H | H | NH$_2$ | H | H |
| 182 | H | H | CH(OH)CH$_3$ | H | H | H |
| 183 | 4'-Me | H | CH(OH)CH$_3$ | H | H | H |
| 184 | H | H | CH$_2$OH | H | H | H |
| 185 | 4'-Me | H | CH$_2$OH | H | H | H |
| 186 | H | H | NHCO$_2$t-Bu | H | H | H |
| 187 | 4'-Me | H | NHCO$_2$t-Bu | H | H | H |
| 188 | H | H | H | N(Et)$_2$ | H | H |
| 189 | 4'-Me | H | H | N(Et)$_2$ | H | H |
| 190 | H | H | SO$_2$N(CH$_2$CH$_2$OH)$_2$ | H | H | H |
| 191 | 4'-Me | H | SO$_2$N(CH$_2$CH$_2$OH)$_2$ | H | H | H |
| 192 | H | H | H | SO$_2$NCH$_2$CH$_2$OH | H | H |
| 193 | H | H | SO$_2$NCH$_2$CH$_2$CH$_2$OH | H | H | H |
| 194 | 4'-Me | H | SO$_2$NCH$_2$CH$_2$CH$_2$OH | H | H | H |
| 195 | H | H | CO$_2$H | 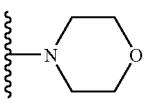 [SMILES: *N1CCOCC1] | H | H |
| 196 | 4'-Me | H | H | 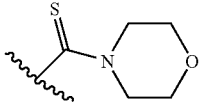 [SMILES: *C(=S)N1CCOCC1] | H | H |
| 197 | 4'-Me | H | H | SO$_2$NCH$_2$CH$_2$OH | H | H |
| 198 | H | H | H | OCH$_2$CH$_2$CH$_2$Cl | H | H |
| 199 | H | H | H | OCH$_2$CH$_2$CH$_2$CH$_2$Cl | H | H |
| 200 | H | H | H | OCH$_2$CH$_2$CH$_2$I | H | H |
| 201 | H | H | H | OCH$_2$CH$_2$CH$_2$CH$_2$I | H | H |
| 202 | 4'-Me | D | D | D | D | D |
| 203 | H | D | D | CO$_2$H | D | D |
| 204 | H | D | D | NH$_2$ | D | D |
| 205 | 4'-Me | D | D | NH$_2$ | D | D |
| 206 | H | H | H | 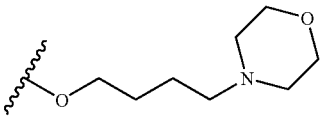 [SMILES: *OCCCCN1CCOCC1] | H | H |
| 207 | H | H | H | OCH$_2$CH$_2$CH$_2$CH$_2$N(Et)$_2$ | H | H |
| 208 | H | H | H | 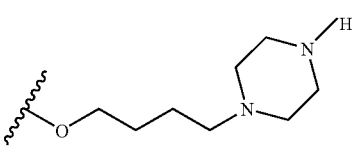 | H | H |
| 209 | H | H | H | 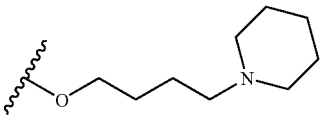 [SMILES: *OCCCCN1CCCCC1] | H | H |
| 210 | 4-Me | H | NH$_2$ | H | H | H |
| 211 | H | H | NH$_2$ | H | H | H |
| 212 | H | H | NH$_2$ | Me | H | H |
| 213 | 4-Me | H | NH$_2$ | Me | H | H |
| 214 | H | H | H | OCH$_2$CH$_2$CH$_2$N(Et)$_2$ | H | H |

TABLE 1-continued

| | | | | 4 | | |
|---|---|---|---|---|---|---|
| 215 | H | H | H | O-CH2CH2CH2-morpholine | H | H |
| 216 | H | H | H | O-CH2CH2CH2-pyrrolidine | H | H |
| 217 | H | H | H | O-CH2CH2CH2-(N-methylpiperazine) | H | H |
| 218 | H | H | H | O-CH2CH2CH2-piperidine | H | H |
| 219 | 5'-F | H | H | N-(2,6-dimethylmorpholine) | H | H |
| 220 | 4'-Me | H | H | N-(2,6-dimethylmorpholine) | H | H |

Unsubstituted, 4-Fluoro, 4-methyl, 5-Chloro, 5-Cyano, 5-Fluoro, 5-Nitro, 6-Fluoro & 6-Aryl 3-[(Substituted Phenylamino)-methylene]-1,3-dihydro-indol-2-ones.

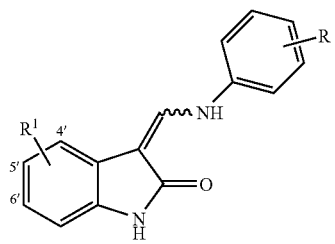

| Example # | R¹ | 2 | 3 | R Substitution 4 | 5 | 6 |
|---|---|---|---|---|---|---|
| 221 | 5'-F | H | H | N-piperidine | H | H |
| 222 | 5'-F | H | H | OMe | H | H |
| 223 | H | D | D | D | D | D |
| 224 | H | H | H | CH₂CO₂H | H | H |

TABLE 1-continued

| | | | | | | |
|---|---|---|---|---|---|---|
| 225 | H | H | H | ⟋O⟍⟋⟍⟋N(thiomorpholine) | H | H |
| 226 | H | H | H | ⟋O⟍⟋⟍⟋⟍N(thiomorpholine) | H | H |
| 227 | 4'-Me | H | H | N(morpholine) | H | H |
| 228 | 6'-F | H | H | N(morpholine) | H | H |
| 229 | 6'-F | H | H | N(2,6-dimethylmorpholine) | H | H |
| 230 | 6'-F | H | H | N(4-methylpiperazine) | H | H |
| 231 | 4'-Me | H | H | ⟋O⟍⟋⟍N(Et)₂ | H | H |
| 232 | 5'-Cl | H | H | ⟋O⟍⟋⟍N(Et)₂ | H | H |
| 233 | 5'-F | H | H | ⟋O⟍⟋⟍N(Et)₂ | H | H |
| 234 | 6'-F | H | H | ⟋O⟍⟋⟍N(Et)₂ | H | H |
| 235 | H | H | H | ⟋NH⟍⟋⟍N(morpholine) | H | H |
| 236 | 5'-NO₂ | H | H | N(morpholine) | H | H |

TABLE 1-continued
| 237 | 5'-CN | H | H | 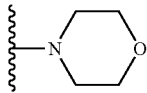 | H | H |
| --- | --- | --- | --- | --- | --- | --- |
| 238 | 4'-Me | H | H | 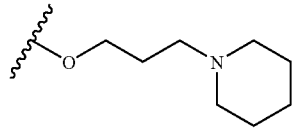 [SMILES: *OCCCN1CCCCC1] | H | H |
| 239 | 6'-F | H | H | 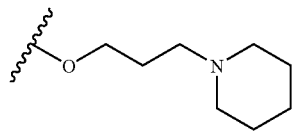 [SMILES: *OCCCN1CCCCC1] | H | H |
| 240 | 5'-F | H | H | 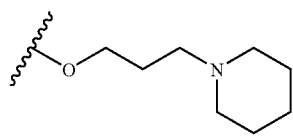 [SMILES: *OCCCN1CCCCC1] | H | H |
| 241 | 5'-Cl | H | H | 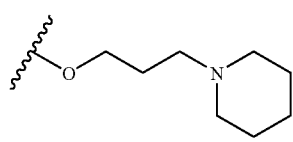 [SMILES: *OCCCN1CCCCC1] | H | H |
| 242 | 4'-Me | H | H | 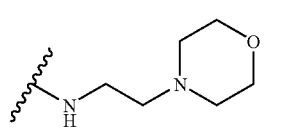 [SMILES: *NCCN1CCOCC1] | H | H |
| 243 | 6'-F | H | H | 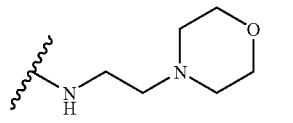 [SMILES: *NCCN1CCOCC1] | H | H |
| 244 | 5'-F | H | H | 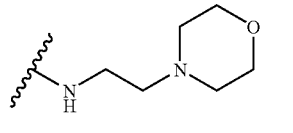 [SMILES: *NCCN1CCOCC1] | H | H |
| 245 | 5'-Cl | H | H | 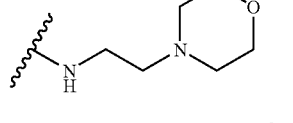 | H | H |
| 246 | 4'-Me | H | H | 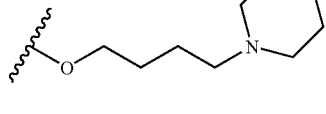 | H | H |
| 247 | 6'-F | H | H | 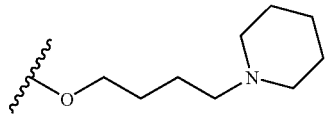 [SMILES: *OCCCCN1CCCCC1] | H | H |
| 248 | H | H | F | 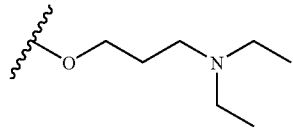 [SMILES: *OCCCN(CC)CC] | H | H |

TABLE 1-continued

| 249 | 4'-Me | H | F | ⸺O⸺CH₂CH₂CH₂⸺N(Et)₂ | H | H |
|---|---|---|---|---|---|---|
| 250 | 6'-F | H | F | ⸺O⸺CH₂CH₂CH₂⸺N(Et)₂ | H | H |
| 251 | H | H | H | ⸺CH₂-piperidinyl | H | H |
| 252 | 4'-Me | H | H | ⸺O⸺CH₂CH₂-piperidinyl | H | H |
| 253 | 6'-F | H | H | ⸺O⸺CH₂CH₂-piperidinyl | H | H |
| 254 | H | H | H | ⸺O⸺CH₂CH₂-piperidinyl | H | H |
| 255 | 4'-F | H | H | ⸺O⸺CH₂CH₂CH₂-piperidinyl | H | H |
| 256 | 4'-Me | H | H | ⸺CH₂-piperidinyl | H | H |
| 257 | 4'-F | H | H | ⸺CH₂-piperidinyl | H | H |
| 258 | 5'-F | H | H | ⸺CH₂-piperidinyl | H | H |
| 259 | 6'-F | H | H | ⸺CH₂-piperidinyl | H | H |
| 260 | 5'-Cl | H | H | ⸺CH₂-piperidinyl | H | H |

TABLE 1-continued
| 261 | 4'-F | H | H | 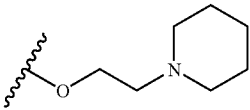 | H | H |
| --- | --- | --- | --- | --- | --- | --- |
| 262 | 5'-Cl | H | H | 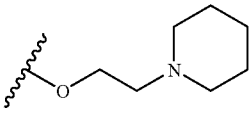 | H | H |
| 263 | 5'-F | H | H | 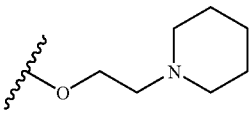 | H | H |
| 264 | 4'-Me | H | H | 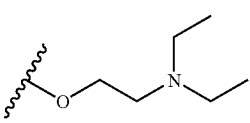 [SMILES: *OCCN(CC)CC] | H | H |
| 265 | H | H | H | 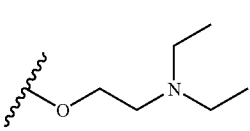 [SMILES: *OCCN(CC)CC] | H | H |
| 266 | 6'-F | H | H | 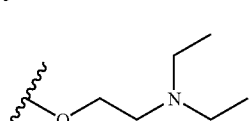 | H | H |
| 267 | 4'-F | H | H | 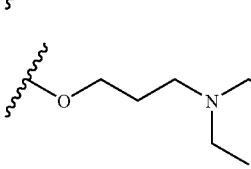 | H | H |
| 268 | 6'-(3-Methoxyphenyl) | H | H | 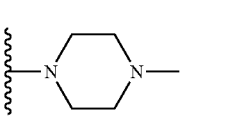 [SMILES: *N1CCN(C)CC1] | H | H |
| 269 | 6'-(3-Methoxyphenyl) | H | H | 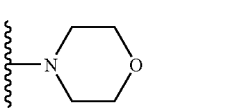 | H | H |
| 270 | 4'-Me | H | H | 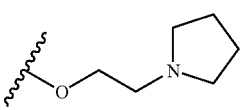 [SMILES: *OCCN1CCCC1] | H | H |
| 271 | 6'-F | H | H | 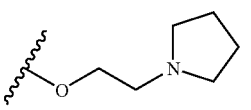 [SMILES: *OCCN1CCCC1] | H | H |
| 272 | H | H | H | 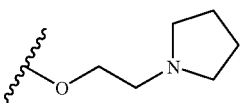 [SMILES: *OCCN1CCCC1] | H | H |
| 273 | 4'-F | H | H | 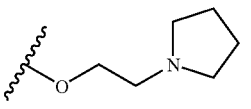 [SMILES: *OCCN1CCCC1] | H | H |

TABLE 1-continued
| 274 | 5'-F | H | H | 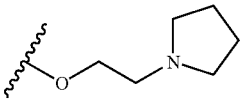 [SMILES: *OCCN1CCCC1] | H | H |
| --- | --- | --- | --- | --- | --- | --- |
| 275 | 5'-Cl | H | H | 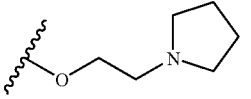 [SMILES: *OCCN1CCCC1] | H | H |
| 276 | 6'-(3-Methoxyphenyl) | H | H | 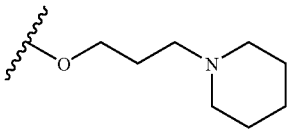 [SMILES: *OCCCN1CCCCC1] | H | H |
| 277 | 6'-(3-Methoxyphenyl) | H | H | 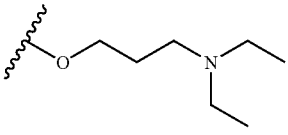 [SMILES: *OCCCN(CC)CC] | H | H |
| 278 | 4'-Me | H | H | 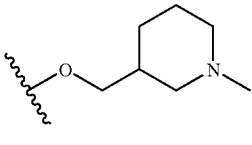 [SMILES: *OCC1CCCN(C)C1] | H | H |
| 279 | 6'-F | H | H | 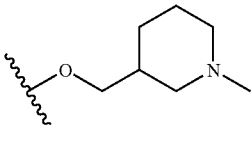 | H | H |
| 280 | H | H | H | 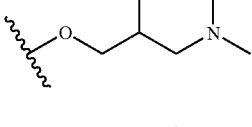 | H | H |
| 281 | 4'-F | H | H | 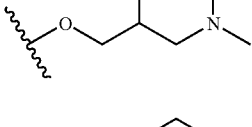 | H | H |
| 282 | 5'-F | H | H | 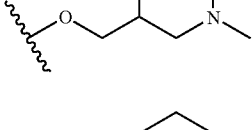 | H | H |
| 283 | 5'-Cl | H | H | 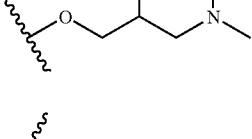 | H | H |
| 284 | H | H | H | 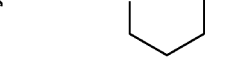 | H | H |

TABLE 1-continued

| | | | | | | |
|---|---|---|---|---|---|---|
| 285 | 5'-Cl | H | H | propyl-piperidine | H | H |
| 286 | 4'-Me | H | H | propyl-piperidine | H | H |
| 287 | 4'-F | H | H | propyl-piperidine | H | H |
| 288 | 5'-F | H | H | propyl-piperidine | H | H |
| 289 | 6'-F | H | H | propyl-piperidine | H | H |
| 290 | H | H | H | methyl-morpholine | H | H |
| 291 | 5'-Cl | H | H | methyl-morpholine | H | H |
| 292 | 4'-Me | H | H | methyl-morpholine | H | H |
| 293 | 4'-F | H | H | methyl-morpholine | H | H |
| 294 | 5'-F | H | H | methyl-morpholine | H | H |
| 295 | 6'-F | H | H | methyl-morpholine | H | H |

TABLE 1-continued
| | | | | | | | |
|---|---|---|---|---|---|---|---|
| 296 | 4'-Me | H | H | 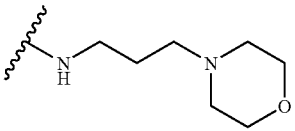 [SMILES: *NCCCN1CCOCC1] | | H | H |
| 297 | H | H | H | 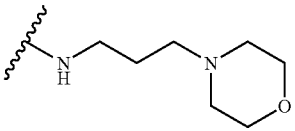 [SMILES: *NCCCN1CCOCC1] | | H | H |
| 298 | 6'-F | H | H | 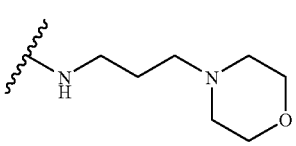 [SMILES: *NCCCN1CCOCC1] | | H | H |
| 299 | 5'-Cl | H | H | 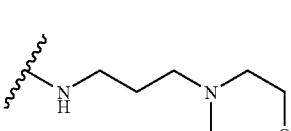 | | H | H |
| 300 | 5'-F | H | H | 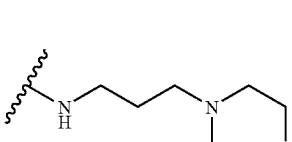 | | H | H |
| 301 | 4'-F | H | H | 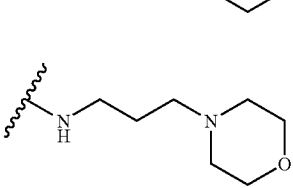 | | H | H |
| 302 | H | H | H |  | | H | H |
| 303 | 4'-Me | H | H | 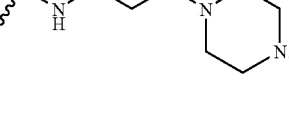 | | H | H |
| 304 | 6'-F | H | H | 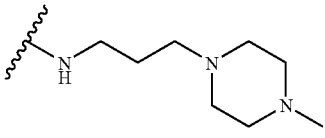 [SMILES: *NCCCN1CCN(C)CC1] | | H | H |

TABLE 1-continued

Unsubstituted, 4-Fluoro, 4-methyl, 5-Chloro, 5-Fluoro & 6-Fluoro 3-[(Substituted Phenylamino)-methylene]-1,3-dihydro-indol-2-ones.

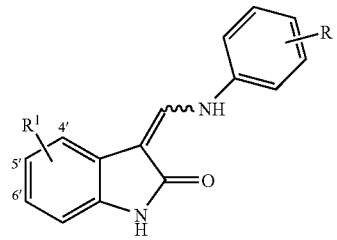

| Example # | R¹ | R Substitution | | | | |
|---|---|---|---|---|---|---|
| | | 2 | 3 | 4 | 5 | 6 |
| 305 | H | H | H | ~O~~~N(3-F-pyrrolidine) | H | H |
| 306 | H | H | H | ~~~N-morpholine (propyl linker) | H | H |
| 307 | 5'-Cl | H | H | ~~~N-morpholine (propyl linker) | H | H |
| 308 | 4'-Me | H | H | ~~~N-morpholine (propyl linker) | H | H |
| 309 | 4'-F | H | H | ~~~N-morpholine (propyl linker) | H | H |
| 310 | 5'-F | H | H | ~~~N-morpholine (propyl linker) | H | H |
| 311 | 6'-F | H | H | ~~~N-morpholine (propyl linker) | H | H |
| 312 | H | H | H | ~~~N-morpholine (butyl linker) | H | H |

TABLE 1-continued

| | | | | | | | |
|---|---|---|---|---|---|---|---|
| 313 | 5'-Cl | H | H | (CH₂)₄-morpholine | | H | H |
| 314 | 4'-Me | H | H | (CH₂)₄-morpholine | | H | H |
| 315 | 4'-F | H | H | (CH₂)₄-morpholine | | H | H |
| 316 | 5'-F | H | H | (CH₂)₄-morpholine | | H | H |
| 317 | 6'-F | H | H | (CH₂)₄-morpholine | | H | H |
| 318 | H | H | H | (CH₂)₄-piperidine | | H | H |
| 319 | 5'-Cl | H | H | (CH₂)₄-piperidine | | H | H |
| 320 | 4'-Me | H | H | (CH₂)₄-piperidine | | H | H |
| 321 | 4'-F | H | H | (CH₂)₄-piperidine | | H | H |
| 322 | 5'-F | H | H | (CH₂)₄-piperidine | | H | H |
| 323 | 6'-F | H | H | (CH₂)₄-piperidine | | H | H |

The present implants may also comprise a TKI or a combination of TKIs represented by the following formulas

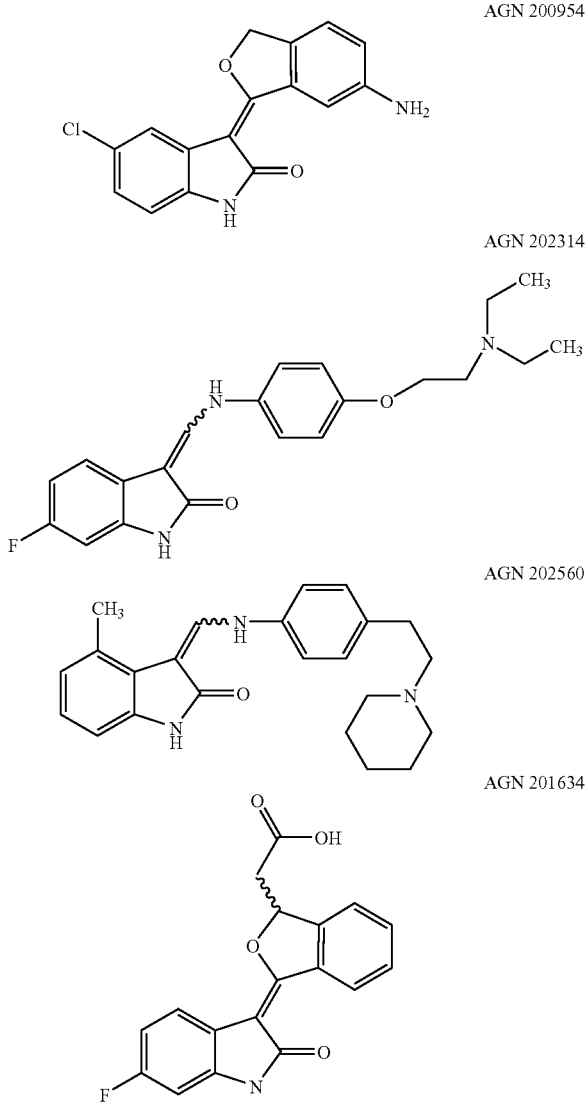

Additional TKIs that may be used in the present implants include those compounds disclosed in Goel et al., "Tyrosine Kinase Inhibitors: A Clinical Perspective", Current Oncology Reports, 4:9-19 (2002); Haluska et al., "Receptor tyrosine kinase inhibitors", Current Opinion in Investigational Drugs, 2(2):280-286 (2001); Hubbard et al., "Protein tyrosine kinase structure and function", Annu. Rev. Biochem., 69:373-98 (2000); Busse et al., "Tyrosine kinase inhibitors: rationale, mechanisms of action, and implications for drug resistance", Semin Oncol 28(suppl 16) 47-55 (2001); and Fabbro et al., "Protein tyrosine kinase inhibitors: new treatment modalities?", Current Opinion in Pharmacology, 2:374-381 (2002).

The foregoing compounds may be synthesized using routine chemical technologies and methods including those disclosed in U.S. patent application Ser. Nos. 10/256,879 (U.S. Pub. No. 20030199478) and 10/259,703 (U.S. Pub. No. 20030225152) and the other above-identified references.

The present implants may also include salts of the TKIs. Pharmaceutically acceptable acid addition salts of the compounds of the invention are those formed from acids which form non-toxic addition salts containing pharmaceutically acceptable anions, such as the hydrochloride, hydrobromide, hydroiodide, sulfate, or bisulfate, phosphate or acid phosphate, acetate, maleate, fumarate, oxalate, lactate, tartrate, citrate, gluconate, saccharate and p-toluene sulphonate salts.

Thus, the implant may comprise a therapeutic component which comprises, consists essentially of, or consists of a TKI, salts thereof, and mixtures thereof. The biodegradable polymer matrix of such implants may be substantially free of polyvinyl alcohol, or in other words, includes no polyvinyl alcohol.

Additional TKIs may be obtained or synthesized using conventional methods, such as by routine chemical synthesis methods known to persons of ordinary skill in the art. Therapeutically effective TKIs may be screened and identified using conventional screening technologies used for the TKIs described herein.

The TKIs may be in a particulate or powder form and entrapped by the biodegradable polymer matrix. Usually, TKI particles in intraocular implants will have an effective average size less than about 3000 nanometers. In certain implants, the particles may have an effective average particle size about an order of magnitude smaller than 3000 nanometers. For example, the particles may have an effective average particle size of less than about 500 nanometers. In additional implants, the particles may have an effective average particle size of less than about 400 nanometers, and in still further embodiments, a size less than about 200 nanometers.

The TKI of the implant is preferably from about 10% to 90% by weight of the implant. More preferably, the TKI is from about 20% to about 80% by weight of the implant. In a preferred embodiment, the TKI comprises about 40% by weight of the implant (e.g., 30%-50%). In another embodiment, the TKI comprises about 60% by weight of the implant.

Suitable polymeric materials or compositions for use in the implant include those materials which are compatible, that is biocompatible, with the eye so as to cause no substantial interference with the functioning or physiology of the eye. Such materials preferably are at least partially and more preferably substantially completely biodegradable or bioerodible.

Examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy, e.g. hydroxy or ether, carbonyl, e.g. non-oxo-carbonyl, such as carboxylic acid ester, and the like. The nitrogen may be present as amide, cyano and amino. The polymers set forth in Heller, Biodegradable Polymers in Controlled Drug Delivery, In: CRC Critical Reviews in Therapeutic Drug Carrier Systems, Vol. 1, CRC Press, Boca Raton, Fla. 1987, pp 39-90, which describes encapsulation for controlled drug delivery, may find use in the present implants.

Of additional interest are polymers of hydroxyaliphatic carboxylic acids, either homopolymers or copolymers, and polysaccharides. Polyesters of interest include polymers of D-lactic acid, L-lactic acid, racemic lactic acid, glycolic acid, polycaprolactone, and combinations thereof. Generally, by employing the L-lactate or D-lactate, a slowly eroding polymer or polymeric material is achieved, while erosion is substantially enhanced with the lactate racemate.

Among the useful polysaccharides are, without limitation, calcium alginate, and functionalized celluloses, particularly carboxymethylcellulose esters characterized by being water insoluble, a molecular weight of about 5 kD to 500 kD, for example.

Other polymers of interest include, without limitation, polyesters, polyethers and combinations thereof which are biocompatible and may be biodegradable and/or bioerodible.

Some preferred characteristics of the polymers or polymeric materials for use in the present invention may include biocompatibility, compatibility with the therapeutic component, ease of use of the polymer in making the drug delivery systems of the present invention, a half-life in the physiological environment of at least about 6 hours, preferably greater than about one day, not significantly increasing the viscosity of the vitreous, and water insolubility.

The biodegradable polymeric materials which are included to form the matrix are desirably subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, and whether the polymer includes terminal acid groups.

Equally important to controlling the biodegradation of the polymer and hence the extended release profile of the implant is the relative average molecular weight of the polymeric composition employed in the implant. Different molecular weights of the same or different polymeric compositions may be included in the implant to modulate the release profile. In certain implants, the relative average molecular weight of the polymer will range from about 9 to about 64 kD, usually from about 10 to about 54 kD, and more usually from about 12 to about 45 kD.

In some implants, copolymers of glycolic acid and lactic acid are used, where the rate of biodegradation is controlled by the ratio of glycolic acid to lactic acid. The most rapidly degraded copolymer has roughly equal amounts of glycolic acid and lactic acid. Homopolymers, or copolymers having ratios other than equal, are more resistant to degradation. The ratio of glycolic acid to lactic acid will also affect the brittleness of the implant, where a more flexible implant is desirable for larger geometries. The % of polylactic acid in the polylactic acid polyglycolic acid (PLGA) copolymer can be 0-100%, preferably about 15-85%, more preferably about 35-65%. In some implants, a 50/50 PLGA copolymer is used.

The biodegradable polymer matrix of the intraocular implant may comprise a mixture of two or more biodegradable polymers. For example, the implant may comprise a mixture of a first biodegradable polymer and a different second biodegradable polymer. One or more of the biodegradable polymers may have terminal acid groups.

Release of a drug from an erodible polymer is the consequence of several mechanisms or combinations of mechanisms. Some of these mechanisms include desorption from the implants surface, dissolution, diffusion through porous channels of the hydrated polymer and erosion. Erosion can be bulk or surface or a combination of both. As discussed herein, the matrix of the intraocular implant may release drug at a rate effective to sustain release of an amount of the TKI for more than one week after implantation into an eye. In certain implants, therapeutic amounts of the TKI are released for more than about one month, and even for about six months or more.

One example of the biodegradable intraocular implant comprises a TKI with a biodegradable polymer matrix that comprises a poly(lactide-co-glycolide) or a poly(D,L-lactide-co-glycolide). The implant may have an amount of the TKI from about 20% to about 60% by weight of the implant. Such a mixture is effective in sustaining release of a therapeutically effective amount of the TKI for a time period from about one month to about six months from the time the implant is placed in an eye.

Another example of the biodegradable intraocular implant comprises a TKI with a biodegradable polymer matrix that comprises a single type of polymer. For example, the biodegradable polymer matrix may consist essentially of a polycaprolactone. The polycaprolactone may have a molecular weight between about 10 and about 20 kilodaltons, such as about 15 kilodaltons. These implants are capable of providing a nearly linear release rate for at least about 70 days.

The release of the TKI(s) from the intraocular implant comprising a biodegradable polymer matrix may include an initial burst of release followed by a gradual increase in the amount of the TKI released, or the release may include an initial delay in release of the TKI followed by an increase in release. When the implant is substantially completely degraded, the percent of the TKI(s) that has been released is about one hundred. Compared to existing implants, the implants disclosed herein do not completely release, or release about 100% of the TKI(s), until after about one week of being placed in an eye.

It may be desirable to provide a relatively constant rate of release of the TKI(s) from the implant over the life of the implant. For example, it may be desirable for the TKI(s) to be released in amounts from about 0.01 µg to about 2 µg per day for the life of the implant. However, the release rate may change to either increase or decrease depending on the formulation of the biodegradable polymer matrix. In addition, the release profile of the TKI(s) may include one or more linear portions and/or one or more non-linear portions. Preferably, the release rate is greater than zero once the implant has begun to degrade or erode.

The implants may be monolithic, i.e. having the active agent or agents homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated, reservoir-type implant may be of benefit in some circumstances, where the therapeutic level of the drug falls within a narrow window. In addition, the therapeutic component, including the TKI(s), may be distributed in a non-homogenous pattern in the matrix. For example, the implant may include a portion that has a greater concentration of the TKI(s) relative to a second portion of the implant.

Figure 14:
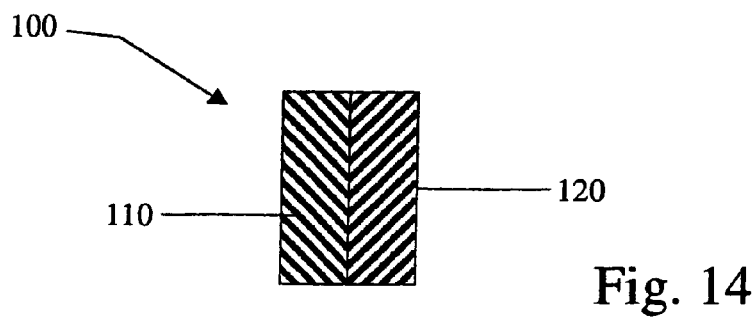
FIG. 14 is an illustration of a biodegradable implant comprising a drug-releasing active layer and a barrier layer.

One such implant 100 is illustrated in FIG. 14. The implant 100 may be understood to be a unidirectional drug delivery device. The implant 100 is characterized by comprising a first portion 110 and a second portion 120. First portion 110 comprises a mixture of a therapeutic agent, such as TKI, and a biodegradable polymer matrix, such as a matrix of PLGA, PLA, or a combination thereof. Second portion 120 comprises a polymer, such as a biodegradable polymer, and is substantially free of the therapeutic agent. The polymeric component of the first portion 110 and the second portion 120 may comprise the same polymer material, e.g., both components may be made from a PLGA polymer. Although the therapeutic agent is a TKI, other implants may include other therapeutic agents, including those described herein. First portion 110 may be understood to be an active layer, and second portion 120 may be understood to be a barrier layer, which is effective to prevent or reduce diffusion of the therapeutic agent from one side of the implant. The layers may be separately formed as films and pressed together using a Carver press, for example. Or the layers may be co-extruded using conventional extrusion techniques or injection molded using injection molding techniques. The implant 110 is effective to control the flow or release of a therapeutic agent in a specific direction, such as one direction. The implant can be applied to a diseased location, such as in an eye, that needs the release of the therapeutic agent in a specific and controlled manner, such as for subconjunctival applications.

The present implants may also comprise a combination of a TKI and polycaprolactone, as described herein. Such implants may provide a single order release rate for about 70 days or more after placement in an eye. The polycaprolactone may have a molecular weight of about 15 kilodaltons. Thus, one embodiment of the present implants, comprises a poorly soluble drug or therapeutic agent and a single polymeric component that releases the drug at a substantially linear release rate (e.g., a zero order rate).

The present implants may also include a non-biodegradable polymer component, as described herein. The release of a therapeutic agent, such as TKI, may be achieved by movement of the therapeutic agent through one or more openings, orifices, or holes. An example of such an implant is disclosed in U.S. Pat. No. 6,331,313.

The intraocular implants disclosed herein may have a size of between about 5 μm and about 2 mm, or between about 10 μm and about 1 mm for administration with a needle, greater than 1 mm, or greater than 2 mm, such as 3 mm or up to 10 mm, for administration by surgical implantation. The vitreous chamber in humans is able to accommodate relatively large implants of varying geometries, having lengths of, for example, 1 to 10 mm. The implant may be a cylindrical pellet (e.g., rod) with dimensions of about 2 mm×0.75 mm diameter. Or the implant may be a cylindrical pellet with a length of about 7 mm to about 10 mm, and a diameter of about 0.75 mm to about 1.5 mm.

The implants may also be at least somewhat flexible so as to facilitate both insertion of the implant in the eye, such as in the vitreous, and accommodation of the implant. The total weight of the implant is usually about 250-5000 μg, more preferably about 500-1000 μg. For example, an implant may be about 500 μg, or about 1000 μg. For non-human individuals, the dimensions and total weight of the implant(s) may be larger or smaller, depending on the type of individual. For example, humans have a vitreous volume of approximately 3.8 ml, compared with approximately 30 ml for horses, and approximately 60-100 ml for elephants. An implant sized for use in a human may be scaled up or down accordingly for other animals, for example, about 8 times larger for an implant for a horse, or about, for example, 26 times larger for an implant for an elephant.

Thus, implants can be prepared where the center may be of one material and the surface may have one or more layers of the same or a different composition, where the layers may be cross-linked, or of a different molecular weight, different density or porosity, or the like. For example, where it is desirable to quickly release an initial bolus of drug, the center may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

The implants may be of any geometry including fibers, sheets, films, microspheres, spheres, circular discs, plaques and the like. The upper limit for the implant size will be determined by factors such as toleration for the implant, size limitations on insertion, ease of handling, etc. Where sheets or films are employed, the sheets or films will be in the range of at least about 0.5 mm×0.5 mm, usually about 3-10 mm×5-10 mm with a thickness of about 0.1-1.0 mm for ease of handling. Where fibers are employed, the fiber diameter will generally be in the range of about 0.05 to 3 mm and the fiber length will generally be in the range of about 0.5-10 mm. Spheres may be in the range of about 0.5 μm to 4 mm in diameter, with comparable volumes for other shaped particles.

The size and form of the implant can also be used to control the rate of release, period of treatment, and drug concentration at the site of implantation. Larger implants will deliver a proportionately larger dose, but depending on the surface to mass ratio, may have a slower release rate. The particular size and geometry of the implant are chosen to suit the site of implantation.

The proportions of TKI(s), polymer, and any other modifiers may be empirically determined by formulating several implants with varying proportions. A USP approved method for dissolution or release test can be used to measure the rate of release (USP 23; NF 18 (1995) pp. 1790-1798). For example, using the infinite sink method, a weighed sample of the implant is added to a measured volume of a solution containing 0.9% NaCl in water, where the solution volume will be such that the drug concentration is after release is less than 5% of saturation. The mixture is maintained at 37° C. and stirred slowly to maintain the implants in suspension. The appearance of the dissolved drug as a function of time may be followed by various methods known in the art, such as spectrophotometrically, HPLC, mass spectroscopy, etc. until the absorbance becomes constant or until greater than 90% of the drug has been released.

In addition to the TKI(s) included in the intraocular implants disclosed herein, the intraocular implants may also include one or more additional ophthalmically acceptable therapeutic agents. For example, the implant may include one or more antihistamines, one or more antibiotics, one or more beta blockers, one or more steroids, one or more antineoplastic agents, one or more immunosuppressive agents, one or more antiviral agents, one or more antioxidant agents, and mixtures thereof.

Pharmacologic or therapeutic agents which may find use in the present systems, include, without limitation, those disclosed in U.S. Pat. No. 4,474,451, columns 4-6 and U.S. Pat. No. 4,327,725, columns 7-8.

Examples of antihistamines include, and are not limited to, loratadine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimeprazine doxylamine, pheniramine, pyrilamine, chlorcyclizine, thonzylamine, and derivatives thereof.

Examples of antibiotics include without limitation, cefazolin, cephradine, cefaclor, cephapirin, ceftizoxime, cefoperazone, cefotetan, cefutoxime, cefotaxime, cefadroxil, ceftazidime, cephalexin, cephalothin, cefamandole, cefoxitin, cefonicid, ceforamide, ceftriaxone, cefadroxil, cephradine, cefuroxime, cyclosporine, ampicillin, amoxicillin, cyclacillin, ampicillin, penicillin G, penicillin V potassium, piperacillin, oxacillin, bacampicillin, cloxacillin, ticarcillin, aziocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, gatifloxacin, ofloxacin, and derivatives thereof.

Examples of beta blockers include acebutolol, atenolol, labetalol, metoprolol, propranolol, timolol, and derivatives thereof.

Examples of steroids include corticosteroids, such as cortisone, prednisolone, fluorometholone, dexamethasone, medrysone, loteprednol, fluazacort, hydrocortisone, prednisone, betamethasone, prednisone, methylprednisolone, triamcinolone hexacatonide, paramethasone acetate, diflorasone, fluocinonide, fluocinolone, triamcinolone, derivatives thereof, and mixtures thereof.

Examples of antineoplastic agents include adriamycin, cyclophosphamide, actinomycin, bleomycin, daunorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol and derivatives thereof, taxotere and derivatives thereof, vinblastine, vincristine, tamoxifen, etoposide, piposulfan, cyclophosphamide, and flutamide, and derivatives thereof.

Examples of immunosuppressive agents include cyclosporine, azathioprine, tacrolimus, and derivatives thereof.

Examples of antiviral agents include interferon gamma, zidovudine, amantadine hydrochloride, ribavirin, acyclovir, valciclovir, dideoxycytidine, phosphonoformic acid, ganciclovir and derivatives thereof.

Examples of antioxidant agents include ascorbate, alphatocopherol, mannitol, reduced glutathione, various carotenoids, cysteine, uric acid, taurine, tyrosine, superoxide dismutase, lutein, zeaxanthin, cryptoxanthin, astaxanthin, lycopene, N-acetyl-cysteine, carnosine, gamma-glutamylcysteine, quercetin, lactoferrin, dihydrolipoic acid, citrate, *Ginkgo Biloba* extract, tea catechins, bilberry extract, vitamins E or esters of vitamin E, retinyl palmitate, and derivatives thereof.

Other therapeutic agents include squalamine, carbonic anhydrase inhibitors, alpha agonists, prostamides, prostaglandins, antiparasitics, antifungals, and derivatives thereof.

The amount of active agent or agents employed in the implant, individually or in combination, will vary widely depending on the effective dosage required and the desired rate of release from the implant. As indicated herein, the agent will be at least about 1, more usually at least about 10 weight percent of the implant, and usually not more than about 80, more usually not more than about 40 weight percent of the implant.

In addition to the therapeutic component, the intraocular implants disclosed herein may include effective amounts of buffering agents, preservatives and the like. Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents advantageously present in amounts sufficient to maintain a pH of the system of between about 2 to about 9 and more preferably about 4 to about 8. As such the buffering agent may be as much as about 5% by weight of the total implant. Suitable water soluble preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. These agents may be present in amounts of from 0.001 to about 5% by weight and preferably 0.01 to about 2% by weight.

In addition, the implants may include a solubility enhancing component provided in an amount effective to enhance the solubility of the TKI(s) relative to substantially identical implants without the solubility enhancing component. For example, an implant may include a β-cyclodextrin, which is effective in enhancing the solubility of the TKI. The β-cyclodextrin may be provided in an amount from about 0.5% (w/w) to about 25% (w/w) of the implant. In certain implants, the β-cyclodextrin is provided in an amount from about 5% (w/w) to about 15% (w/w) of the implant.

In some situations mixtures of implants may be utilized employing the same or different pharmacological agents. In this way, a cocktail of release profiles, giving a biphasic or triphasic release with a single administration is achieved, where the pattern of release may be greatly varied. The implants may also have a sigmoidal release profile.

Additionally, release modulators such as those described in U.S. Pat. No. 5,869,079 may be included in the implants. The amount of release modulator employed will be dependent on the desired release profile, the activity of the modulator, and on the release profile of the TKI in the absence of modulator. Electrolytes such as sodium chloride and potassium chloride may also be included in the implant. Where the buffering agent or enhancer is hydrophilic, it may also act as a release accelerator. Hydrophilic additives act to increase the release rates through faster dissolution of the material surrounding the drug particles, which increases the surface area of the drug exposed, thereby increasing the rate of drug bioerosion. Similarly, a hydrophobic buffering agent or enhancer dissolve more slowly, slowing the exposure of drug particles, and thereby slowing the rate of drug bioerosion.

Various techniques may be employed to produce the implants described herein. Useful techniques include, but are not necessarily limited to, solvent evaporation methods, phase separation methods, interfacial methods, molding methods, injection molding methods, extrusion methods, coextrusion methods, carver press method, die cutting methods, heat compression, combinations thereof and the like.

Specific methods are discussed in U.S. Pat. No. 4,997,652. Extrusion methods may be used to avoid the need for solvents in manufacturing. When using extrusion methods, the polymer and drug are chosen so as to be stable at the temperatures required for manufacturing, usually at least about 85 degrees Celsius. Extrusion methods use temperatures of about 25 degrees C. to about 150 degrees C., more preferably about 65 degrees C. to about 130 degrees C. An implant may be produced by bringing the temperature to about 60 degrees C. to about 150 degrees C. for drug/polymer mixing, such as about 130 degrees C., for a time period of about 0 to 1 hour, 0 to 30 minutes, or 5-15 minutes. For example, a time period may be about 10 minutes, preferably about 0 to 5 min. The implants are then extruded at a temperature of about 60 degrees C. to about 130 degrees C., such as about 75 degrees C.

In addition, the implant may be coextruded so that a coating is formed over a core region during the manufacture of the implant.

Compression methods may be used to make the implants, and typically yield implants with faster release rates than extrusion methods. Compression methods may use pressures of about 50-150 psi, more preferably about 70-80 psi, even more preferably about 76 psi, and use temperatures of about 0 degrees C. to about 115 degrees C., more preferably about 25 degrees C.

The implants of the present invention may be inserted into the eye, for example the vitreous chamber of the eye, by a variety of methods, including placement by forceps or by trocar following making a 2-3 mm incision in the sclera. One example of a device that may be used to insert the implants into an eye is disclosed in U.S. Patent Publication No. 2004/0054374. The method of placement may influence the therapeutic component or drug release kinetics. For example, delivering the implant with a trocar may result in placement of the implant deeper within the vitreous than placement by forceps, which may result in the implant being closer to the edge of the vitreous. The location of the implant may influence the concentration gradients of therapeutic component or drug surrounding the element, and thus influence the release rates (e.g., an element placed closer to the edge of the vitreous may result in a slower release rate).

The present implants are configured to release an amount of the TKI(s) effective to treat or reduce a symptom of an ocular condition, such as a posterior ocular condition.

The implants disclosed herein may also be configured to release the TKI or additional therapeutic agents, as described above, which to prevent diseases or conditions, such as the following:

MACULOPATHIES/RETINAL DEGENERATION: Non-Exudative Age Related Macular Degeneration (ARMD), Exudative Age Related Macular Degeneration (ARMD), Choroidal Neovascularization, Diabetic Retinopathy, Acute Macular Neuroretinopathy, Central Serous Chorioretinopathy, Cystoid Macular Edema, Diabetic Macular Edema.

UVEITIS/RETINITIS/CHOROIDITIS: Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpiginous Choroiditis, Subretinal Fibrosis and Uveitis Syndrome, Vogt-Koyanagi-Harada Syndrome.

VASCULAR DISEASES/EXUDATIVE DISEASES: Coat's Disease, Parafoveal Telangiectasis, Papillophlebitis, Frosted Branch Angitis, Sickle Cell Retinopathy and other Hemoglobinopathies, Angioid Streaks, Familial Exudative Vitreoretinopathy.

TRAUMATIC/SURGICAL: Sympathetic Ophthalmia, Uveitic Retinal Disease, Retinal Detachment, Trauma, Laser, PDT, Photocoagulation, Hypoperfusion During Surgery, Radiation Retinopathy, Bone Marrow Transplant Retinopathy.

PROLIFERATIVE DISORDERS: Proliferative Vitreal Retinopathy and Epiretinal Membranes, Proliferative Diabetic Retinopathy, Retinopathy of Prematurity (retrolental fibroplastic).

INFECTIOUS DISORDERS: Ocular Histoplasmosis, Ocular Toxocariasis, Presumed Ocular Histoplasmosis Syndrome (POHS), Endophthalmitis, Toxoplasmosis, Retinal Diseases Associated with HIV Infection, Choroidal Disease Associated with HIV Infection, Uveitic Disease Associated with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis.

GENETIC DISORDERS: Systemic Disorders with Associated Retinal Dystrophies, Congenital Stationary Night Blindness, Cone Dystrophies, Fundus Flavimaculatus, Best's Disease, Pattern Dystrophy of the Retinal Pigmented Epithelium, X-Linked Retinoschisis, Sorsby's Fundus Dystrophy, Benign Concentric Maculopathy, Bietti's Crystalline Dystrophy, pseudoxanthoma elasticum, Osler Weber syndrome.

RETINAL TEARS/HOLES: Retinal Detachment, Macular Hole, Giant Retinal Tear.

TUMORS: Retinal Disease Associated with Tumors, Solid Tumors, Tumor Metastasis, Benign Tumors, for example, hemangiomas, neurofibromas, trachomas, and pyogenic granulomas, Congenital Hypertrophy of the RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, Intraocular Lymphoid Tumors.

MISCELLANEOUS: Punctate Inner Choroidopathy, Acute Posterior Multifocal Placoid Pigment Epitheliopathy, Myopic Retinal Degeneration, Acute Retinal Pigment Epithelitis, Ocular inflammatory and immune disorders, ocular vascular malfunctions, Corneal Graft Rejection, Neovascular Glaucoma and the like.

In one embodiment, an implant, such as the implants disclosed herein, is administered to a posterior segment of an eye of a human or animal patient, and preferably, a living human or animal. In at least one embodiment, an implant is administered without accessing the subretinal space of the eye. For example, a method of treating a patient may include placing the implant directly into the posterior chamber of the eye. In other embodiments, a method of treating a patient may comprise administering an implant to the patient by at least one of intravitreal injection, subconjunctival injection, sub-tenon injections, retrobulbar injection, and suprachoroidal injection.

In at least one embodiment, a method of improving vision or maintaining vision in a patient comprises administering one or more implants containing one or more TKIs, as disclosed herein to a patient by at least one of intravitreal injection, subconjunctival injection, sub-tenon injection, retrobulbar injection, and suprachoroidal injection. A syringe apparatus including an appropriately sized needle, for example, a 22 gauge needle, a 27 gauge needle or a 30 gauge needle, can be effectively used to inject the composition with the posterior segment of an eye of a human or animal. Repeat injections are often not necessary due to the extended release of the TKI from the implants.

In another aspect of the invention, kits for treating an ocular condition of the eye are provided, comprising: a) a container comprising an extended release implant comprising a therapeutic component including a TKI, and a drug release sustaining component; and b) instructions for use. Instructions may include steps of how to handle the implants, how to insert the implants into an ocular region, and what to expect from using the implants.

Example 1

Intravitreal Pharmacokinetics of TKIs in Fluid Compositions

The ocular pharmacokinetics of AGN 199659, AGN 200954, AGN 201088 and AGN 201666 following single intravitreal injections into female albino rabbit eyes was determined. The animals were dosed with a 50 µL intravitreal injection of 242 ng AGN 201088, 128 ng AGN 201666, 114 ng AGN 199659 or 222 ng of AGN 200954 per eye. Vitreous humor samples (n=4 eyes per timepoint) were collected at 0.5, 1, 2, 4, 8, and 12 hr postdose. The TKI concentration in the vitreous humor was determined using a liquid chromatography tandem mass spectrometry method (LC-MS/MS).

Figure 2:
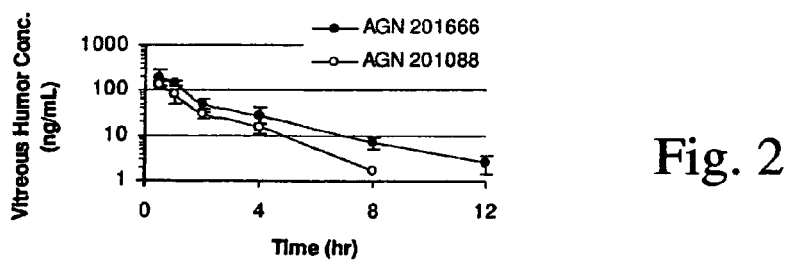
FIG. 2 is a graph similar to FIG. 1 for two different TKIs.

All compounds were eliminated fairly rapidly from the rabbit eye. This indicates a transretinal route of elimination. There was no bias to compound nucleus. However, even though elimination was extremely rapid it was determined that local sustained delivery was feasible. Based on the vitreal clearance determined in this study for 3-[(4-Morpholin-4-yl-phenylamino)-methylene]-1,3-dihydro-indol-2-one, 3-(6-Amino-3H-isobenzofuran-1-ylidene)-5-chloro-1,3-dihydro-indol-2-one, AGN 201088 and AGN 201666, and assuming steady state efficacious concentration at twice the EC50 values (determined by in vitro receptor binding and intracellular Ca2+ assay) all the tyrosine kinase inhibitors tested could be formulated into 1 mg implants that would maintain the desired steady state drug vitreal concentrations for a duration of about six months. This data is summarized in Table 1 and FIGS. 1 and 2.

TABLE 1

| | \multicolumn{4}{c}{TKI Pharmacokinetic Parameters after a Single Intravitreal Injection} |
|---|---|---|---|---|
| Parameter | AGN 199659 | AGN 200954 | AGN 201088 | AGN 201666 |
| Dose (ng) | 114 | 222 | 242 | 128 |
| $C_0$ (ng/mL) | 502 | 566 | 222 | 332 |

TABLE 1-continued

| | \multicolumn{4}{c}{TKI Pharmacokinetic Parameters after a Single Intravitreal Injection} |
|---|---|---|---|---|
| Parameter | AGN 199659 | AGN 200954 | AGN 201088 | AGN 201666 |
| $t_{1/2}$ (hr) | 1.21 | 2.59 | 1.11 | 2.32 |
| $AUC_{0-tlast}$ (ng · hr/mL) | 488 | 778 | 272 | 466 |
| Cl (mL/hr) | 0.232 | 0.260 | 0.885 | 0.270 |
| $V_{ss}$ (mL) | 0.255 | 0.705 | 1.23 | 0.577 |
| Theoretical 6 mo dose | 200 ug | 5 ug | 150 ug | 126 ug |

Example 2

TKI Biodegradable Implants

Tyrosine kinase inhibitors were incorporated into PLGA or PLA implants by extrusion. The TKIs were milled with the polymers at certain ratios then extruded into filaments. These filaments were subsequently cut into implants weighing approximately 1 mg. Several TKIs were formulated in the PLGA and PLA implants based on their potencies and physicochemical properties as shown in Table 2.

TABLE 2

| | | | | | |
|---|---|---|---|---|---|
| \multicolumn{6}{c}{Tyrosine Kinase Inhibitors Formulated in PLGA Implants} |
| AGN Number | Structure | Projected $C_{ss}$ Efficacy | Solubility (μg/mL) pH7 | log P | pKa |
| AGN 200954 | | 4 ng/mL | 0.3 | 2.21 | 4.24 10.03 |
| AGN 202314 | | 96 ng/mL | 202 | 3.80 | 9.68 |

TABLE 2-continued

Tyrosine Kinase Inhibitors Formulated in PLGA Implants

| AGN Number | Structure | Projected $C_{ss}$ Efficacy | Solubility (μg/mL) pH7 | log P | pKa |
|---|---|---|---|---|---|
| AGN 202560 | 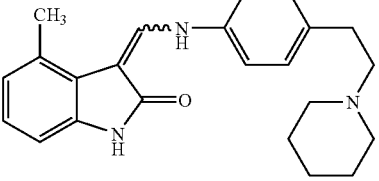 | 105 ng/mL | 41 | 3.66 | 9.65 |
| AGN 201634 | 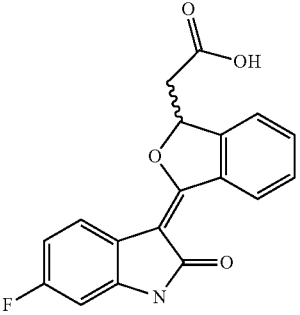 [SMILES: O=C(O)CC1O/C(=C2/C(=O)Nc3cc(F)ccc32)c2ccccc21] | 28 ng/mL | 88 | 1.25 | 4.06 10.25 |

TKI release from the implants was assessed in vitro. Implants were placed into vials containing release medium and shaken at 37° C. At the appropriate time points a sample was taken from the release medium for analysis and the medium totally replaced to maintain sink conditions. Drug in the sample was assayed by HPLC and the cumulative percent release of drug from the implant noted as a function of time. The in vitro release profiles of AGN 200954, AGN 202314, AGN 201635 and AGN 202564 are depicted in FIGS. 3 through 10, respectively.

From the formulation release data depicted in FIGS. 3 through 10 it is evident that TKIs over a wide range of physicochemical properties can be engineered to release drug in vitro over a period of weeks to a year.

Example 3

In Vivo Pharmacokinetic Properties of TKI-Containing Implants

Figure 3:
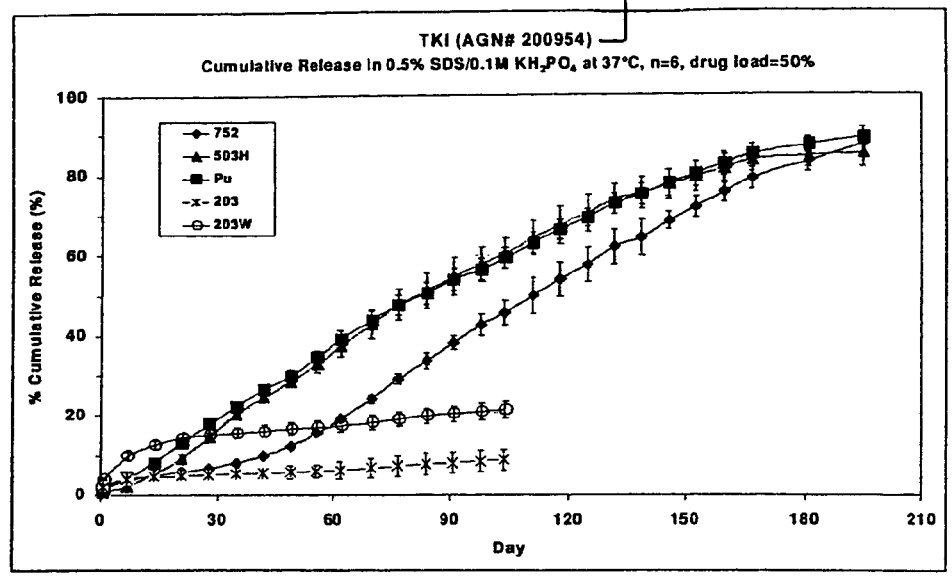
FIG. 3 is a graph of the cumulative release profile for AGN 200954 as a function of time.
Figure 4:
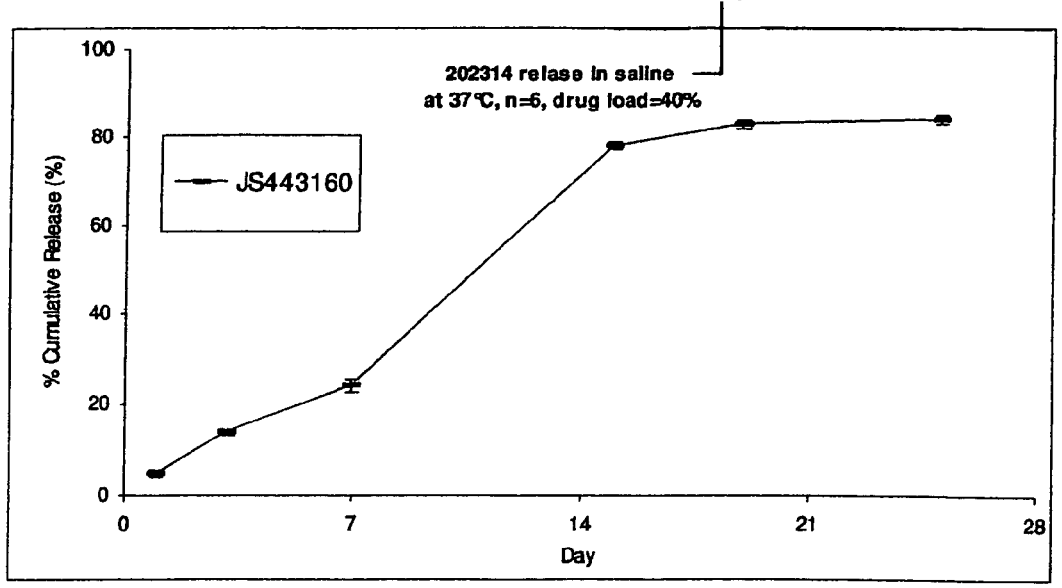
FIG. 4 is a graph of the cumulative release profile for AGN 202314 as a function of time.
Figure 5:
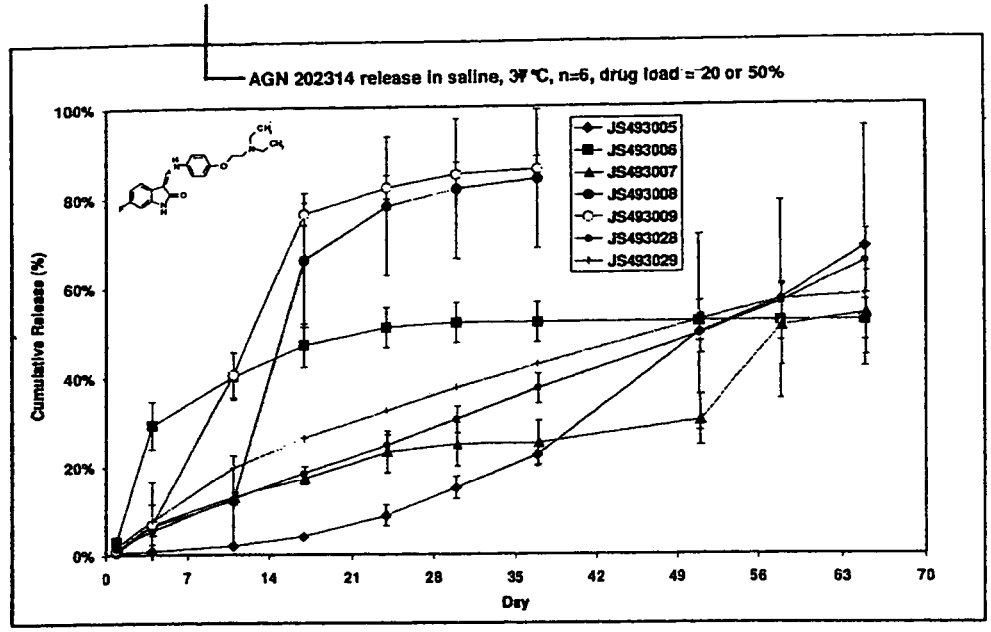
FIG. 5 is a graph similar to FIG. 4 for different formulations of AGN 202314.

Implants containing AGN 202314 were placed intravitreally or subconjunctivally in an eye. The implants released AGN 202314 in-vitro over a 14 day period (FIG. 3). The intent of this study was to achieve an intravitreal in-vivo/in-vitro correlation with the intravitreal implants and assess the feasibility of periocular delivery.

Intravitreal Implants, PLGA (400 μg AGN 202314 dose, 1 mg total implant weight), were implanted by surgical incision into the mid vitreous of albino rabbits. At days 8, 15, 31 and 61 rabbits were sacrificed and the vitreous humor, lens, aqueous humor and plasma assayed for AGN 202314.

Subconjunctival implants, PLGA (1200 μg AGN 202314 dose; three implants) and PLA microspheres (300 μg AGN 202314) were implanted subconjunctivally. At days 8, 15, 31 and 61 rabbits were sacrificed and the vitreous humor, lens, aqueous humor and plasma assayed for AGN 202314.

The data are summarized in Tables 3 through 5

TABLE 3

PK Results from 2 Month Intravitreal Implantation AGN 202314 Implant (400 μg rod)

| | Day | | | |
|---|---|---|---|---|
| | 8 | 15 | 31 | 61 |
| Retina (ng/g) | 1220 | 100 | BLQ | BLQ |
| Vitreous Humor (ng/g) | 327 | 85 | BLQ | BLQ |
| Lens (ng/g) | ALQ (6580) | ALQ (8980) | 724 | 35.8 |
| Aqueous Humor (ng/mL) | 2.10 | 6.50 | BLQ | BLQ |
| Plasma (ng/mL) | 0.255 | BLQ | BLQ | BLQ |

Below the limit of quantitation (BLQ): Retina and lens: <5 ng/g, VH: <30 ng/g, AH: <0.5 ng/mL, Plasma: <0.5 ng/mL
Above the limit of quantitation (ALQ): Retina and lens: >2000 ng/g, VH: >3000 ng/g, AH: >30 ng/mL, Plasma: >200 ng/mL

TABLE 4

PK Results from 2 Mo Subconjunctival Implantation of AGN 202314 Microspheres

| | Day | | | |
|---|---|---|---|---|
| | 8 | 15 | 31 | 61 |
| Microsphere (300 μg AGN 202314) - 0.63 dL/g PLA | | | | |
| Retina (ng/g) | 12.4 | BLQ | 19.2 | BLQ |
| Vitreous Humor (ng/g) | BLQ | BLQ | BLQ | BLQ |
| Lens (ng/g) | 5.19 | BLQ | BLQ | BLQ |
| Aqueous Humor (ng/mL) | BLQ | BLQ | BLQ | BLQ |
| Plasma (ng/mL) | BLQ | BLQ | BLQ | BLQ |
| Microsphere (300 μg AGN 202314) - 1.2 dL/g PLA | | | | |
| Retina (ng/g) | 3.7 | 5.1 | BLQ | BLQ |
| Vitreous Humor (ng/g) | BLQ | BLQ | BLQ | BLQ |

TABLE 4-continued

PK Results from 2 Mo Subconjunctival Implantation of AGN 202314 Microspheres

| | Day | | | |
|---|---|---|---|---|
| | 8 | 15 | 31 | 61 |
| Lens (ng/g) | BLQ | BLQ | 2.72 | BLQ |
| Aqueous Humor (ng/mL) | BLQ | BLQ | BLQ | BLQ |
| Plasma (ng/mL) | BLQ | BLQ | BLQ | BLQ |

BLQ = Retina (<5 ng/g), VH (<30 ng/g), lens (<5 ng/g), AH (<0.5 ng/mL), plasma (<0.5 ng/mL)

TABLE 5

Month Subconjunctival Implantation (3 rods with a total of 1.2 mg AGN 202314)

| | Day | | | |
|---|---|---|---|---|
| | 8 | 15 | 31 | 61 |
| Retina (ng/g) | 63.8 | BLQ | BLQ | BLQ |
| Vitreous Humor (ng/g) | BLQ | BLQ | BLQ | BLQ |
| Lens (ng/g) | 229 | 7.93 | BLQ | BLQ |
| Aqueous Humor (ng/mL) | 6.38 | BLQ | BLQ | BLQ |
| Plasma (ng/mL) | BLQ | BLQ | BLQ | BLQ |

BLQ: Retina and lens: <5 ng/g, VH: <30 ng/g, AH: <0.5 ng/mL, Plasma: <0.5 ng/mL

The data from this study indicates that a good in vitro in vivo correlation was established for AGN 202314. The AGN 202314 implant released drug over a two week period both in vitro and in vivo. It is also important that plasma levels remain BLQ or extremely low for all time points. This shows that even in a worst case scenario of intravitreal delivery over two weeks systemic exposure is negligible. It was also noted that periocular delivery was unsuccessful at delivering AGN 202314 to the vitreous and retina.

Figure 6:
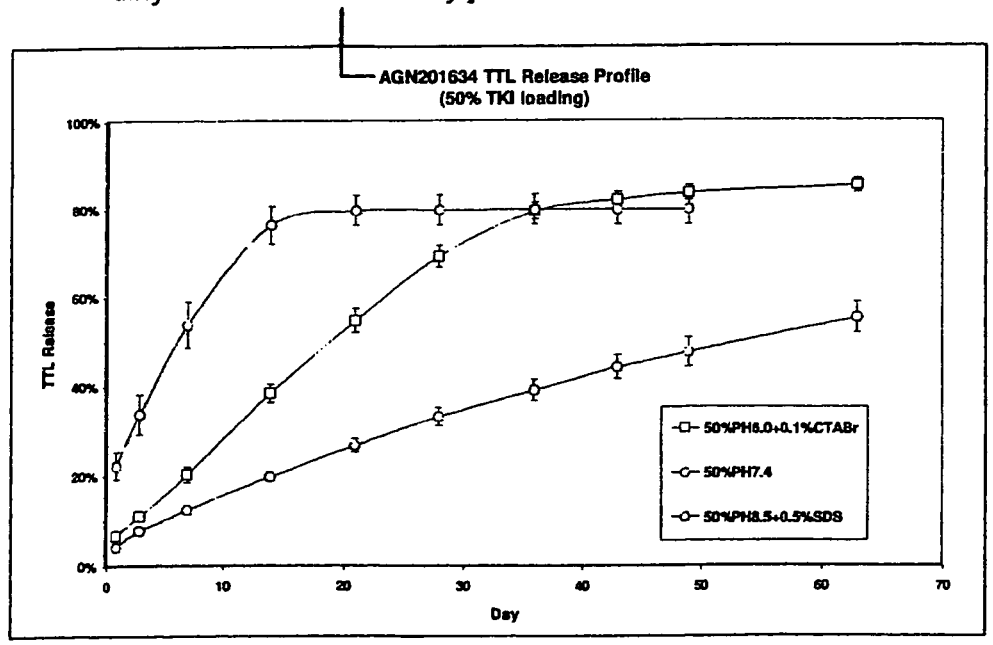
FIG. 6 is a graph of the TTL release for AGN 201634 as a function of time.
Figure 7:
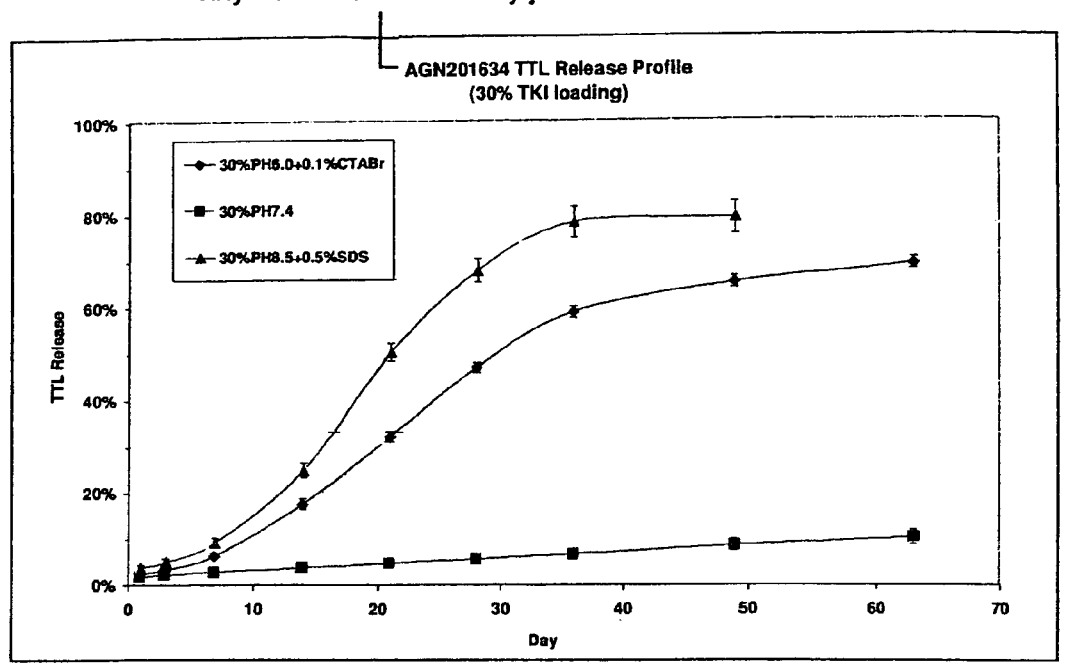
FIG. 7 is a graph similar to FIG. 6 with implants containing 30% AGN 201634.
Figure 8:
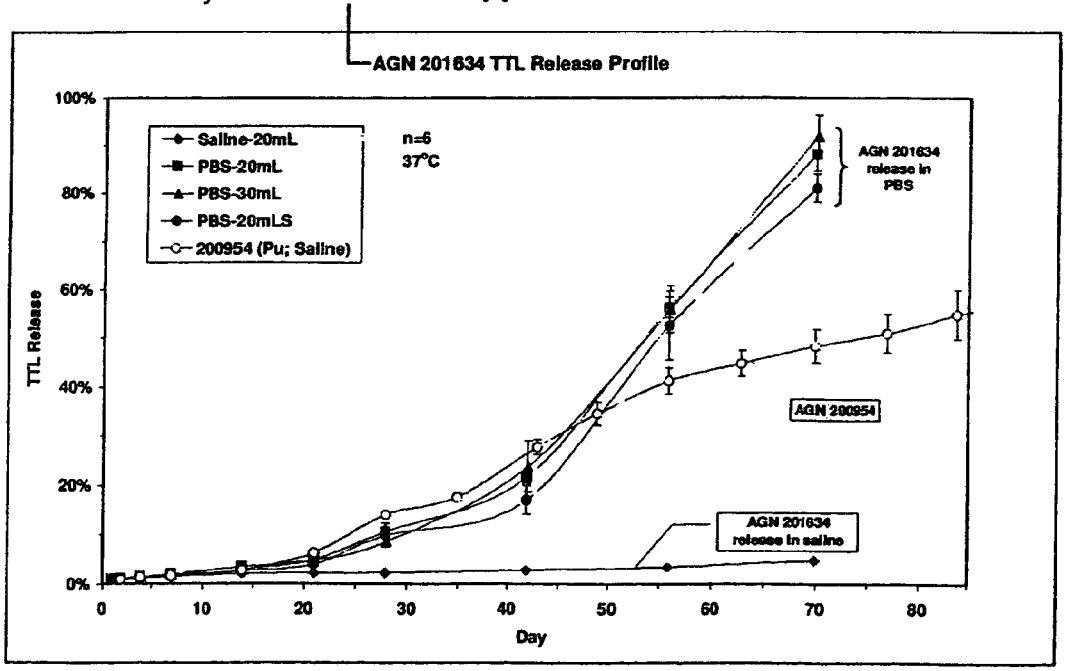
FIG. 8 is a graph similar to FIG. 6 for AGN 201634 in different solutions.
Figure 9:
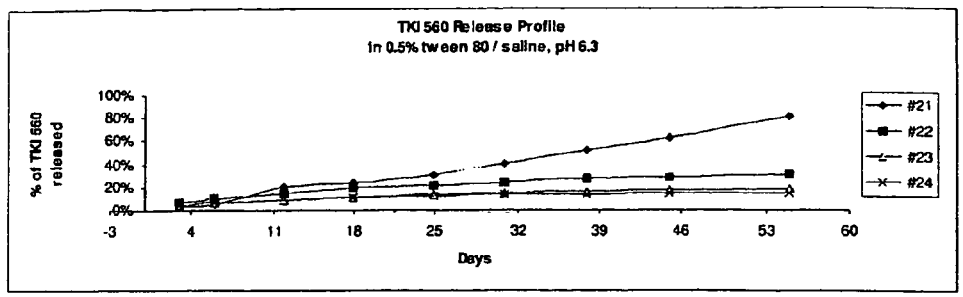
FIG. 9 is a graph of the percent of TKI released as a function of time in different a Tween 80/saline solution.
Figure 10:
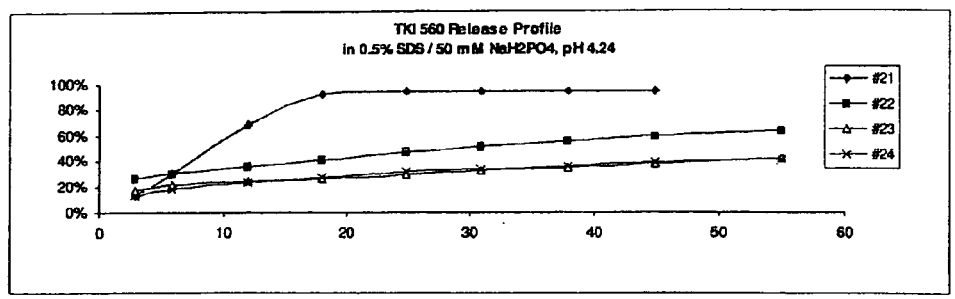
FIG. 10 is a graph similar to FIG. 9 except in a phosphate buffer solution.

A follow-on two-month ocular pharmacokinetic study of AGN 202314 following a single intravitreal implantation into albino rabbit eyes was initiated. The formulations delivered AGN 202314 over a period of four months in-vitro. The following 1 mg implants were evaluated: 30% AGN 202314/70% Purac PLA; Lot# JS493028 (FIG. 4), 50% AGN 201634/50% Purac PLA; Lot # JS493034 (FIG. 6). Two rabbits (4 eyes and 2 plasma) were used per timepoint. Implants were administered by a bilateral surgical intravitreal placement by sclerotomy without vitrectomy. The vitreous humor and retina AGN 202314 concentrations were assayed at days 8, 15, 31 and 61. The data are displayed in Table 6.

TABLE 6

One Month Data from the AGN 202314 Intravitreal Study

| | Day | | |
|---|---|---|---|
| | 8 | 15 | 31 |
| 50% Purac PLA (AGN 202314 - 500 µg) | | | |
| Retina (ng/g) | 95.3 ± 18.7 | 87.7 ± 29.6 | 157 ± 120 |
| VH (ng/g): | 22.2 ± 25.6 | BLQ | 69.9 ± 87.5 |
| 70% Purac PLA (AGN 202314 - 300 µg) | | | |
| Retina (ng/g) | 78.1 ± 7.2 | 197 ± 88.7 | 189 ± 126 |
| VH (ng/g) | BLQ | 33.7 ± 25.8 | BLQ |

Analytical range: Retina BLQ < 5 ng/g; VH BLQ < 30 ng/g

The retinal levels achieved from this study approach therapeutic levels by the first week and are maintained over the first thirty days. This data shows that actual in vivo sustained delivery of a TKI locally is feasible.

A six month pharmacokinetic study was initiated with intravitreal and subconjunctival AGN 200954 implants. The implants released AGN 200954 in-vitro over a 180 day period (FIG. 3). Intravitreal Implants, PLGA (500 µg AGN 200954 dose, 1 mg total implant weight, Purac polymer) and PLGA (500 µg AGN 200954 dose, 1 mg total implant weight, RG503H polymer), were implanted by surgical incision into the mid vitreous of albino rabbits. At days 8, 15, 31 and 61 rabbits were sacrificed and the vitreous humor, lens, aqueous humor and plasma assayed for AGN 200954. Subconjunctival implants, PLGA implant (500 µg AGN 200954 dose, 1 mg total implant weight, Purac polymer) and PLGA microspheres (370 µg and 740 µg AGN 200954), were administered. At days 8, 15, 31 and 61 rabbits were sacrificed and the vitreous humor, lens, aqueous humor and plasma assayed for AGN 200954.

AGN 200954 Pharmacokinetics after Intravitreal Administration

| | Day | | | | |
|---|---|---|---|---|---|
| | 8 | 31 | 61 | 91 | 181 |
| Intravitreal Implantation (500 µg rod) Formulation PU | | | | | |
| Retina (ng/g) | BLQ | 48.7 | 207 | 161 | 210 |
| Vitreous Humor(ng/g) | BLQ | 18.2 | 109 | 657 | 76.3 |
| Lens (ng/g) | 70.2 | 243 | 586 | 768 | 1296 |
| Aqueous Humor (ng/mL) | BLQ | BLQ | BLQ | BLQ | 288 |
| Plasma (ng/mL) | BLQ | BLQ | BLQ | BLQ | BLQ |
| Intravitreal Implantation (500 µg rod) Formulation RG503H | | | | | |
| Retina (ng/g) | 15.7 | 17.7 | 416 | 58.4 | 24.9 |
| Vitreous Humor(ng/g) | 560 | 126 | 189 | 65.2 | 227 |
| Lens (ng/g) | 160 | 386 | 464 | 239 | 248 |
| Aqueous Humor (ng/mL) | BLQ | BLQ | BLQ | BLQ | 316 |
| Plasma (ng/mL) | BLQ | BLQ | BLQ | BLQ | BLQ |

BLQ = Retina (5 ng/g), VH (30 ng/g), lens (5 ng/g), AH (0.05 ng/mL), plasma (0.05 ng/mL)

It is evident from the data that a considerable in-vivo lag time exists for the first formulation not seen in vitro. Neither formulation exhibits measurable plasma concentrations.

Example 4

In Vitro Release of a TKI (AGN 201634) from an Implant

TKI release was examined for implants made from poly (D,L-lactide-co-glycolide) (PDLG) or poly(D,L-lactide) (PDL) in different media with or without addition of detergent at 37° C. in a shaking water bath.

AGN 201634 was obtained from Allergan, and its chemical structure is shown below. It was used as received without further purification. PDLG/PDL polymer materials were obtained from Purac America Inc.

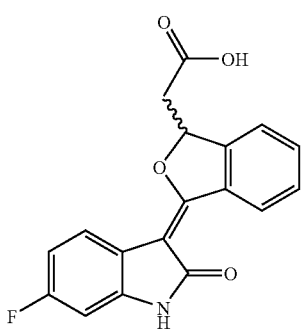 [SMILES: O=C(O)CC1O/C(=C2/C(=O)Nc3cc(F)ccc32)c2ccccc21]

TKI release was examined in various medium, including saline, phosphate buffer saline of pH 7.4, 50 mM bicarbonate buffer of pH 6.0±0.1 with 0.1% cetyltrimethylammonium bromide (CTAB), and 50 mM borate buffer of pH 8.5±0.1 with 0.5% sodium dodecyl sulfate (SDS) in a shaking water bath (Precision) at 37° C. Sample was incubated in 10 mL of medium, and was totally replaced with fresh medium at each sampling time. Drug concentration was determined by HPLC using a Waters 2690 Separation Module equipped with a Waters XTerra RP8 column (3.9×150 mm, 5 µm, equilibrated at ambient) and a Waters 996 photodiode array detector (set at 238 nm) using 0.1% acetic acid in acetonitrile/water (40/60 by volume) as the mobile phase under a flow rate of 1.2 mL/min. The column was equilibrated with mobile phase for at least 30 min before initiating any sample injection.

The characteristics of formulations, including formulation identification, Lot number, drug loading, inherent viscosity of polymer, and extrusion temperature are summarized in the following table. The drug load is from 20 to 50%. The formulations were extruded from a 750 µm nozzle to form cylindrical DDS.

TABLE 8

Characteristics of TKI formulations.

| Formulation # | Lot # | Drug Loading (%) | Polymer | I.V. | Extrusion Temp (° C.) |
|---|---|---|---|---|---|
| F1 | JS443159 | 40 | PDLG | 0.2 | 68 |
| F2 | JS443020 | 20 | PDLG | 0.2 | 70 |
| F3 | JS493023 | 50 | PDL | 0.5 | 85 |
| F4 | JS493034 | 30 | PDL | 0.5 | 78 |

Note:
I.V.: inherent viscosity of polymer material.

The stability of AGN 201634 standard solution in deionized water/acetonitrile (75%/25%) was examined at 4° C., and the results are summarized in the following table. The concentration of standard solution was from 0.0695 µg/mL to 8.693 µg/mL, and was analyzed on day 14, 21, and 35. The results show that the recovery was all greater than 95%, indicating a good stability of AGN 201634 in deionized water/acetonitrile (75%/25%) at 4° C. for up to 35 days even the concentration was up to 8.7 µg/mL.

Stability of AGN 201634 standard solution of various concentrations in DI water/acetonitrile (75%/25%) at 4° C. (Table 9).

| Day | Conc. Of Standard (µg/mL) | Recovery (%) |
|---|---|---|
| 14 | 0.0695 | 95.2 |
|  | 0.348 | 98.3 |
|  | 0.695 | 98.4 |
|  | 2.173 | 98.6 |
|  | 8.693 | 98.6 |
| 21 | 0.0695 | 96.5 |
|  | 0.348 | 101.3 |
|  | 0.695 | 102.1 |
|  | 2.173 | 101.0 |
|  | 8.693 | 101.6 |
| 35 | 0.0695 | 106.1 |
|  | 0.348 | 98.3 |
|  | 0.695 | 101.3 |
|  | 2.173 | 100.8 |
|  | 8.693 | 100.3 |

To examine the stability of TKI in formulation, Formulations 3 and 4 were prepared to various concentration in a medium of pH 6.0, 7.4 or 8.5, respectively, and subjected to an incubation condition of either 7 days under ambient condition or 14 days at 4° C., and the results are summarized in the following table. The results show that the recovery was all better than 98%, indicating that AGN 201634 was stable in media of pH 6.0, 7.4 and 8.5, and lasted for 7 days in ambient or 14 days at 4° C.

TABLE 10

Stability of TKI in Formulations 3 and 4 in media under various incubation conditions.

| Formulation | Medium | Concentration (µg/mL) | Incubation Time (day) | Incubation Temperature (° C.) | Recovery (%) |
|---|---|---|---|---|---|
| F3 | pH 6.0 | 5.60 | 7 | ambient | 100.1 |
|  |  | 3.45 | 14 | 4 | 102.7 |
|  | pH 7.4 | 2.53 | 7 | ambient | 101.1 |
|  |  | 2.29 | 14 | 4 | 103.7 |
|  | pH 8.5 | 10.34 | 7 | ambient | 100.8 |
|  |  | 10.24 | 14 | 4 | 98.8 |
| F4 | pH 6.0 | 0.94 | 7 | ambient | 100.4 |
|  |  | 0.84 | 14 | 4 | 102.4 |
|  | pH 7.4 | 0.18 | 7 | ambient | 104.3 |
|  |  | 0.48 | 14 | 4 | 101.3 |
|  | pH 8.5 | 1.39 | 7 | ambient | 100.4 |
|  |  | 1.20 | 14 | 4 | 100.2 |

Figure 11:
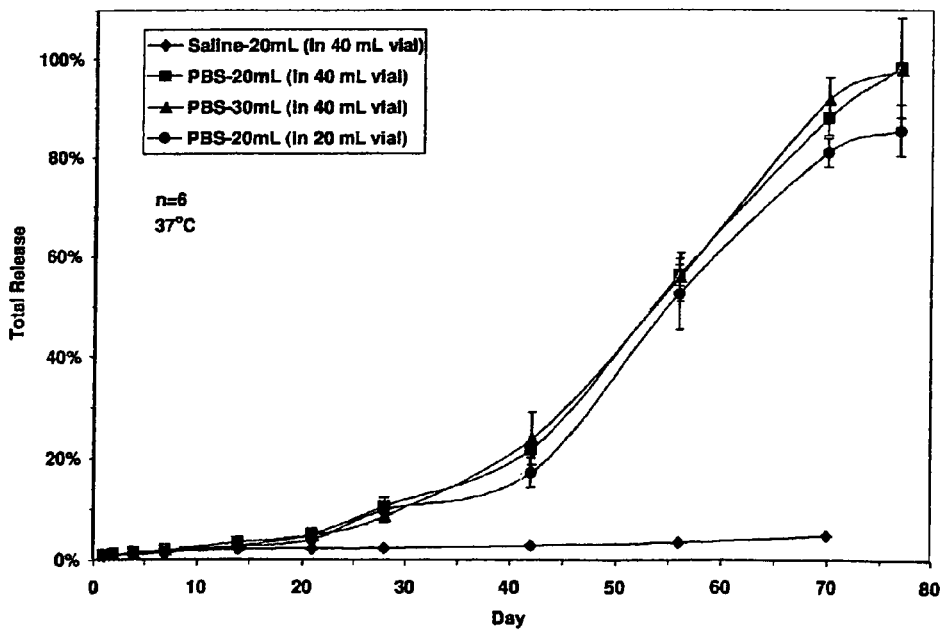
FIG. 11 is a graph of the cumulative release profile for TKI AGN 201634 of Formulation 1 in saline and PBS.

TKI releases of Formulation 1 in 20 mL of saline or 20-30 mL of PBS are demonstrated in FIG. 11. The DDS was incubated in a vial of either 40 or 20 mL, and 10 mL sample solution was replaced by same volume of fresh medium, respectively, at each sampling time. The release profiles in saline and PBS were obviously different. Less than 5% of TKI was released in saline during the first 70 days. In contrast, less than 5% of AGN 201634 was released at the first 3 weeks when DDS was incubated in PBS, the same as in saline, but more than 80% of AGN 201634 was released after 70 days. However, no significantly difference in release profile was found when DDS was incubated in 20 or 30 mL of PBS in a 20 or 40 mL vial. It seems that release medium plans an important role in the variation of release profile instead of incubation volume. Due to this slow and diverged release profile, the release profile of Formulation 2 was not performed since its formulation was based on the same polymer with a lower drug loading.

Figure 12:
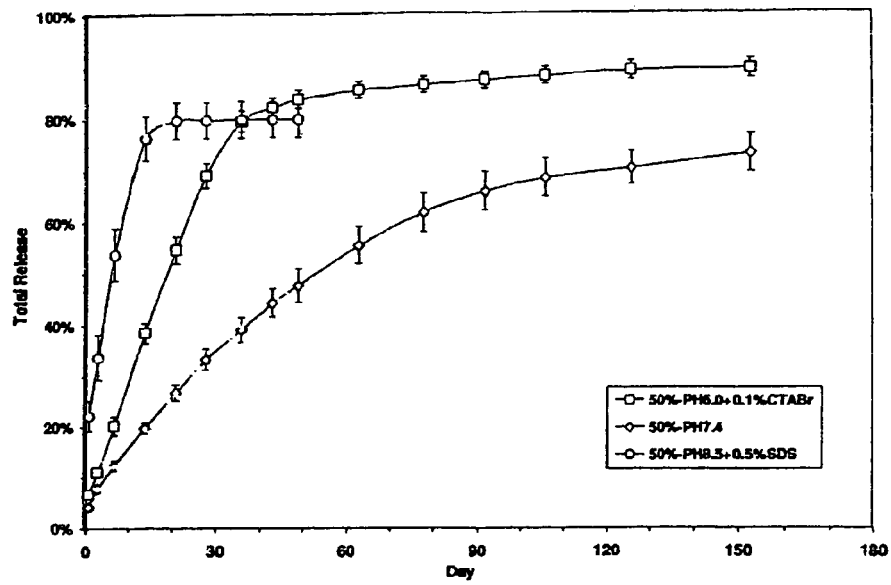
FIG. 12 is a graph of the cumulative release profile for TKI AGN 201634 release of Formulation 3 in media of a pH of 6.0 (with 0.1% CTAB), 7.4 (PBS) or 8.5 (with 0.5% SDS).
Figure 13:
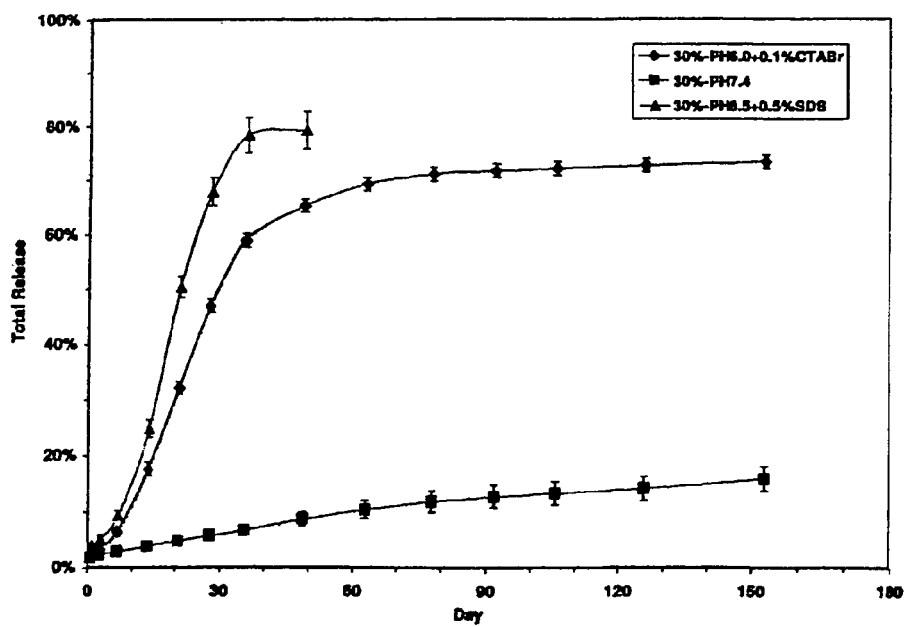
FIG. 13 is a graph of the cumulative release profile for TKI AGN 201634 release of Formulation 4 in media of a pH of 6.0 (with 0.1% CTAB), 7.4 (PBS) or 8.5 (with 0.5% SDS).

TKI releases of Formulations 3 and 4 in 10 mL media of a pH of 6.0 (with 0.1% CTAB), 7.4 (PBS) or 8.5 (with 0.5% SDS) at 37° C. are demonstrated in FIGS. 12 and 13, respectively. For F3, more than 50%, 45%, and 75% TKI was released at the first 3, 7, and 2 weeks, when DDS was incubated in a medium of pH 6.0 (with 0.1% CTAB), 7.4 (PBS) and 8.5 (with 0.5% SDS), respectively. On the other hand, approximately 47%, 6%, and 68% of TKI was released from F4 when DDS was incubated in media as described above. It seems that TKI release in different pH medium is pH 8.5>pH 6.0>pH 7.4, with or without the assistant from detergent in the medium. No large standard deviations are found in all media for both formulations.

To monitor the appearance of DDS during dissolution, the images of F3 and F4 formulations incubated in 10 mL media of a pH of 6.0 (with 0.1% CTAB), 7.4 (PBS) or 8.5 (with 0.5% SDS) at 37° C. were. All formulations experienced swelling followed by matrix degradation, resulting in drug release. No complete disintegration of formulation matrix was observed within 153 days at 37° C.

In summary, tyrosine kinase inhibitor (AGN 201634) DDS were formulated using various PLGA or PLA at various drug loading. The stability of AGN 201634 solution in DI water/acetonitrile (75%/25%) at 4° C. was more than 35 days, and DDS solution in various pH medium was more than 7 days under ambient condition or 14 days at 4° C. Different drug release profiles were found when DDS was tested in PBS or saline. Drug burst effect was found only in Formulation 3 when incubating in a medium of pH 6.0. Controlled AGN 201634 release in vitro was more than 4 weeks in a medium of pH 8.5, and more than 5 months in media of pH 7.4 and pH 6.0.

Example 5

Biodegradable Implants with a Linear Release Profile

Biodegradable implants are made by combining a TKI with a biodegradable polymer composition in a stainless steel mortar. The biodegradable polymer composition comprises a single type of biodegradable polymer. The combination is mixed via a Turbula shaker set at 96 RPM for 15 minutes. The powder blend is scraped off the wall of the mortar and then remixed for an additional 15 minutes. The mixed powder blend is heated to a semi-molten state at specified temperature for a total of 30 minutes, forming a polymer/drug melt.

Rods are manufactured by pelletizing the polymer/drug melt using a 9 gauge polytetrafluoroethylene (PTFE) tubing, loading the pellet into the barrel and extruding the material at the specified core extrusion temperature into filaments. The filaments are then cut into about 1 mg size implants or drug delivery systems. The rods have dimensions of about 2 mm long×0.72 mm diameter. The rod implants weigh between about 900 μg and 1100 μg.

Wafers are formed by flattening the polymer melt with a Carver press at a specified temperature and cutting the flattened material into wafers, each weighing about 1 mg. The wafers have a diameter of about 2.5 mm and a thickness of about 0.13 mm. The wafer implants weigh between about 900 μg and 1100 μg.

In-vitro release testing can be performed on each lot of implant (rod or wafer). Each implant may be placed into a 24 mL screw cap vial with 10 mL of Phosphate Buffered Saline solution at 37° C. and 1 mL aliquots are removed and replaced with equal volume of fresh medium on day 1, 4, 7, 14, 28, and every two weeks thereafter.

Drug assays may be performed by HPLC, which consists of a Waters 2690 Separation Module (or 2696), and a Waters 2996 Photodiode Array Detector. An Ultrsphere, C-18 (2), 5 μg/m; 4.6×150 mm column heated at 30° C. can be used for separation and the detector can be set at 264 nm. The mobile phase can be (10:90) MeOH-buffered mobile phase with a flow rate of 1 mL/min and a total run time of 12 min per sample. The buffered mobile phase may comprise (68:0.75:0.25:31) 13 mM 1-Heptane Sulfonic Acid, sodium salt-glacial acetic acid-triethylamine-Methanol. The release rates can be determined by calculating the amount of drug being released in a given volume of medium over time in μg/day.

The single polymer chosen for the implant was poly(caprolactone). Rod and wafer implants were formulated at a ratio of 50:50 (poly(caprolactone):TKI). Thus, a 1 mg implant comprises about 500 μg poly(caprolactone) and 500 μg TKI. AGN 200954 was used as the TKI.

Figure 15:
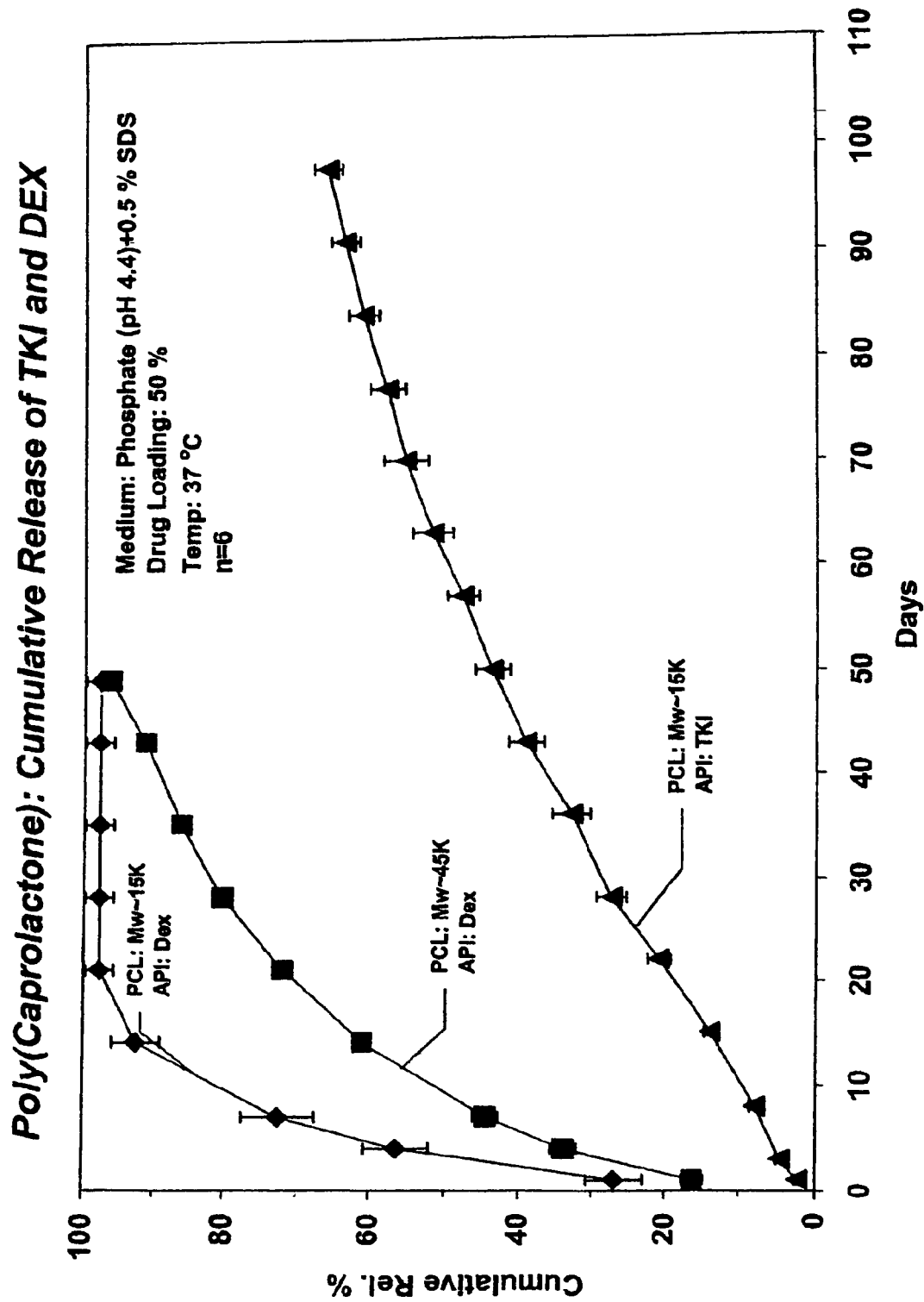
FIG. 15 is a graph of the cumulative release profile for a TKI-containing implant and Dexamethasone-containing implants, in which the biodegradable polymer is polycaprolactone.
Figure 16:
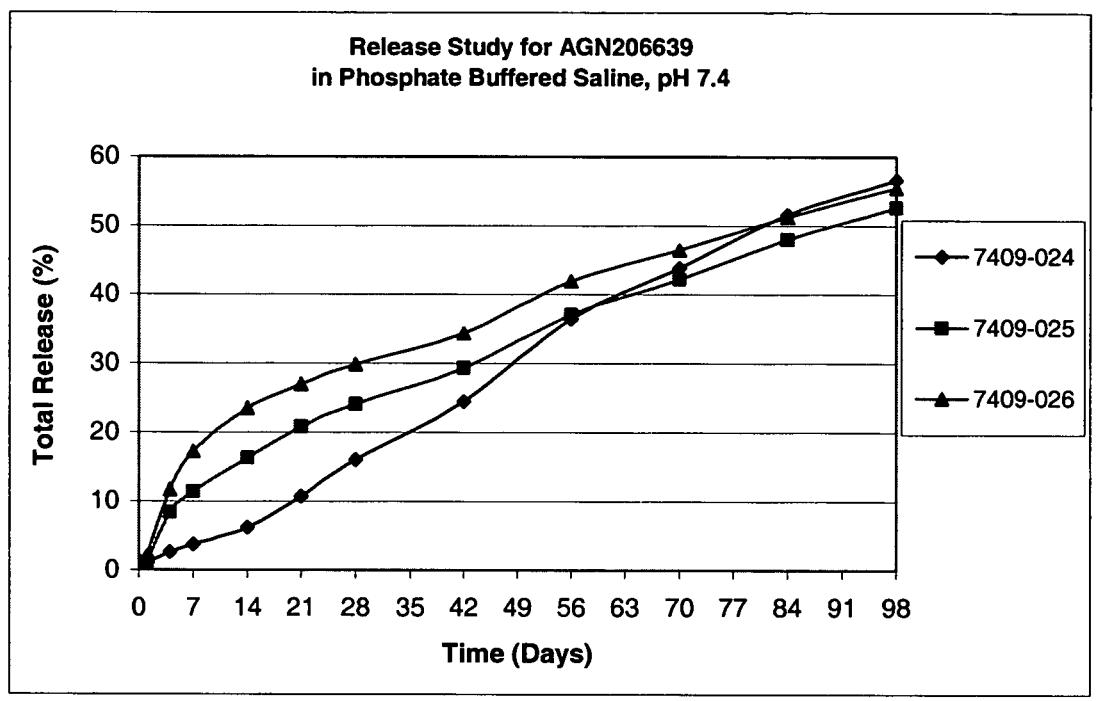
FIG. 16 is a graph of the cumulative release profile for three different formulations of TKI (AGN206639) containing implants in phosphate buffered saline release medium, pH 7.4.
Figure 17:
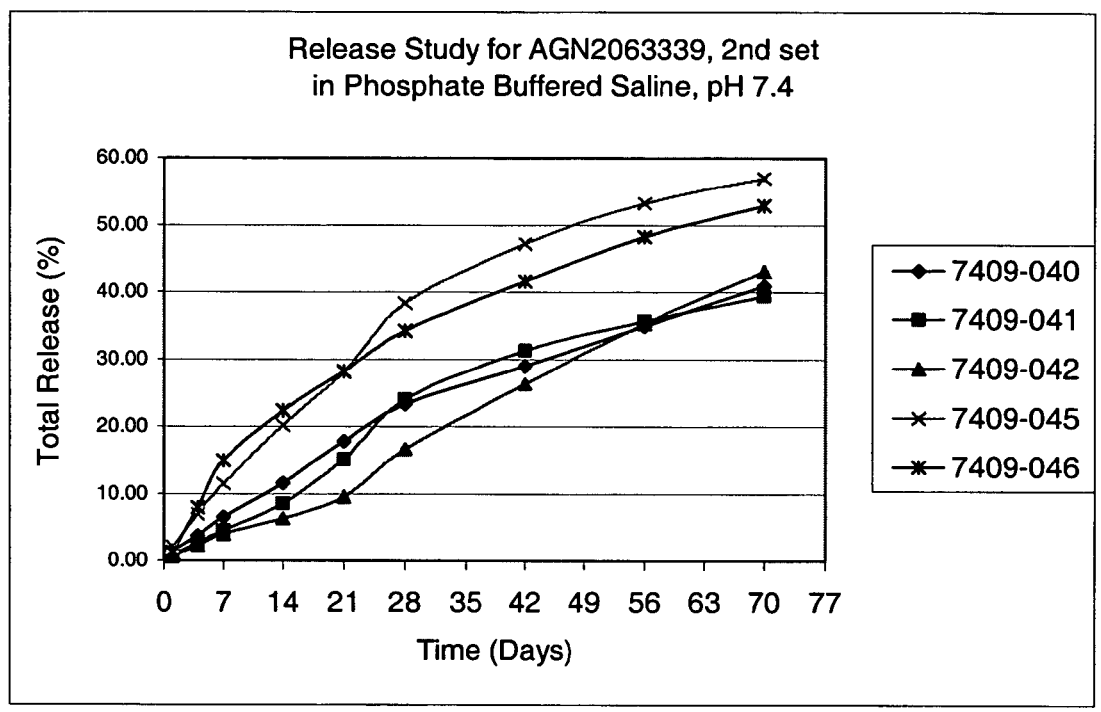
FIG. 17 is a graph of the cumulative release profile for five further and different formulations of TKI (AGN206639) containing implants in phosphate buffered saline release medium, pH 7.4.
Figure 18:
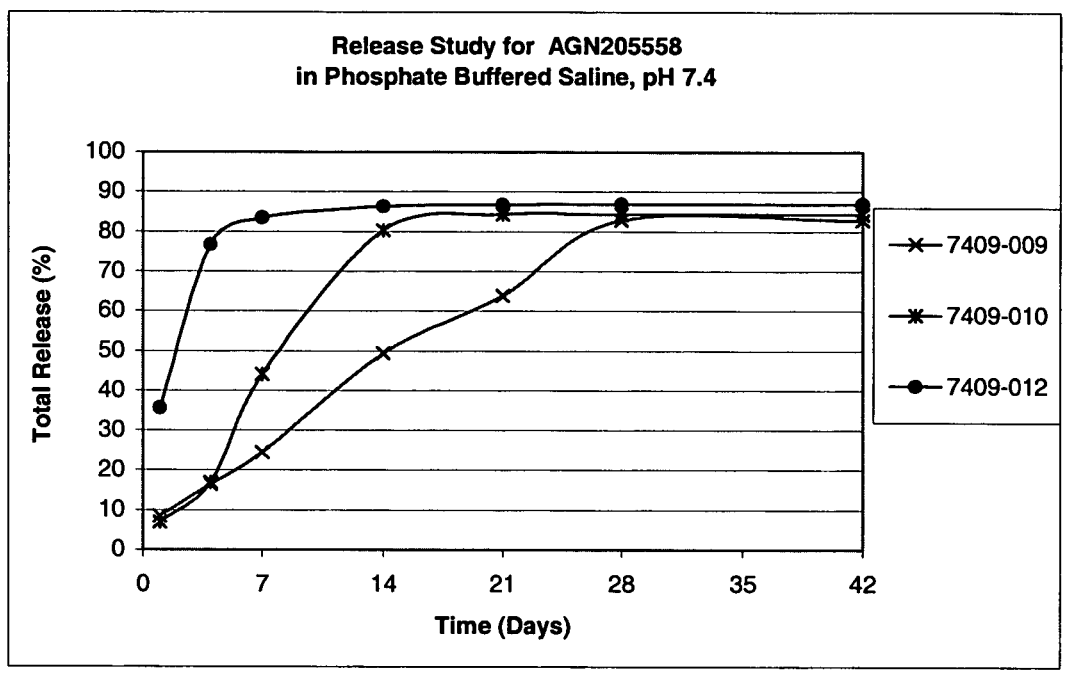
FIG. 18 is a graph of the cumulative release profile for three different formulations of TKI (AGN205558) containing implants in phosphate buffered saline release medium, pH 7.4.
Figure 19:
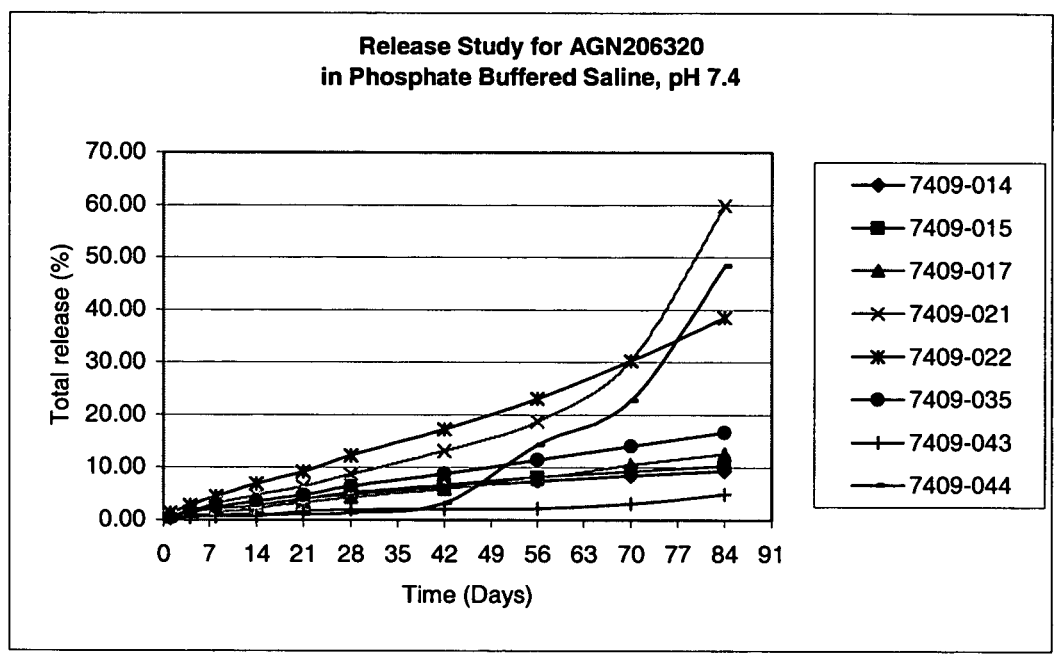
FIG. 19 is a graph of the cumulative release profile for eight different formulations of TKI (AGN206320) containing implants in phosphate buffered saline release medium, pH 7.4.
Figure 20:
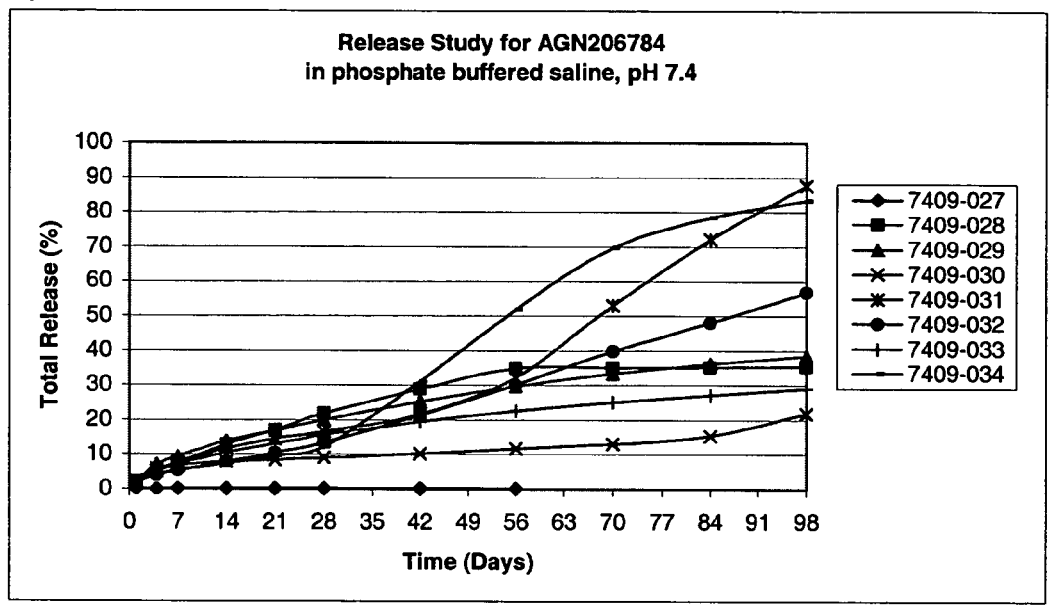
FIG. 20 is a graph of the cumulative release profile for eight different formulations of TKI (AGN206784) containing implants in phosphate buffered saline release medium, pH 7.4.
Figure 21:
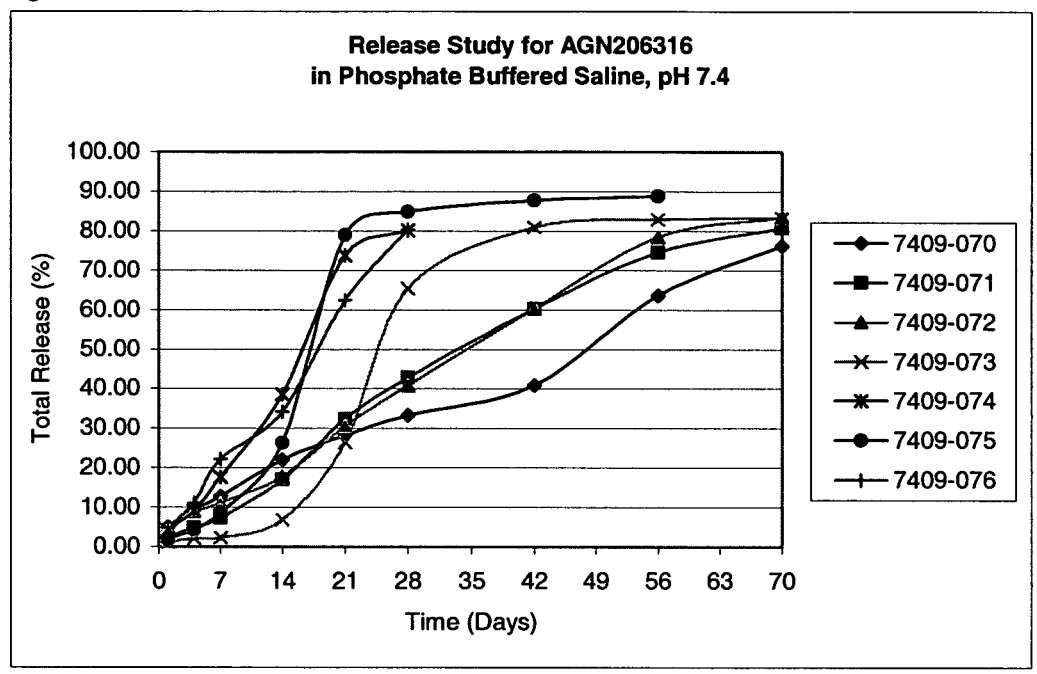
FIG. 21 is a graph of the cumulative release profile for seven different formulations of TKI (AGN206316) containing implants in phosphate buffered saline release medium, pH 7.4.

As shown in FIG. 15, implants formed from a poorly soluble drug (TKI) and a single type of a biodegradable polymer (poly(caprolactone)) released TKI at nearly zero-order rate for at least about 70 days. The particular poly(caprolactone) had a molecular weight of about 15 kilodaltons. The nearly linear release rate is extremely hard to achieve with other biodegradable implants based on a single polymeric component, as shown for the dexamethasone containing implants in FIG. 15.

Example 6

Manufacture and Testing of Implants Containing an TKI and a Biodegradable Polymer Matrix Additional biodegradable implants are made by combining a TKI with a biodegradable polymer composition as described in Example 5. The polymers chosen for the implants can be obtained from Boehringer Ingelheim or Purac America, for example. Examples of polymers include: RG502, RG752, R202H, R203 and R206, and Purac PDLG (50/50). RG502 is (50:50) poly(D,L-lactide-co-glycolide), RG752 is (75:25) poly(D,L-lactide-co-glycolide), R202H is 100% poly(D,L-lactide) with acid end group or terminal acid groups, R203 and R206 are both 100% poly(D,L-lactide). Purac PDLG (50/50) is (50:50) poly(D,L-lactide-co-glycolide). The inherent viscosity of RG502, RG752, R202H, R203, R206, and Purac PDLG are 0.2, 0.2, 0.2, 0.3, 1.0, and 0.2 dl/g, respectively. The average molecular weight of RG502, RG752, R202H, R203, R206, and Purac PDLG are, 11700, 11200, 6500, 14000, 63300, and 9700 daltons, respectively.

Example 7

In Vitro Evaluation of Various TKI Implants

Summary

TKIs can inhibit tyrosine kinase of vascular endothelial growth factor (VEGF). VEGF can induce angiogenesis and increases vascular permeability. Thus, TKIs can have utility to prevent or to treat choroidal neovascularization (CNV), such as CNV that can results from or be a symptom of, for example, age-related macular degeneration (AMD) and diabetic retinopathy (DRO).

In this experiment implants containing one of five different TKIs (receptor-mediated tyrosine kinase inhibitors) with antiangiogenic activity were made and evaluated. The implants were formulated as TKI, sustained release, biodegradable polymer implants with different poly(D,L-lactide-co-glycolide) and poly(D-L-lactide) polymers, made by a melt extrusion process. These implants are suitable for intraocular (such as intravitreal) use to treat one or more ocular disorders. Specifically, we made and evaluated controlled release intravitreal implants for the TKIs AGN206639, AGN205558, AGN206320, AGN206784, and AGN206316, showing that such implants can consistently release a TKI over a period of from about three to about six months. The implant formulations were evaluated in vitro in two different release media (phosphate buffered saline and citrate phosphate buffer with 0.1% cetyltrimethylammonium bromide). The effect of elevated temperature storage and of gamma sterilization on potency were also examined.

Although the implants were made by melt extrusion with poly(lactide) or poly (lactide-co-glycolide) polymers various implant formulations were made with or under different drug (TKI) load, lactide-glycolide ratio, intrinsic viscosity, and extrusion temperature. The polymer implant drug delivery systems (DDSs) made were assayed by HPLC for potency initially, post-sterilization, and after exposure to accelerated conditions. The TKI release from the DDS was assayed by HPLC after incubation in two different release media at 37° C.: (1) phosphate buffered saline (pH 7.4), and; (2) citrate phosphate buffer with 0.1% cetyltrimethylammonium bromide (pH 5.4). Generally, release rates were higher for similar polymer systems with higher drug (TKI) loading.

Table 11 sets forth the five different TKIs formulated into drug delivery systems (i.e. implants).

TABLE 11

Chemical properties of the TKIs AGN206639, AGN205558, AGN206320, AGN206784, and AGN206316.

| AGN Number | AGN206639 | AGN205558 |
|---|---|---|
| Chemical Structure | (structure image) | (structure image) |
| Tm (deg. C.) | Not detectable/Amorphous | 114.9, 133.2 |
| Solubility (ug/ml) in Water, 2 hours | N/A | N/A |
| Solubility (ug/ml) in pH 7.4 buffer, 2 hours | N/A | N/A |
| Solubility (ug/ml) in Water, 3 hours | 3.09 | 3.8 |
| Solubility (ug/ml) in pH 7.4 buffer, 3 hours | 17.91 | 31.6 |
| Solubility (ug/ml) in Water, 24 hours | N/A | N/A |
| Solubility (ug/ml) in pH 7.4 buffer, 24 hours | N/A | N/A |
| Solubility (ug/ml) in Water, 72 hours | 15.87 | 35.9 |
| Solubility (ug/ml) in pH 7.4 buffer, 72 hours | 29.19 | 96.2 |
| Release method | Supelco, HS F5 5 um column; 75:24.5:0.5 ACN:Water: Acetic acid w/5 mM HAS; 1 ml/min. for 10 min. | Supelco, HS F5 5 um column; 75:24.5:0.5 ACN:Water: Acetic acid w/5 mM HAS; 1 ml/min. for 10 min. |

TABLE 11-continued

Chemical properties of the TKIs AGN206639, AGN205558, AGN206320, AGN206784, and AGN206316.

| AGN Number | AGN206320 | AGN206784 |
|---|---|---|
| Chemical Structure | *(structure)* | *(structure)* |
| Tm (deg. C.) | 324.2 | 286.1 |
| Solubility (ug/ml) in Water, 2 hours | 0.2 | N/A |
| Solubility (ug/ml) in pH 7.4 buffer, 2 hours | 3.7 | N/A |
| Solubility (ug/ml) in Water, 3 hours | N/A | 10.71 |
| Solubility (ug/ml) in pH 7.4 buffer, 3 hours | N/A | 3.98 |
| Solubility (ug/ml) in Water, 24 hours | 0.5 | N/A |
| Solubility (ug/ml) in pH 7.4 buffer, 24 hours | 5 | N/A |
| Solubility (ug/ml) in Water, 72 hours | N/A | 11.86 |
| Solubility (ug/ml) in pH 7.4 buffer, 72 hours | N/A | 6.37 |
| Release method | Supelco, HS F5 5 um column; 75:24.5:0.5 ACN:Water: Acetic acid w/5 mM HAS; 1 ml/min. for 10 min. | Supelco, HS F5 5 um column; 60:40:1 ACN:Water: TFA 1 ml/min. for 10 min. |

| AGN Number | AGN206316 |
|---|---|
| Chemical Structure | *(structure)* |
| Tm (deg. C.) | 198.2, 261.6 |
| Solubility (ug/ml) in Water, | 2.1 |

TABLE 11-continued

Chemical properties of the TKIs AGN206639, AGN205558, AGN206320, AGN206784, and AGN206316.

| Property | Value |
|---|---|
| Solubility (ug/ml) in pH 7.4 buffer, 2 hours | 14.1 |
| Solubility (ug/ml) in Water, 2 hours | N/A |
| Solubility (ug/ml) in pH 7.4 buffer, 3 hours | N/A |
| Solubility (ug/ml) in Water, 3 hours | 6.6 |
| Solubility (ug/ml) in pH 7.4 buffer, 24 hours | 20 |
| Solubility (ug/ml) in Water, 24 hours | N/A |
| Solubility (ug/ml) in pH 7.4 buffer, 72 hours | N/A |
| Release method | Supelco, HS F5 5 um column; 75:24.5:0.5 ACN:Water:Acetic acid w/5 mM HAS; 1 ml/min. for 10 min. |

The polymers used to formulate the TKI drug delivery systems were:

Purasorb PDL, Poly(D,L-lactide), Purac Corp. lot #DG676GA (inherent viscosity [iv] is up to 6 dl/g, molecular weight [mw in Daltons] is up to 700K).

Resomer RG502, 50:50 Poly(D,L-lactide-co-glycolide), Boehringer Ingelheim Corp. Lot #R02M002 (iv is 0.16 to 0.24 dl/g).

Resomer RG502S, 50:50 Poly(D,L-lactide-co-glycolide), Boehringer Ingelheim Corp. Lot #Res-0354 (iv is 0.16 to 0.24 dl/g).

Resomer RG504, 50:50 Poly(D,L-lactide-co-glycolide), Boehringer Ingelheim Corp. Lot #1009731 (iv is 0.45 to 0.60 dl/g).

Resomer RG505, 50:50 Poly(D,L-lactide-co-glycolide), Boehringer Ingelheim Corp. Lot #223799 (iv is 0.61 to 0.74 dl/g).

Resomer RG506, 50:50 Poly(D,L-lactide-co-glycolide), Boehringer Ingelheim Corp. Lot #34034 (iv is 0.75 to 0.95 dl/g).

Resomer RG752, 75:25 Poly(D,L-lactide-co-glycolide), Boehringer Ingelheim Corp. Lot #R02A005 (iv is 0.16 to 0.24 dl/g).

Resomer RG755, 75:25 Poly(D,L-lactide-co-glycolide), Boehringer Ingelheim Corp. Lot #1009232 (iv is 0.50 to 0.70 dl/g).

Resomer R104, Poly(D,L-lactide), Boehringer Ingelheim Corp. Lot #290588 (mw is determined by the presence in the polymer of between about 1,500 and about 2,250 of the repeating monomer unit C3H4O2).

Resomer R207, Poly(D,L-lactide), Boehringer Ingelheim Corp. Lot #260911 (iv is 1.3 to 1.7 d/g).

Citrate phosphate buffer (CTAB) solution used was prepared by adding 27.56 g sodium dibasic phosphate heptahydrate, 9.32 g citric acid, and 2 g (1%) cetyltrimethylammonium bromide (CTAB, JT Baker) to a 2-L volumetric flask and filling with deionized water.

Phosphate buffered saline (PBS) solution used was prepared by adding two packets of PBS (Sigma catalog #P-3813) granules to a 2-L volumetric flask and adding deionized water.

Release Profile Standards

For stock standard preparation for compounds other than AGN206784, 5 mg was added into a 50-mL volumetric flask and acetonitrile was added to the mark. Working standards were prepared by adding 5 mL of stock standard to a 50-mL volumetric flask and adding a blend of 60:40 acetonitrile:water. For AGN206784 stock standard preparation, 5 mg of compound was added into a 50-mL volumetric flask and a solution of 80% acetonitrile and 20% water was added until full. For working standard preparation, 5 mL of stock standard was added to a 50-mL volumetric flask and a solution of 40:60 acetonitrile:water was added until full.

Release Profile Mobile Phase

Acetonitrile (ACN) was manufactured by Burdick and Jackson. Trifluoroacetic acid (TFA) was manufactured by Burdick and Jackson. A blend of 75:24.5:0.5 ACN:water: acetic acid with 5 mM hexanesulfonic acid was used for all analyses except for AGN206748 formulations where a blend of 60:40:1 ACN:Water:TFA was used as the mobile phase.

Equipment:

Powder blending: a Glenn Mills Inc. Turbula shaker type T2F, ID number 990720 was used. In addition, an F. Kurt Retsch GmbH & Co model MM200 ball mill was used.

Powder compaction: A modified Janesville Tool and Manufacturing Inc. pneumatic drive powder compactor, model A-1024 was used.

Piston Extrusion: A custom built piston extruder produced by APS Engineering Inc. was used with a Watlow 93 temperature controller and thermocouple.

Weighing: A Mettler Toledo MT6 balance, S/N 1118481643 was used. Sample incubation: A Precision Inc. Reciprocal Shaking Bath with water was used.

HPLC: A Waters LC module 1 plus, S/N M98LCJ242M with a Supelco HSF5 µm, 4.6×150 mm column and Waters 2487 dual wavelength absorbance detector was used. Data was analyzed using Peak Pro software, version 9.1b.

Powder Blending

The drug (TKI) was stored at room temperature with minimal light exposure, and polymers were stored at 5° C. and allowed to equilibrate to room temperature prior to use. Both materials were used as received. Formulations, listed in Table 12, were blended in a stainless steel mixing capsule with two stainless steel balls and placed in a Retsch mill at 30 cps or Turbula blender at 96 rpm for 5 to 15 minutes. Depending on the starting materials, formulations underwent four to six blending cycles at five to fifteen minutes each. Between blending cycles, a stainless steel spatula was used to dislodge material from the inside surfaces of the mixing vessel. Formulation ratios and extrusion temperatures for all formulations are listed in Table 2.

Powder Compaction

A die with a 720 µm opening was attached to a stainless steel barrel. The powder compactor was set to 50 psi. The barrel was inserted into the powder compactor assembly. A stainless steel powder funnel was used to add a small amount of powder into the barrel and then the pneumatic compactor was actuated. This process was repeated until the barrel was full or no more powder remained.

Extrusion

A piston extruder was set to temperature and allowed to equilibrate. The extrusion temperature was chosen based on drug load and polymer. The extrusion temperature was adjusted for each formulation to produce smooth, uniform looking filaments. After the extruder temperature equilibrated, the piston extrusion barrel was inserted into the extruder, and a thermocouple was inserted to measure the temperature at the surface of the barrel. After the barrel temperature equilibrated, the piston was inserted into the barrel and the piston speed was set at 0.0025 in/min. The first 2-4 inches of extrudate was discarded. Afterwards, 3-5-inch pieces were cut directly into a centrifuge tube. Samples were labeled and stored in a sealed foil pouch containing desiccant.

Formulations with higher drug load required higher extrusion temperatures. Polymers with higher intrinsic viscosities required higher extrusion temperatures than polymers with lower intrinsic viscosities. Lactide-glycolide co-polymers with a higher lactide percentage (75:25) required a lower processing temperature than polymers with a lower lactide percentage (50:50). Formulation information and extrusion temperatures are listed in Table 12.

Content Uniformity Analysis

Ten samples of 1 mg (+/−10%) were cut from each formulation. Each was weighted and placed individually into 50-mL volumetric flasks. For AGN206784, a 40:60 ACN: Water or 100% acetonitrile was added and samples were sonicated. Samples were analyzed according to the HPLC method used for release profile analysis, below. For the other TKIs, a 60:40 ACN:Water was added to each 50-mL volumetric flask. Flasks were sonicated and samples were tested according to the same HPLC method that is used for in-vivo release (below).

Gamma Sterilization

Samples were weighed and packaged in vials, and each vial was sealed in a foil pouch with desiccant and labeled. All samples were sterilized with 25-40 kGy of gamma radiation.

Stability Testing:

Filaments were cut into 1 mg (+/−10%) samples and packaged together in screw-top vials. Formulations were then placed in an oven at 40° C. and ambient humidity. After 14 days, samples were tested for percent TKI content.

In Vitro Release Profile Analysis

Twelve samples of 1 mg (+/−10%) were cut from each formulation. Each sample was then weighed and placed individually into 60-mL sample vials. Fifty milliliters of citrate phosphate buffer solution was added to six vials and fifty milliliters of phosphate buffered saline release media was added to six vials. All vials were placed into a shaking water bath set at 37° C. and 50 RPM. At each time point 2 mL was taken from each vial for analysis, the remaining solution was disposed of, and 50 mL of new release media was added to the vial.

TABLE 12

Formulation conditions for TKIs AGN206639, AGN205558, AGN206320, AGN206784, and AGN206316 Implants.

| API | Formulation # | API Loading (%) | Polymer(s) | Extrusion Temp (Deg. C.) |
|---|---|---|---|---|
| AGN206639 | 7409-007 | 50 | Purac PDL* | 80 |
| | 7409-023 | 60 | Purac PDL | 75 |
| | 7409-024 | 50 | Resomer RG752± | 81 |
| | 7409-025 | 50 | Resomer RG755† | 92 |
| | 7409-026 | 60 | Resomer RG755 | 94 |
| | 7409-040 | 40 | Resomer RG755 | 94 |
| | 7409-041 | 30 | Resomer RG755 | 94 |
| | 7409-042 | 40 | Resomer RG752 | 84 |
| | 7409-045 | 40 | Resomer RG502** | 96 |
| | 7409-046 | 40 | Resomer RG505•• | 103 |
| AGN205558 | 7409-009 | 50 | Resomer RG755 | 96 |
| | 7409-010 | 60 | Resomer RG755 | 98 |
| | 7409-012 | 50 | Resomer R104†† | 67 |
| AGN 206320 | 7409-014 | 50 | Resomer RG755 | 110 |
| | 7409-015 | 60 | Resomer RG755 | 115 |
| | 7409-017 | 50 | Res.RG755, Res. R104, 3:2 | 94 |
| | 7409-021 | 50 | Resomer RG506○ | 117 |
| | 7409-022 | 50 | Resomer R104 | 71 |
| | 7409-035 | 50 | Resomer R207‡ | 139 |
| | 7409-043 | 40 | Resomer RG752 | 83 |
| | 7409-044 | 40 | Resomer RG502 | 94 |
| AGN206784 | 7409-027 | 50 | Resomer RG755 | 107 |
| | 7409-028 | 60 | Resomer RG755 | 118 |
| | 7409-029 | 50 | Purac PDL | 109 |
| | 7409-030 | 50 | Resomer R104 | 80 |
| | 7409-031 | 50 | Resomer RG506 | 129 |
| | 7409-032 | 60 | Res. RG755, Res. R104, 1:1 | 100 |
| | 7409-033 | 50 | Resomer R207‡ | 139 |
| | 7409-034 | 60 | RG502S | 96 |
| AGN206316 | 7409-070 | 60 | Resomer RG755 | 114 |
| | 7409-071 | 40 | Resomer RG755 | 95 |
| | 7409-072 | 60 | Resomer RG752 | 91 |
| | 7409-073 | 40 | Resomer RG752 | 91 |
| | 7409-074 | 60 | Resomer RG502 | 102 |

TABLE 12-continued

Formulation conditions for TKIs AGN206639, AGN205558, AGN206320, AGN206784, and AGN206316 Implants.

| API | Formulation # | API Loading (%) | Polymer(s) | Extrusion Temp (Deg. C.) |
|---|---|---|---|---|
| | 7409-075 | 40 | Resomer RG502 | 93 |
| | 7409-076 | 60 | Resomer RG504• | 121 |

*Purac PDL = Purac 50:50 Poly(D, L-lactide-co-glycolide)
**Resomer RG502, RG502S = Boehringer Ingelheim 50:50 Poly(D, L-lactide-co-glycolide), IV = 0.16-0.24(dl/g)
•Resomer RG504 = Boehringer Ingelheim 50:50 Poly(D, L-lactide-co-glycolide), IV = 0.45-0.60(dl/g)
••Resomer RG505 = Boehringer Ingelheim 50:50 Poly(D, L-lactide-co-glycolide), IV = 0.7(dl/g)
oResomer RG506 = Boehringer Ingelheim 50:50 Poly(D, L-lactide-co-glycolide), IV = 0.8(dl/g)
±Resomer RG752 = Boehringer Ingelheim 75:25 Poly(D, L-lactide-co-glycplide), IV = 0.2(dl/g)
†Resomer RG755 = Boehringer Ingelheim 50:50 Poly(D, L-lactide-co-glycolide), IV = 0.6(dl/g)
††Resomer R104 = Poly(L-lactide), MW = 2000
‡Resomer R207 = Poly(L-lactide), IV = 1.6

In Table 12 the API (active pharmaceutical ingredient [i.e. the TKI] value is a weight percent value.

HPLC Assay

The HPLC was conditioned until stable at 1 mL per minute flow rate at 280 nm. Samples were transferred to auto sampler vials with added samples for system suitability and standardization. Total run time was 10 minutes, temperature was ambient and injection volume was 20 µL. Samples were taken on day 1, 4, 7, and at 7 day intervals after that until the studies were ended or 100% release was achieved. The total TKI present was calculated from the height of the peak at 280 nm compared to the height of the standard peak. Percent of drug released, total micrograms released, and standard deviations within formulations were calculated from the amount of drug detected.

Results

The content uniformity analysis carried showed that most formulations tested at 100% label strength plus or minus 20%.

FIGS. 16 to 21 are graphs which provide examples of in vitro release data (in either pH 5.4 citrate phosphate buffer release medium or in pH 7.4 phosphate buffer saline release medium) for the five TKI used in implants with varying polymer formulations. FIGS. 16 to 21 show that TKIs with higher solubilities had the tendency to release at a faster rate than TKIs with lower solubilities. Additionally, FIGS. 16 to 21 show that TKI implant formulations with lower drug (TKI) loading released at a slower rate than those with a higher drug loading.

Thus, a number of different sustained release biodegradable polymeric formulations (implants) were made for five different tyrosine kinase inhibitor compounds. The results show that the release of TKIs from PLGA polymer implants can be modified by changing polymer matrices and extrusion conditions. Notably, sustained release was achieved for all five TKI compounds in phosphate buffered saline release medium (pH 7.4) and CTAB media and the results show that TKI release from the polymer matrix can last from about one to over six months, depending on the formulation. Significantly, linear, consistent drug release profiles were obtained achieved from for each of the five TKIs in phosphate buffered saline (see formulations 7409-024, 7409-009, 7409-022, 7409-032, and 7409-071).

Example 8

Processes for Making Active Agent Microspheres

An experiment was carried out to make microspheres incorporating one or more active agents (such as a tyrosine kinase inhibitor). A known emulsion-evaporation process for making active agent microspheres is shown in FIG. 22. In this known process, an organic phase comprising an active agent, a polymer for encapsulating the active agent, and a solvent for both is prepared. An aqueous phase is prepared and the two phases are combined to form an emulsion. The emulsion is stirred and the solvent is evaporated. The resulting microspheres are collected, sized (sieving) and freeze dried for later use. Typically, the classical emulsion/evaporation process results in microparticles which show a burst release of an active agent from the microparticles. Additionally, the known process generally permits no more than about a 10% (by weight of the microparticle) loading of the active agent into the microparticle.

We developed a new (oil in water) process for making active agent microspheres (FIG. 23). This new process for making microspheres can be used with any small molecule which is slightly soluble in water and organic solvents and which is able to preferentially crystallize in organic solvents. Such small molecules include those which have a Log P greater than or equal to four. P, the partition coefficient, is defined as the ratio of the equilibrium concentration ($C_i$) of a dissolved substance in a two-phase system consisting of two largely immiscible solvents, for example the ratio of noctanol ($C_o$) to water ($C_w$).

In our modified process, as in the known process, an organic phase and an aqueous phase is prepared. We modified the known emulsion/evaporation process by:

(1) reducing the volume of the organic phase which contains the active agent and the polymer (for example a PLA or PLGA co-polymer) which is used to encapsulate the active agent, so as to promote crystallization of the active agent. Preferably, the pH of the aqueous phase I is between about pH 6 and 8.

In our process the volume of the organic phase containing the active agent and the polymer (i.e. a PLA and/or a PLGA) was reduced by about 80% to force the active agent to crystallize and/or precipitate and therefore to be embedded within the polymer. Thus, a significant difference with our new process was with regard to the concentration of the polymer (i.e. a PLGA) in the organic solvent. For example, in the known process about 450 mg of PLGA is dissolved in about 25-30 ml of methylene chloride, while with our new process, for example, about 450 mg of PLGA was dissolved in only 5 ml of the solvent, methylene chloride. Thus, we used a higher concentration of a PLGA in the methylene chloride, providing a more viscous organic phase.

(2) using two aqueous phases. The first aqueous phase (aqueous phase 1) is used to assist formation a stable emulsion with the organic phase. The second aqueous phase (aqueous phase 11) serves as a sink, extracting the organic phase and assisting formation of a stable suspension for the solvent evaporation step.

(3) the volume of the aqueous extraction phase (aqueous phase 11 or a water co-solvent system) is calculated based on the volume of the solvent (i.e. methylene chloride) used in the organic phase in order to fully dissolve it. The aqueous phase 11 is used to dissolve the solvent, to remove the organic solvent from the microspheres and to obtain hard microspheres that are stable in suspension during the evaporation step. During the evaporation process the organic solvent is removed from the aqueous phase to obtain solid microspheres.

(4) permitting the active agent to crystallize. We determined that active agent crystallization can provide preferential microsphere characteristics. With our new process crystallization of the active agent proceeds in the viscous medium (mixture of organic phase, polymer and active ingredient) upon air flow evaporation or reduced pressure of the solvent. We found that the more the active agent crystallizes in this reduced volume organic phase, the more active agent there is encapsulated by the polymer.

(5) establishing a pH of the aqueous extraction phase (the aqueous phase II or a water co-solvent system) such that the solubility of the active agent in the aqueous II phase is limited, that is to maximize the Log D (the water/octanol distribution coefficient). Thus, the pH of the aqueous phase II is adjusted in order to limit the solubility of the active in aqueous (Log D max).

Preferably, the pH of the aqueous phase II is between about 4 and 9.

In particular, use of crystal formation in order to encapsulate an active agent is a significant improvement of the known emulsion/evaporation process. Advantages of our new process include:

(1) elimination or a significant reduction of the burst effect of release of an active agent from the microparticles. This elimination or reduction may be due to the promotion of active agent crystal formation by our process, and;

(2) a higher loading (10-30 wt %) of the active agent in the microspheres.

In both the known and in our new process the ratio between the volumes of organic phase solvent (i.e. methylene chloride) and aqueous phase used is about the same (between about 1:5 and 1:6). For example, in both processes for a 3 g batch the aqueous phase comprises about 1000 ml of water while the organic phase comprises about 180 ml of methylene chloride).

Using our new process, each of the five different TKIs shown by FIG. 24 were separately incorporated into PLGA biodegradable microspheres. In FIG. 24 the five TKIs shown are identified as follows: first (uppermost) row: 206639 and 205558; second (middle) row: 206320 and 206316, and; bottom row: 206784. The properties of these five TKIs are set forth in Table 13, where "DSC" means differential scanning calorimetry and endotherms are noted in degrees Celsius (used to determine presence of TKI crystals).

TKI PLGA microspheres with up to an 11% loading of the TKI active agent in the PLGA polymer were made using our new process as follows:

Aqueous Phase (I) Preparation

A 1.5% PVA polyvinyl alcohol) solution was prepared and adjusted to pH between 6 and 8 depending on the highest value of Log D (i.e. the Log D max) for the active agent TKI used. The pH range used ensured formation of the desired emulsion. About pH 8 and below about pH 6, the conditions are not favorable for formation of an emulsion. A separate beaker with 600 ml of distilled water was then adjusted to the exact pH of Log D max. As previously set forth, the partition coefficient (P) is defined as the ratio of the equilibrium concentrations ($C_i$) of a dissolved substance in a two-phase system consisting of two largely immiscible solvents; in this experiment, n-octanol and water.

Po/w is the ratio of C n-octanol/C water. Thus, the partition coefficient (P) is the quotient of two concentrations and is usually given in the form of its logarithm to base ten (log P). Specifically, log P is related to the solubility of a molecule (neutral form) in organic solvents. Thus, if Lop P is greater than 4 the molecule is very soluble in organic solvent and insoluble in water. On the other hand if the active agent has a 0<Log P<1, it is soluble in water in limited quantity. Finally, if the active agent has a log P less than <0, it is highly soluble in water and insoluble in organic solvents. Depending on a compound's crystal lattice energy it can also possess low solubility in both water and organic solvents. These compounds (active agents) can also be used in this invention by adjusting the pH of aqueous phase 11 to the compounds log D max. Additionally, active agents with considerable lipophilic bulk and ionizable functional groups can possess a high log D at the appropriate pH and a high solubility at a pH where the compound is ionizable. Further, lipophilic compounds made more water soluble with flexible side chains that disrupt their crystal lattice energy or confer librational entropy to the compound in aqueous environments can also be used in this invention by optimizing the pH of aqueous phase II to maximize the log D of the compound.

If an active agent to be evaluated contains more than one functional group with different property (acidic and basic), then the log D needs to be used (log D is also a partition coefficient, but is linked to the pH).

Organic Phase Preparation

To 50 mg of AGN TKI in a small Erlenmeyer flask, 5 ml of methylene chloride was added. If the active is not solubilized, 5 other ml is added. Again if not enough, 5 more is added again. 450 mg of PLGA 75/25 (75% by polylactide, 25% by weight polyglycolide copolymer) was then added in the solution. After complete dissolution and even if the solution was

TABLE 13

Physical properties of the TKI Active Agents

| | TKI | | | | |
|---|---|---|---|---|---|
| | 206639 | 205558 | 206320 | 206784 | 201634 |
| DSC (° C.) | Not detectable | 114.9-133.2 | 198.2-261.6 | 324.2 | 286.1 |
| Log P | 3.19 | 5.56 | 2.27 | 2.57 | 2.45 |
| pH Log D max | 9.3-9.4 | 10.2 | 10.3-10.4 | <2.6 | 4 |
| Aqueous solubility (µg/ml) | 3.09 | 3.8 | unknown | 10.71 | 23.15 |
| CH2Cl2 solubility | Soluble | Soluble | Slightly Soluble | Insoluble | Insoluble | still turbid, this phase was concentrated with an air flow on the solution in order to obtain 5 ml of a slightly viscous solution.

Emulsion Preparation

In a small beaker with a high shear impeller, a 1.5% PVA solution was added just to cover the impeller. 2 ml of $CH_2Cl_2$ was added with a high mixing until emulsion formation to saturate the organic phase. The organic phase prepared (see above) was slowly added with stirring.

Co-Solvent Extraction with Aqueous Phase II

Then, after a few seconds of high shear stirring, the 600 ml beaker of water (aqueous phase II) was added to the emulsion under magnetic stirring. The pH of the emulsion was adjusted by the addition of aqueous phase II (thereby forming an aqueous suspension of the newly made TKI PLGA microparticles) to bring the pH of the suspension to the pH of the log D max of the TKI used (as set forth for example in Table 13). The aqueous phase II can be water.

Evaporation

The solution was evaporated overnight under air flow to harden the microspheres.

Centrifugation

After centrifugation and rinsing with water and before lyophilization an analysis was performed to evaluate microscopic aspect and particle size. The particles obtained were sieved on 45 µm sieve size to select part of the batch with size able to pass through a 27 G needle. Generally, the microspheres made have a size between about 30-50 microns, with a peak diameter distribution at about 40 microns.

Freeze-Drying

The microsphere suspension was collected in vials, freeze-dried for 14 hours and capped. In the freeze drier during the lyophilization step containers were open (5 ml glass vials), at the end of the cycle the vacuum was partially replaced by nitrogen and then the containers closed directly inside the freeze drier under nitrogen and 800 mbar pressure.

This experiment showed that our new method can be used to prepare active agent microspheres.

Example 9

In Vitro Evaluation of TKI Microspheres

A further experiment was carried out to determine the in vitro release profiles of the TKI active agent microspheres made by the process of in Example 8. It was determined that the Example 8 method permitted preparation of active agent microspheres encapsulating, for example, up to about 11 wt % of a TKI active agent.

The in vitro release profiles for the TKI PLGA microspheres made in Example 9 were determined as follows. The release medium contained the following four reagents: disodium phosphate dodecahydrate ($Na_2HPO_4$ $12H_2O$); potassium dihydrogen phosphate ($KH_2PO_4$) sodium chloride (NaCl) and; deionised water. The release medium was prepared by dissolving 2.38 g of disodium phosphate dodecahydrate, 0.19 g of potassium dihydrogen phosphate, and 8.0 g of sodium chloride in deionised water. This was then diluted to 1000 ml with the same solvent and the pH was adjusted to 7.4.

50 mg of the TKI microspheres were placed into a dialysis tube (Spectra/Por CE Dispodialyzer MWCO=50 000 Da, Ø5 mm, sample volume 1 ml, ref Spectrum 135222, or equivalent), 1.0 mL of the release medium was added and the tube was closed. Into a 50 mL centrifugation tube 50.0 mL of the release medium was added. The dialysis tube was placed in the centrifugation tube, ensuring a total immersion and the tube was tightly closed. The centrifugation tube was then placed in a shaker water bath (37° C./25 rpm).

At each time point of the release, 40.0 mL of the prepared release medium was pipetted out using a volumetric pipet and replaced with 40.0 mL of fresh release medium. The sampling time points included $T_0$ (time zero), 24 hours, 48 hours, 5 days, 8, 12, 16, 19, 22, and 26 days after placement into the release medium.

Subsequently, high performance liquid chromatography (HPLC) comprised of a Waters® XTerra Phenyl chromatography column using a gradient composed of acetonitrile and water/glacial acetic acid (99.5/0.5) was used to determine the in vitro release prove of each of the five different TKI PLGA microspheres made. Detection was by UV absorbance at 280 nm and quantitation was based on peak areas.

FIG. 25 presents the in vitro release profiles for the five TKI microspheres made.

Factors relevant to the release profile of the TKI from the PLGA microspheres polymer include the solubility of the TKI in the dissolution media. In all cases, burst appears limited, the maximum burst being about 1% of the total active encapsulated.

This experiment determined that TKI PLGA microspheres made using the Example 8 process can release a TKI in vitro over a period of time in excess of 28 days.

All references, articles, publications and patents and patent applications cited herein are incorporated by reference in their entireties.

While this invention has been described with respect to various specific examples and embodiments, it is to be understood that the invention is not limited thereto and that it can be variously practiced within the scope of the following claims.

We claim:

1. A biodegradable intravitreal implant comprising:
a plurality of biodegradable polymer microspheres comprising a tyrosine kinase inhibitor (TKI) and a biodegradable polymer matrix, the microspheres releasing the TKI at a rate effective to sustain release of the TKI from the microspheres for at least about one week to about 1 year after the implant is placed in the vitreous of an eye, wherein the tyrosine kinase inhibitor is provided in an amount from about 40% by weight to about 60% by weight of the implant, and the biodegradable polymer matrix comprises a poly(lactide-co-glycolide) in an amount from about 40% by weight to about 60% by weight of the implant.

2. The implant of claim 1, wherein the microspheres release the TKI at a rate effective to sustain release of an amount of the TKI from the implant for at least about one month to about one year from the time the implant is placed in the vitreous of the eye.

3. A method of treating an ocular condition of an eye of a patient, comprising the step of placing biodegradable intraocular microspheres into the vitreous of an eye of the patient, the microspheres comprising a tyrosine kinase inhibitor (TKI) and a biodegradable polymer matrix, wherein the microspheres degrade at a rate effective to sustain release of an amount of the TKI from the microspheres for a period of time in the range of about one week to about one year, effective to treat the ocular condition and wherein the tyrosine kinase inhibitor is provided in an amount from about 40% by weight to about 60% by weight of the implant, and the biodegradable polymer matrix comprises a poly(lactide-co-glycolide) in an amount from about 40% by weight to about 60% by weight of the implant.

4. The method of claim 3, wherein the method is effective to treat a retinal ocular condition.

5. The method of claim 3, wherein the ocular condition is glaucoma.

6. The method of claim 3, wherein the ocular condition is proliferative vitreoretinopathy.

7. The method of claim 3, wherein the ocular condition is choroidal neovascularization.

* * * * *